(12) United States Patent
Hartley et al.

(10) Patent No.: US 7,468,040 B2
(45) Date of Patent: Dec. 23, 2008

(54) METHODS AND SYSTEMS FOR IMPLANTABLY MONITORING EXTERNAL BREATHING THERAPY

(75) Inventors: Jesse W. Hartley, Lino Lakes, MN (US); Quan Ni, Shoreview, MN (US); Jeffrey E. Stahmann, Ramsey, MN (US); Kent Lee, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 736 days.

(21) Appl. No.: 10/929,826

(22) Filed: Aug. 30, 2004

(65) Prior Publication Data

US 2005/0061319 A1     Mar. 24, 2005

Related U.S. Application Data

(60) Provisional application No. 60/504,257, filed on Sep. 18, 2003.

(51) Int. Cl.
    *A61B 5/08* (2006.01)
(52) U.S. Cl. ........................... 600/529; 600/509
(58) Field of Classification Search ............ 600/529, 600/533, 509, 536; 607/42
    See application file for complete search history.

(56) References Cited

U.S. PATENT DOCUMENTS

| 4,365,636 A | 12/1982 | Barker |
| 4,562,841 A | 1/1986 | Brockway et al. |
| 4,813,427 A | 3/1989 | Schlaefke et al. |
| 4,830,008 A | 5/1989 | Meer |
| 4,928,688 A | 5/1990 | Mower |
| 5,036,849 A | 8/1991 | Hauck et al. |
| 5,123,425 A | 6/1992 | Shannon, Jr. et al. |
| 5,146,918 A | 9/1992 | Kallok et al. |
| 5,187,657 A | 2/1993 | Forbes |
| 5,203,348 A | 4/1993 | Dahl et al. |
| 5,211,173 A | 5/1993 | Kallok et al. |
| 5,215,082 A | 6/1993 | Kallok et al. |
| 5,230,337 A | 7/1993 | Dahl et al. |
| 5,233,983 A | 8/1993 | Markowitz |
| 5,284,136 A | 2/1994 | Hauck et al. |
| 5,301,677 A | 4/1994 | Hsung |
| 5,313,953 A | 5/1994 | Yomtov et al. |

(Continued)

FOREIGN PATENT DOCUMENTS

WO          99/04841          4/1999

(Continued)

OTHER PUBLICATIONS

Bradley et al., *Pathophysiologic and Therapeutic Implications of Sleep Apnea in Congestive Heart Failure*, 3 J. Cardiac Failure 223-240 (1996). Abstract only.

Bradley et al., *Sleep Apnea and Heart Failure, Park I: Obstructive Sleep Apnea*, 107 Circulation 1671-1678 (2003).

(Continued)

*Primary Examiner*—Carl H. Layno
*Assistant Examiner*—Jon-Eric Morales
(74) *Attorney, Agent, or Firm*—Hollingsworth & Funk, LLC

(57) ABSTRACT

An implantable device is used to monitor one or more conditions associated with an external breathing therapy delivered to the patient. The device may monitor therapy parameters including therapy effectiveness, impact of the therapy on the patient, therapy usage, compliance with a prescribed usage, therapy interactions, and/or other parameters.

27 Claims, 31 Drawing Sheets

U.S. PATENT DOCUMENTS

| | | |
|---|---|---|
| 5,334,222 A | 8/1994 | Salo et al. |
| 5,353,788 A | 10/1994 | Miles |
| 5,360,442 A | 11/1994 | Dahl et al. |
| 5,366,496 A | 11/1994 | Dahl et al. |
| 5,376,476 A | 12/1994 | Eylon |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,411,031 A | 5/1995 | Yomtov |
| 5,483,969 A | 1/1996 | Testerman et al. |
| 5,485,851 A | 1/1996 | Erickson |
| 5,517,983 A | 5/1996 | Deighan et al. |
| 5,522,862 A | 6/1996 | Testerman et al. |
| 5,540,727 A | 7/1996 | Tockman et al. |
| 5,545,186 A | 8/1996 | Olson et al. |
| 5,545,202 A | 8/1996 | Dahl et al. |
| 5,549,655 A | 8/1996 | Erickson |
| 5,603,732 A | 2/1997 | Dahl et al. |
| 5,715,812 A | 2/1998 | Deighan et al. |
| 5,720,771 A * | 2/1998 | Snell ........................... 607/60 |
| 5,814,087 A | 9/1998 | Renirie |
| 5,836,987 A | 11/1998 | Baumann et al. |
| 5,844,680 A | 12/1998 | Sperling |
| 5,855,593 A | 1/1999 | Olson et al. |
| 5,861,011 A | 1/1999 | Stoop |
| 5,891,023 A | 4/1999 | Lynn |
| 5,911,218 A | 6/1999 | DiMarco |
| 5,916,243 A | 6/1999 | KenKnight et al. |
| 5,957,861 A * | 9/1999 | Combs et al. ............... 600/547 |
| 5,964,778 A | 10/1999 | Fugoso et al. |
| 5,974,340 A | 10/1999 | Kadhiresan |
| 6,026,320 A | 2/2000 | Carlson et al. |
| 6,044,298 A | 3/2000 | Salo et al. |
| 6,055,454 A | 4/2000 | Heemels |
| 6,064,910 A | 5/2000 | Andersson et al. |
| 6,076,015 A | 6/2000 | Hartley et al. |
| 6,091,973 A | 7/2000 | Colla et al. |
| 6,099,479 A | 8/2000 | Christopherson et al. |
| 6,120,441 A | 9/2000 | Griebel |
| 6,126,611 A | 10/2000 | Bourgeois et al. |
| 6,128,534 A | 10/2000 | Park et al. |
| 6,132,384 A | 10/2000 | Christopherson et al. |
| 6,141,581 A | 10/2000 | Olson et al. |
| 6,141,590 A | 10/2000 | Renirie et al. |
| 6,221,011 B1 | 4/2001 | Bardy |
| 6,240,316 B1 | 5/2001 | Richmond et al. |
| 6,251,126 B1 | 6/2001 | Ottenhoff et al. |
| 6,259,947 B1 | 7/2001 | Olson et al. |
| 6,269,269 B1 | 7/2001 | Ottenhoff et al. |
| 6,270,457 B1 | 8/2001 | Bardy |
| 6,275,727 B1 | 8/2001 | Hopper et al. |
| 6,277,072 B1 | 8/2001 | Bardy |
| 6,280,380 B1 | 8/2001 | Bardy |
| 6,285,907 B1 | 9/2001 | Kramer et al. |
| 6,312,378 B1 | 11/2001 | Bardy |
| 6,331,536 B1 | 12/2001 | Radulovacki et al. |
| 6,336,903 B1 | 1/2002 | Bardy |
| 6,351,669 B1 | 2/2002 | Harley et al. |
| 6,353,759 B1 | 3/2002 | Harley et al. |
| 6,358,203 B2 | 3/2002 | Bardy |
| 6,361,522 B1 | 3/2002 | Scheiner et al. |
| 6,363,270 B1 | 3/2002 | Colla et al. |
| 6,368,284 B1 | 4/2002 | Bardy |
| 6,371,922 B1 | 4/2002 | Baumann et al. |
| 6,398,728 B1 | 6/2002 | Bardy |
| 6,411,848 B2 | 6/2002 | Kramer et al. |
| 6,415,183 B1 | 7/2002 | Scheiner et al. |
| 6,424,865 B1 | 7/2002 | Ding |
| 6,438,410 B2 | 8/2002 | Hsu et al. |
| 6,440,066 B1 | 8/2002 | Bardy |
| 6,449,503 B1 | 9/2002 | Hsu |
| 6,454,719 B1 * | 9/2002 | Greenhut ..................... 600/484 |
| 6,459,929 B1 | 10/2002 | Hopper et al. |
| 6,480,733 B1 | 11/2002 | Turcott |
| 6,487,443 B2 | 11/2002 | Olson et al. |
| 6,542,775 B2 | 4/2003 | Ding et al. |
| 6,574,507 B1 | 6/2003 | Bonnet |
| 6,589,188 B1 | 7/2003 | Street et al. |
| 6,597,951 B2 | 7/2003 | Kramer et al. |
| 6,641,542 B2 | 11/2003 | Cho et al. |
| 6,741,885 B1 * | 5/2004 | Park et al. ................... 600/509 |
| 6,773,404 B2 | 8/2004 | Poezevera et al. |
| 7,025,730 B2 * | 4/2006 | Cho et al. .................... 600/529 |
| 7,062,308 B1 * | 6/2006 | Jackson ....................... 600/361 |
| 2002/0193685 A1 * | 12/2002 | Mate et al. ................... 600/424 |
| 2002/0193839 A1 | 12/2002 | Cho et al. |
| 2003/0023184 A1 | 1/2003 | Pitts-Crick et al. |
| 2003/0055461 A1 | 3/2003 | Girouard et al. |
| 2003/0100925 A1 | 5/2003 | Pape et al. |
| 2003/0153953 A1 | 8/2003 | Park et al. |
| 2003/0153954 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0195571 A1 | 10/2003 | Burnes et al. |
| 2003/0199945 A1 | 10/2003 | Ciulla |
| 2003/0204213 A1 | 10/2003 | Jensen et al. |
| 2004/0002742 A1 | 1/2004 | Florio |
| 2004/0030362 A1 | 2/2004 | Hill et al. |
| 2004/0088027 A1 * | 5/2004 | Burnes et al. ................ 607/60 |
| 2004/0138719 A1 * | 7/2004 | Cho et al. .................... 607/42 |
| 2005/0043644 A1 * | 2/2005 | Stahmann et al. ........... 600/529 |
| 2005/0043772 A1 * | 2/2005 | Stahmann et al. ............ 607/42 |

FOREIGN PATENT DOCUMENTS

WO 02/087696 11/2002

OTHER PUBLICATIONS

Garrigue et al., *Night Atrial Overdrive with DDD Pacing Results in a Significant Reduction of Sleep Apnea Episodes and QOL Improvement in Heart Failure Patients*, NASPE (2001).

Garrigue et al., *Benefit of Atrial Pacing in Sleep Apnea Syndrome*, 346 N. Engl. J. Med. 404-412 (2002). Abstract only.

Hilton et al., *Evaluation of Frequency and Time-frequency Spectral Analysis of Heart Rate Variability as a Diagnostic Marker of the Sleep Apnea Syndrome*, 37 Med. Biol. Eng. Comput. 760-769 (1999). Abstract only.

Jais et al., *Night Atrial Overdrive with DDD Pacing: a New Therapy for Sleep Apnea Syndrome*, NASPE (2000).

Javaheri et al., *Sleep Apnea in 81 Ambulatory Male Patients with Stable Heart Failure: Types and Their Prevalences, Consequences, and Presentations*, 97 Circulation 2154-2159 (1998).

Olusola et al., *Nightcap: Laboratory and home-based evaluation of a portable sleep monitor*, 32 Psychophysiology, 32-98 (1995). Abstract only.

Verrier et al., *Sleep, dreams, and sudden death: the case for sleep as an autonomic stress test for the heart*, 31 Cardiovascular Research 181-211 (1996).

Verrier et al., *Sleep Related Cardiovascular Risk: New Home-Based Monitoring Technology for Improved Diagnosis and Therapy*, 2 A.N. E. 158-175 (1997).

Roche et al., *Screening of Obstructive Sleep Apnea Syndrome by Heart Rate Variability Analysis*, 100 Circulation 1411-1455 (1999).

Shahrokh, *A Mechanism of Central Sleep Apnea In Patients With Heart Failure*, 341 N. Engl. J. Med. 949-954 (1999). Abstract only.

Vanninen et al., *Cardiac Sympathovagal Balance During Sleep Apnea Episodes*, 16 Clin. Physiol. 209-216 (1996). Abstract only.

Waldemark et al., *Detection of Apnea using Short Window FFT Technique and Artificial Neural Network*, 3390 SPIE International Society of Optical Engineering 122-133 (1998).

Young et al., *The Occurrence of Sleep-Disordered Breathing Among Middle Aged Adults*, N. Engl. J. Med. 1230-1235 (1993). Abstract only.

* cited by examiner

METHODS AND SYSTEMS FOR IMPLANTABLY MONITORING EXTERNAL BREATHING THERAPY

This application claims the benefit of Provisional Patent Application Ser. No. 60/504,257, filed on Sep. 18, 2003, to which priority is claimed pursuant to 35 U.S.C. §119(e) and which is hereby incorporated herein by reference.

FIELD OF THE INVENTION

The present invention relates generally to therapy for sleep disordered breathing and, more particularly, to monitoring an external breathing treatment delivered to a patient.

BACKGROUND OF THE INVENTION

The human body functions through a number of interdependent physiological systems controlled through various mechanical, electrical, and chemical processes. The metabolic state of the body is constantly changing. For example, as exercise level increases, the body consumes more oxygen and gives off more carbon dioxide. The cardiac and pulmonary systems maintain appropriate blood gas levels by making adjustments that bring more oxygen into the system and dispel more carbon dioxide. The cardiovascular system transports blood gases to and from the body tissues. The respiration system, through the breathing mechanism, performs the function of exchanging these gases with the external environment. Together, the cardiac and respiration systems form a larger anatomical and functional unit denoted the cardiopulmonary system.

Diseases and disorders of the pulmonary system affect a large group of patients. Obstructive pulmonary diseases may be associated with a decrease in the total volume of exhaled air flow caused by a narrowing or blockage of the airways. Examples of obstructive pulmonary diseases include asthma, emphysema and bronchitis. Chronic obstructive pulmonary disease (COPD) refers to chronic lung diseases that result in blocked air flow in the lungs. Chronic obstructive pulmonary disease generally develops over many years, typically from exposure to cigarette smoke, pollution, or other irritants. Over time, the elasticity of the lung tissue is lost, the lung's air sacs may collapse, the lungs may become distended, partially clogged with mucus, and lose the ability to expand and contract normally. As the disease progresses, breathing becomes labored, and the patient grows progressively weaker. Many people with COPD concurrently have both emphysema and chronic bronchitis.

Restrictive pulmonary diseases involve a decrease in the total volume of air that the lungs are able to hold. Often the decrease in total lung volume is due to a decrease in the elasticity of the lungs themselves, or may be caused by a limitation in the expansion of the chest wall during inhalation. Restrictive pulmonary disease may be the result of scarring from pneumonia, tuberculosis, or sarcoidosis. A decrease in lung volume may be caused by various neurologic and muscular diseases affecting the neural signals and/or muscular strength of the chest wall and lungs. Examples of neurologic and/or muscular diseases that may affect lung volume include poliomyelitis and multiple sclerosis. Lung volume deficiencies may also be related to congenital or acquired deformities of the chest.

Pulmonary dysfunctions may also involve disorders of the pleural cavity and/or pulmonary vasculature. Pulmonary vasculature disorders may include pulmonary hypertension, pulmonary edema, and pulmonary embolism. Disorders of the pleural cavity include conditions such as pleural effusion, pneumothorax, and hemothorax, for example.

Pulmonary diseases may be caused by infectious agents such as viral and/or bacterial agents. Examples of infectious pulmonary diseases include pneumonia, tuberculosis, and bronchiectasis. Other non-infectious pulmonary diseases include lung cancer and adult respiratory distress syndrome (ARDS), for example.

Breathing disorders involving disrupted breathing rhythm, such as sleep apnea, hypopnea and periodic breathing, are respiratory system conditions that affect a significant percentage of patients between 30 and 60 years. Disordered breathing may be caused, for example, by an obstructed airway, or by derangement of the signals from the brain controlling respiration. Sleep disordered breathing is associated with excessive daytime sleepiness, systemic hypertension, increased risk of stroke, angina and myocardial infarction. Disordered breathing is related to congestive heart failure and can be particularly serious for patients concurrently suffering from cardiovascular deficiencies.

Various types of disordered breathing have been identified, including, apnea (interrupted breathing), hypopnea (shallow breathing), tachypnea (rapid breathing), hyperpnea (heavy breathing), and dyspnea (labored breathing). Combinations of the respiratory cycles described above may be observed, including, for example, periodic breathing and Cheyne-Stokes respiration (CSR). Cheyne-Stokes respiration is particularly prevalent among heart failure patients, and may contribute to the progression of heart failure.

Pulmonary diseases and disorders including those described herein have been treated using a variety of patient-external breathing therapy devices. Monitoring parameters associated with external breathing therapy provides an opportunity to provide feedback for enhanced therapy delivery. Effective approaches to monitoring and/or adjusting external breathing therapy are needed. The present invention fulfills these and other needs, and addresses other deficiencies of prior art implementations and techniques.

SUMMARY OF THE INVENTION

Embodiments of the invention are directed to methods and systems for monitoring therapy delivered to a patient. An embodiment of the invention involves a method for implantably monitoring a patient-external respiration therapy delivered to the patient. The method includes sensing one or more conditions associated with patient-external breathing therapy. The patient-external respiration therapy is monitored by an implantable device based on the sensed conditions.

In accordance with another embodiment of the invention, a medical system, includes a sensing system configured to sense conditions associated with a patient-external breathing therapy. The system also includes an implantable monitoring device, coupled to the sensing system. The implantable monitoring device is configured to monitor the patient-external breathing therapy based on the one or more sensed conditions.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
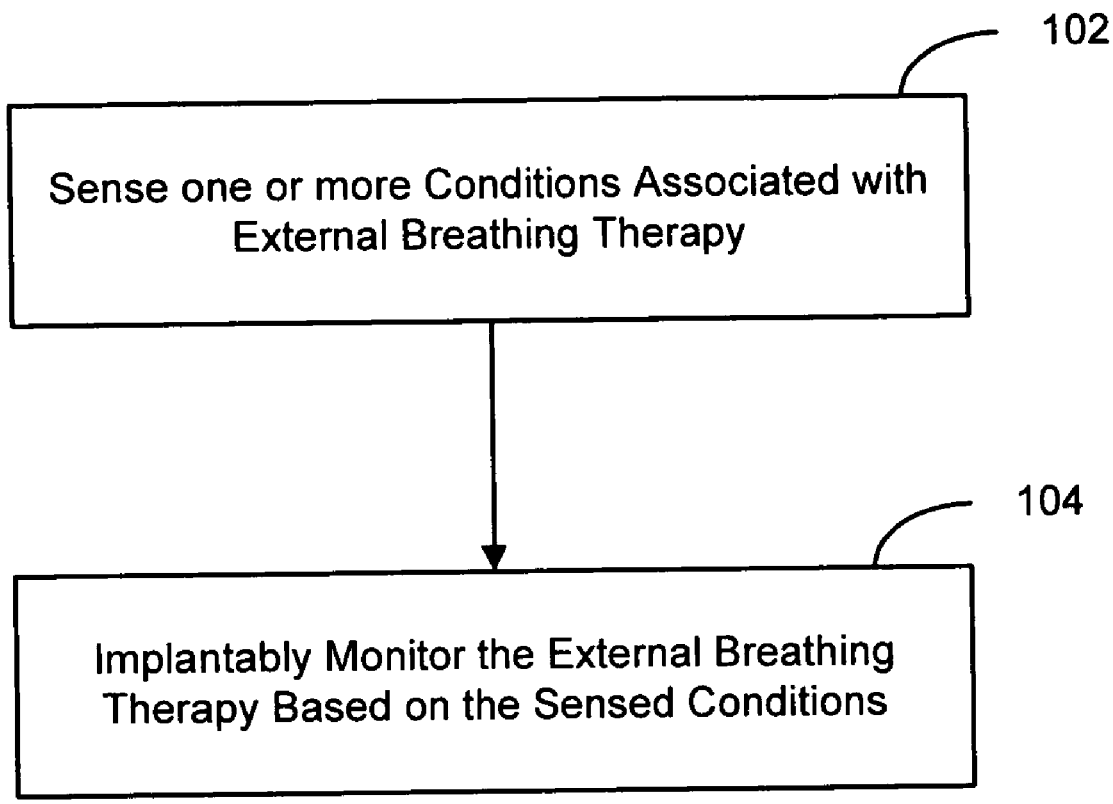
FIGS. 1A-1E are flowcharts illustrating methods of implantably monitoring an externally delivered breathing therapy in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

Breathing disorders may be more effectively monitored and/or treated using a coordinated approach. Various embodiments of the invention are implemented using medical systems employing two or more patient-external and/or patient-internal medical devices. The medical devices may communicate or otherwise operate in concert to provide more comprehensive patient monitoring for external breathing therapy.

A number of disorders are treated using external breathing therapy devices. For example, rhythm related breathing disorders such as sleep apnea, hypopnea may be treated with a positive airway pressure device. Asthma may be treated with a nebulizer. Various diseases affecting the pulmonary system may be treated with gas or oxygen therapy. Embodiments of the invention are directed to methods and systems utilizing an implantable device to monitor parameters associated with an external breathing therapy delivered to the patient. External breathing therapy may be delivered by various types of patient-external respiratory therapy devices, including, for example, nebulizers, respirators, ventilators, external gas therapy devices and/or positive airway pressure devices.

A typical continuous positive airway pressure (CPAP) device delivers air pressure through a nasal mask worn by the patient. The application of continuous positive airway pressure keeps the patient's throat open, reducing or eliminating the obstruction causing apnea. Positive airway pressure devices may be used to provide a variety of respiration therapies, including, for example, continuous positive airway pressure (CPAP), bi-level positive airway pressure (bi-level PAP), proportional positive airway pressure (PPAP), auto-titrating positive airway pressure, ventilation, gas or oxygen therapies. Some positive airway pressure devices may also be configured to provide both positive and negative pressure, such that negative pressure is selectively used (and de-activated) when necessary, such as when treating Cheyne-Stokes breathing, for example. The term xPAP will be used herein as a generic term for any device using forms of positive airway pressure (and negative pressure when necessary), whether continuous or otherwise.

The parameters monitored by the monitoring system may include therapy effectiveness, impact of the therapy on the patient, therapy usage, compliance with a prescribed usage and/or therapy interactions, for example. In various embodiments described herein, sensors coupled to the implantable monitoring device sense conditions used to monitor therapy parameters. For example, the sensed conditions may be used to evaluate the effectiveness of the breathing therapy the impact of the therapy on the patient and/or therapy interactions between the external breathing therapy and other therapies delivered to the patient. The external breathing therapy may be adjusted to enhance therapy effectiveness, to reduce an impact of the therapy and/or to reduce therapy interactions. The implantable device may monitor the patient's use of the external breathing therapy and/or compliance with a prescribed usage of the breathing therapy, for example.

The implantable device may transmit information about the sensed conditions and/or the monitored parameters to the external breathing therapy device. The information may be used by the external breathing therapy device to automatically adjust the breathing therapy delivered to the patient. The information may be transmitted, either by the implantable device, or by the external breathing therapy device, to a patient management system. Advanced patient management (APM) systems involve a system of medical devices that are accessible through various communications technologies. Medical information may be transmitted to a remote patient management server from the various medical devices. The medical information may be analyzed and used to diagnose and/or monitor disease progression, to determine appropriate therapies for the patient, and/or for other medical purposes.

Information acquired by the monitoring device, including information associated with the sensed conditions and/or the parameters of the breathing therapy, may be evaluated to facilitate diagnosis and/or therapy adjustment. The information transmitted to the patient management system may be used for diagnostic purposes related to the breathing disorder affecting the patient, for example. The patient management system may adjust breathing therapy delivery based on the information. In one implementation, the patient management system transmits control signals to the breathing therapy device to adjust the breathing therapy. Further, the patient and/or the patient's physician may access the information through the patient management system.

FIGS. 1A-E are flowcharts illustrating methods related to implantably monitoring external breathing therapy in accordance with various embodiments of the invention. As illustrated in the flowchart of FIG. 1A, a method for monitoring external breathing treatment involves sensing 102 one or more conditions associated with patient-external breathing therapy and implantably monitoring 104 the patient-external breathing therapy based on the one or more sensed conditions. The sensed conditions are used to monitor one or more parameters of the patient-external breathing therapy, such as the patient's compliance with the external breathing therapy, the effectiveness of the external breathing therapy, the impact of the external breathing therapy on the patient, and/or other conditions. The parameters monitored by the implantable device, and the conditions sensed to monitor the breathing therapy parameters can be programmable. The implantable device may acquire information used to monitor the breathing therapy parameters continuously or during selected periods of time. For example, if the patient suffers from sleep disordered breathing, the implantable device may acquire information associated with the breathing therapy after detecting that the patient is asleep. Information acquired by the implantable device based on the sensed conditions may be stored, displayed, printed, trended and/or transmitted from the implantable device to another device, such as a patient-external device, implantable device, therapy device, device programmer, and/or advanced patient management server. Information associated with the monitored parameters, e.g., therapy usage, may be stored, displayed, printed, trended, and/or transmitted from the implantable device to another device.

Figure 1B:
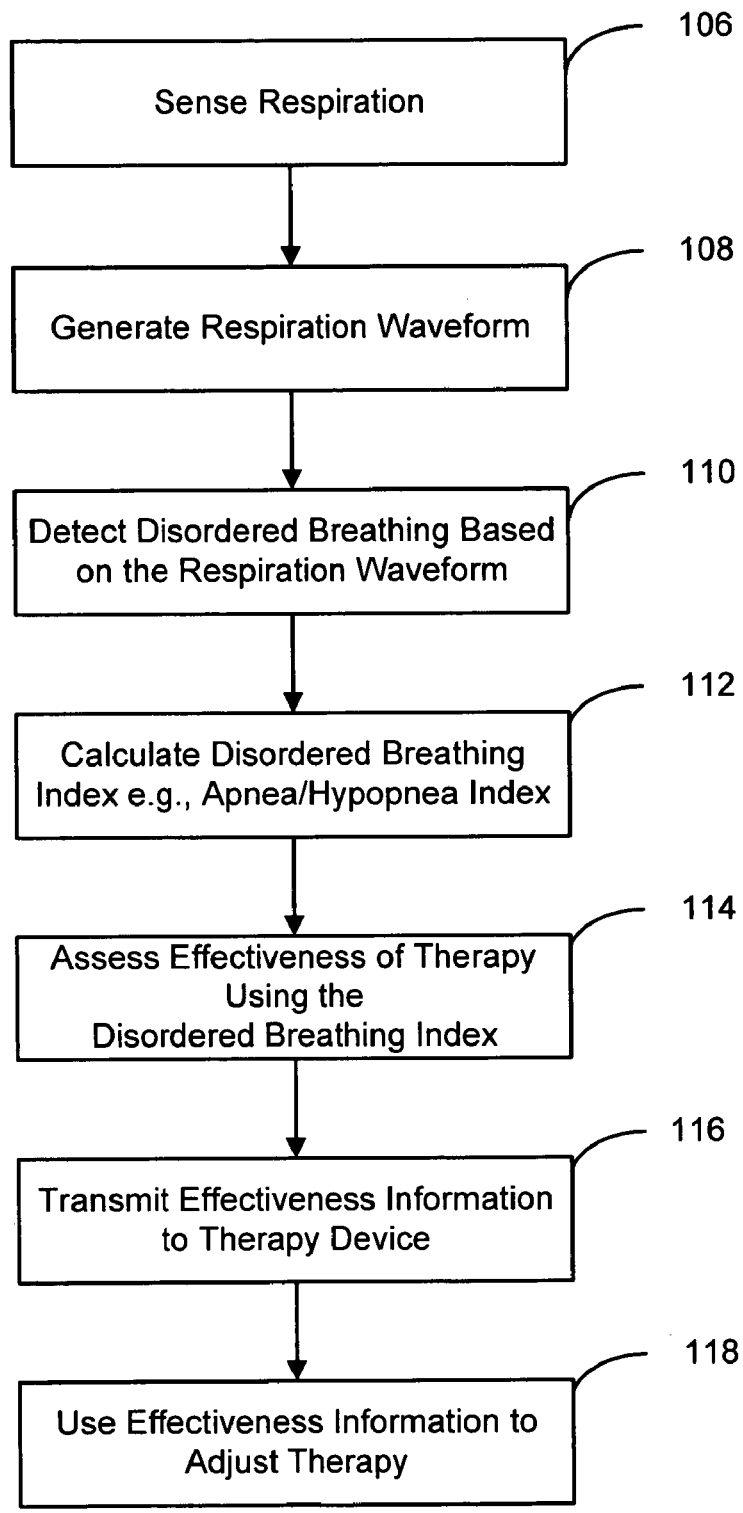

FIG. 1B is a flowchart illustrating a method for monitoring the effectiveness of an externally delivered breathing therapy using an implantable device. The patient's respiration is sensed 106 and a respiration waveform is generated 108. The sensed respiration waveform is used by the implantable device to detect 110 disordered breathing events. An apnea/hypopnea index (AHI) is calculated 112 based on the detected disordered breathing events. The AHI is used to assess the effectiveness 114 of the breathing treatment. A lower AHI may indicate a more effective breathing treatment than a relatively higher AHI, for example. The therapy effectiveness information may be transmitted 116 to the external breathing therapy device and/or to an APM server. The therapy effectiveness data may be used 118 by the external breathing therapy device, or by the APM device, for example, to adjust the external breathing therapy. The therapy adjustment may be performed automatically by the APM or by the external breathing therapy device. The therapy adjustment may be performed manually by the patient's physician based on the effectiveness information.

External breathing therapy may be inconvenient to use and uncomfortable to the patient. As a result, the patient may limit the use of the therapy. For example, if the use of the breathing therapy interferes with the patient's ability to sleep, the patient may stop using the breathing therapy, or may use the breathing therapy infrequently. The patient may not keep track of how frequently he or she uses the breathing therapy and may not be able to accurately report breathing therapy compliance to the physician.

Figure 1C:
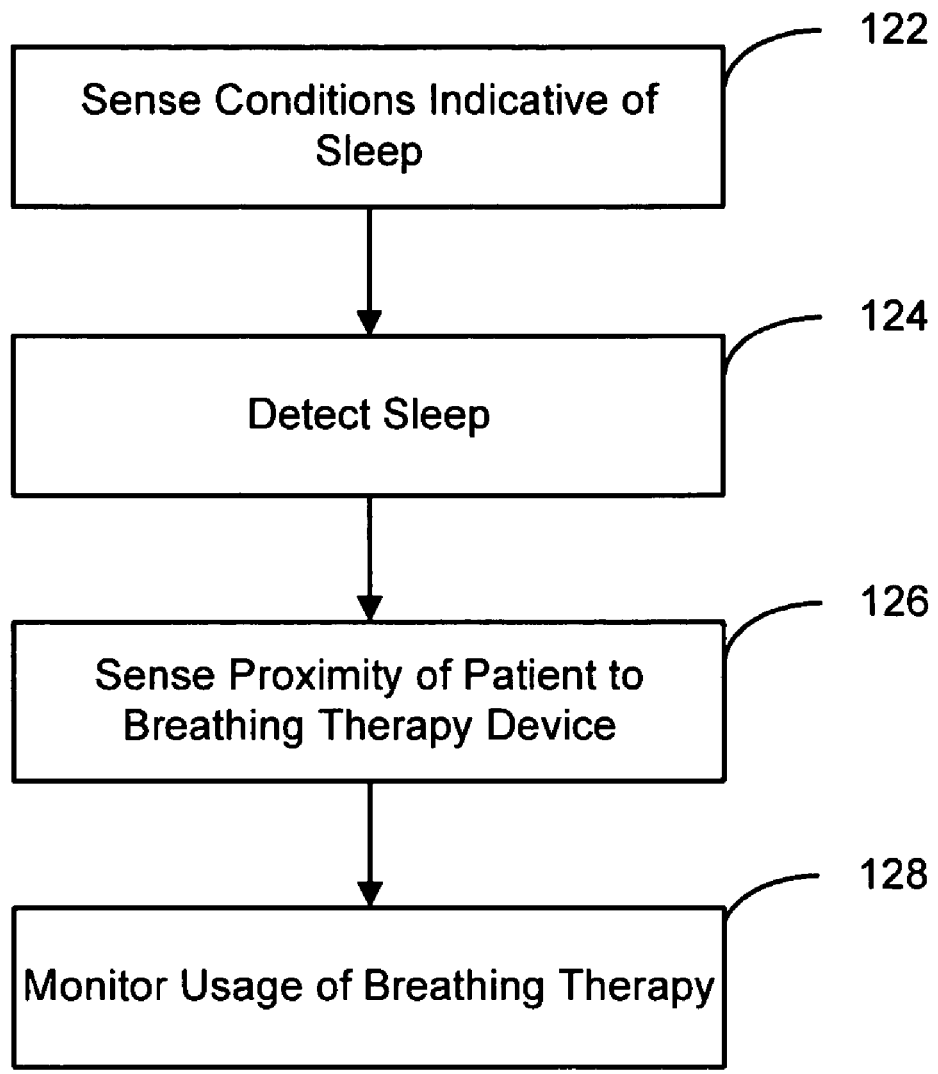

FIG. 1C is a flowchart of a method for implantably monitoring a patient's usage of the external breathing therapy. In this example, usage of an external breathing therapy for sleep disordered breathing is determined based on the patient's proximity to the external breathing therapy device during sleep. As illustrated in FIG. 1C, one or more conditions indicative of sleep may be sensed 122. The implantable device detects 124 sleep based on the sensed sleep-related conditions. The proximity of the patient to the external breathing therapy device is sensed 126.

The proximity of the patient to the external breathing therapy device may be determined using a transmitter coupled to the external breathing therapy device and a receiver in the implantable monitoring device. If the patient is near the external breathing therapy device, the receiver receives a signal broadcast by the transmitter. The transmitter may be located on a bedside unit of the external breathing therapy device, or on the respiratory mask of the external breathing therapy device, for example.

The implantable device monitors 128 the patient's usage of external breathing therapy based on the proximity of the patient to the external breathing therapy device during sleep. Other methods of determining patient usage of the external breathing therapy device may also be implemented. For example, the morphology of the patient's respiration waveform during external breathing therapy may be detectably different from the patient's respiration waveform when therapy is not being delivered. The implantable device may sense the patient's respiration and monitor usage of the external breathing therapy device based on evaluation of the patient's respiration waveform.

The implantable device may monitor patient compliance with respect to a prescribed breathing therapy. The implantable device may transmit information related to the patient compliance to an external device, such as a patient management device accessible to the patient and/or the patient's physician. The information may be used to alert to the patient and/or to the patient's physician when the patient's compliance with the prescribed breathing therapy drops below a threshold level.

Figure 1D:
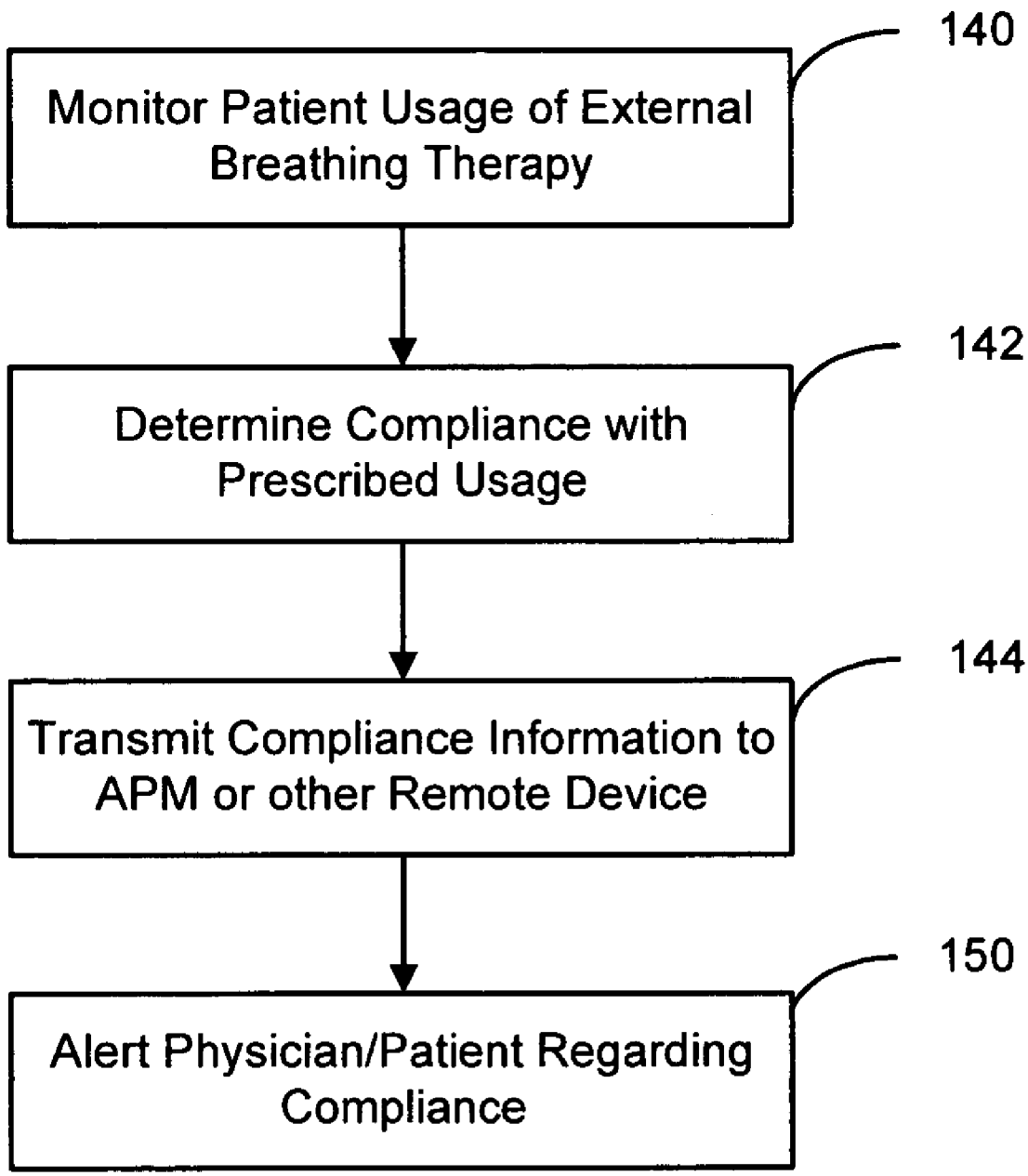

FIG. 1D is a flowchart of a method for implantably monitoring patient compliance with a prescribed breathing therapy in accordance with embodiments of the invention. Breathing therapy is delivered to the patient using a patient external device. The patient's use of externally delivered breathing therapy is monitored 140 using an implantable device.

In one implementation, the implantable device may monitor patient use of the breathing therapy may by sensing the proximity of the patient to the breathing therapy unit. According to this approach, if the patient is within a selected proximity range of the patient-external breathing therapy unit, then the patient is assumed to be using the breathing therapy.

Figure 1E:
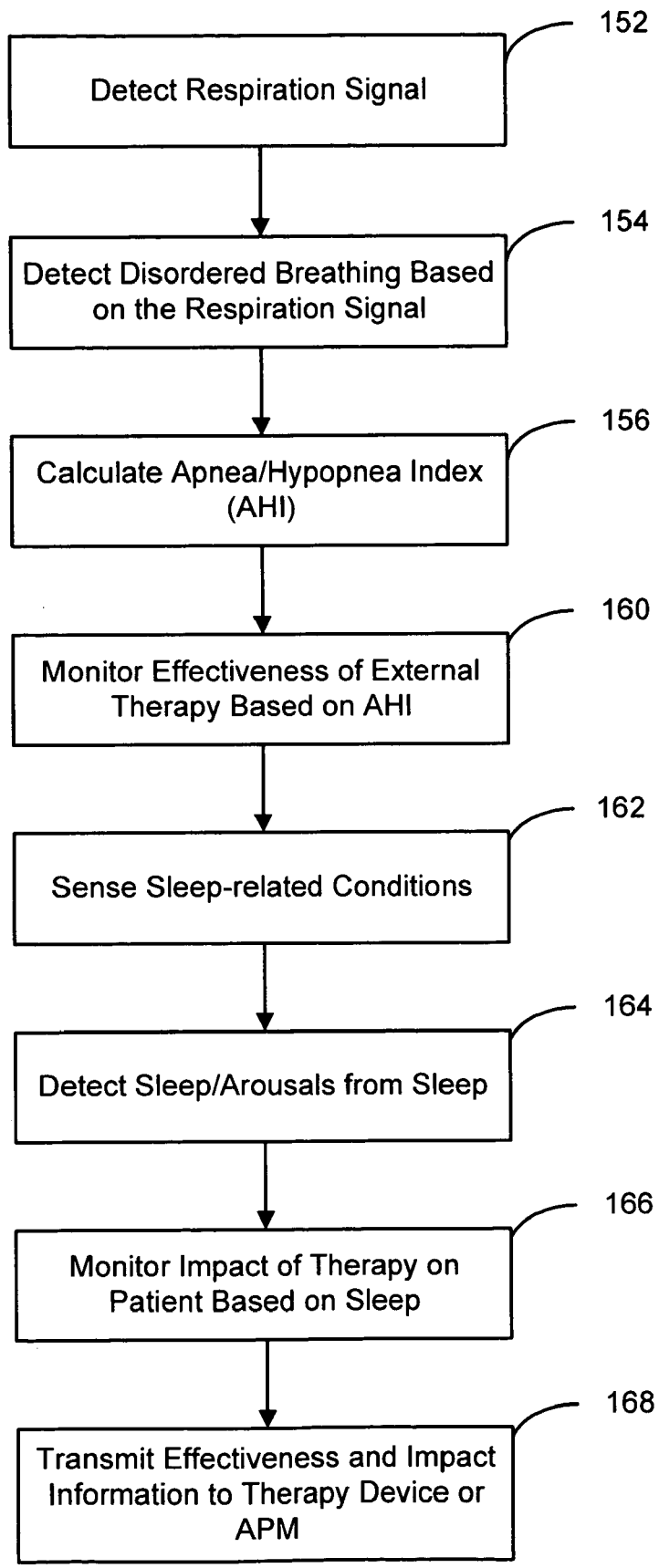
Figure 1F:
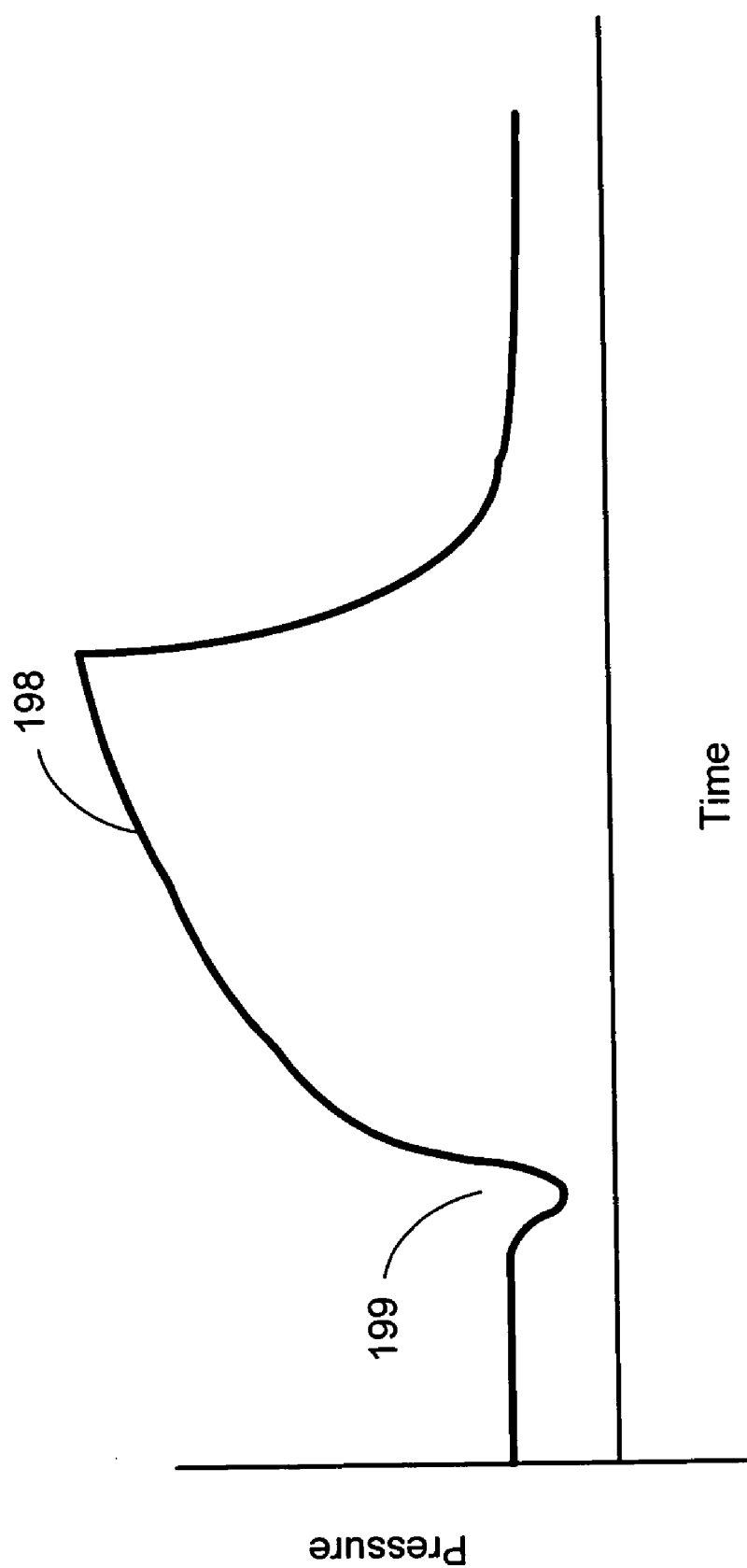
FIG. 1F is a graph of respiratory pressure with respect to time illustrating a respiratory pressure notch observable when a patient is using a breathing therapy device.

Another approach to monitoring patient compliance with breathing therapy involves analyzing the respiratory waveform of the patient. For example, the implantable device may sense the transthoracic impedance of the patient to determine the patient's respiratory waveform. The patient's use of the breathing therapy may be determined by detecting features of the respiratory waveform indicative of breathing therapy usage. In one scenario, use of the breathing therapy may be determined by comparing the morphology of a patient's respiratory waveform during therapy to the morphology of the patient's respiratory waveform without therapy. The patient's respiratory waveforms with and without therapy may be compared to detect features that indicate usage. For example, the patient may be determined to be using the breathing therapy if the patient's respiratory waveform exhibits a pressure notch indicative of flow controlled breathing therapy usage. FIG. 1F illustrates a graph of respiratory pressure 198 with respect to time. The notch 199 on the pressure graph indicates that the patient is using the breathing therapy device.

In another example, patient compliance with the prescribed breathing therapy may be determined based on night to night changes in therapy effectiveness. For example, if the therapy effectiveness stays constant or changes slowly over the course of several nights, it may be determined that the patient is using the breathing therapy as prescribed. Usage of the therapy may be determined by using a baseline of therapy effectiveness developed over several nights. If the therapy effectiveness drops significantly from the baseline, then the patient may have stopped using the therapy device.

Returning to FIG. 1D, information related to the patient's use of the breathing therapy may be collected and/or evaluated by the implantable device, including, for example, the times the patient used the breathing therapy, the duration of the usage, the frequency of usage, and/or other information.

The patient's compliance with a prescribed breathing therapy may be determined 142 by comparing the actual use to the prescribed use. In one scenario, the compliance determination may be performed by the implantable device. In another scenario, information related to the patient use of the breathing therapy may be transmitted 144 to a remote device, such as the breathing therapy device or a patient management device, where the analysis is performed. The patient and/or the patient's physician may be alerted 150 to the patient's compliance with the breathing therapy. In one scenario, the patient and/or the patient's physician may be alerted if the patient's compliance decreases below a threshold value. The patient may be reminded to use the breathing therapy. If patient compliance is low, the physician and/or the patient may adjust the therapy to increase breathing therapy compliance.

In accordance with one embodiment, the breathing therapy may be implantably monitored for therapy effectiveness and impact to the patient. The flowchart of FIG. 1E illustrates an example method involving the use of a monitoring device configured as a component of an implantable cardiac device to monitor breathing therapy delivered by a continuous positive airway pressure (CPAP) device. In this example, therapy for sleep disordered breathing is delivered to the patient using a continuous positive airway pressure (CPAP) device. The effectiveness of the breathing therapy and the impact of the therapy on the patient are monitored by an implantable cardiac device.

Sensors coupled to the implantable monitoring device sense one or more patient conditions related to therapy effectiveness. For example, the respiration of the patient may be sensed 152 and the monitoring device may detect 154 disordered breathing episodes based on the respiration signal. The monitoring device may monitor therapy effectiveness by monitoring the severity, frequency and/or duration of sleep disordered breathing episodes experienced by the patient. In one implementation, the monitoring device may calculate 156 an apnea/hypopnea index (AHI) and/or a percent time in periodic breathing (% PB) indicative of the frequency of disordered breathing episodes. The effectiveness of the CPAP therapy may be monitored 160 based on the calculated indices. If the AHI and/or % PB are relatively low, the breathing therapy may be determined to be effective.

A CPAP device typically includes a respiratory mask, e.g., a nasal or facial mask, worn by the patient to facilitate delivery of air or other gas to the patient's airway. The respiratory mask may be inconvenient and/or uncomfortable for the patient to wear and may keep the patient awake. Further, delivery of positive airway pressure may disturb the patient, inhibit sleep, and/or cause the patient to arouse frequently. Sleep disturbances may be more frequent and/or severe if the CPAP therapy pressure is too high. Information about these side effects of the breathing therapy may be helpful in tailoring a therapy regimen for the patient. The monitoring device may monitor the impact of the CPAP therapy on the patient based on one or more sensed conditions indicative of the impact of the therapy on the patient.

In one example, the one or more sensed conditions 162 relate to sleep and may be used to detect 164 sleep and/or arousals from sleep. The monitoring unit implemented in an implantable cardiac device may monitor 166 the impact of the CPAP therapy on the patient by monitoring the patient's sleep. For example, the monitoring unit may monitor the total time the patient spends sleeping, the number of arousals experienced by the patient in one night, and/or the depth of the arousals. In one implementation the cardiac device may calculate the number of arousals experienced by the patient per hour (A/h).

The therapy effectiveness and impact information may be transmitted 168 to the CPAP device and/or an APM server. The information may be used to automatically or manually adjust the therapy delivered to the patient. For example, if the AHI is high, the breathing therapy pressure may be adjusted upward to provide a more effective therapy. If the patient experiences an arousal rate, e.g., A/h, greater than a threshold without experiencing sleep disordered breathing episodes, the therapy may be determined to be too aggressive. The breathing therapy pressure may be adjusted downward to provide a disordered breathing therapy that is more comfortable to the patient and allows the patient to sleep with fewer interruptions.

Figure 2:
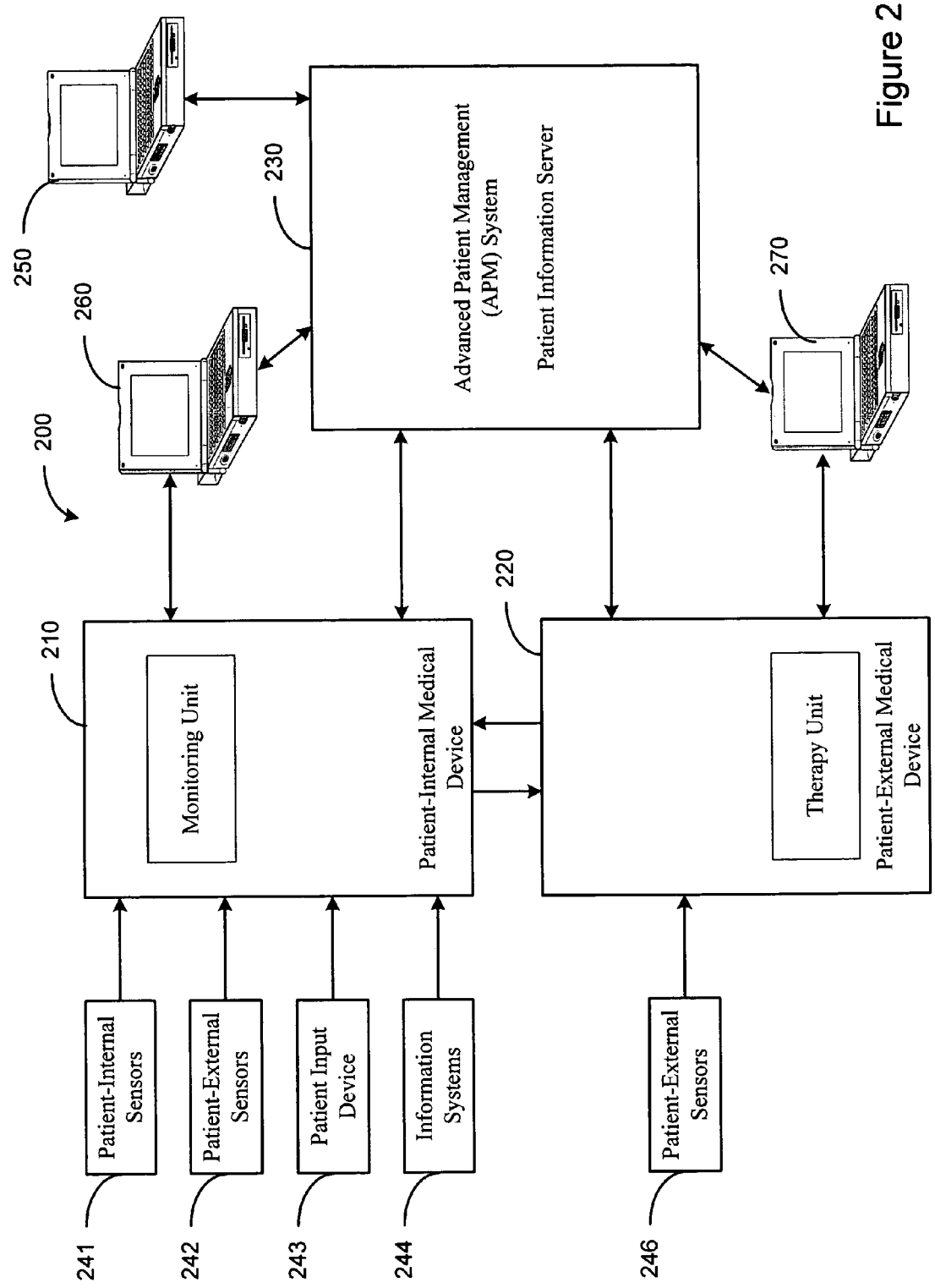
FIG. 2 is a block diagram of a medical system that may be used to provide patient monitoring and external breathing therapy in accordance with embodiments of the invention.

FIG. 2 is a block diagram of a medical system 200 that may be used to implement coordinated patient monitoring and therapy in accordance with embodiments of the invention. The medical system 200 may include, for example, a patient-internal monitoring device 210 and a patient-external breathing therapy device 220.

The patient-internal monitoring device 210 may be a fully or partially implantable device that monitors breathing therapy delivered to the patient by the therapy device 220. The patient-external breathing therapy device 220 is external to the patient (i.e., not invasively implanted within the patient's body). The patient-external therapy device 220 may be positioned on the patient, near the patient, or in any location external to the patient. It is understood that a portion of a patient-external therapy device 220 may be positioned within an orifice of the body, such as the nasal cavity or mouth, yet can be considered external to the patient (e.g., mouth pieces/appliances, tubes/appliances for nostrils, or temperature sensors positioned in the ear canal).

The patient-internal device 210 may be coupled to one or more sensors 241, 242, patient input devices 243 and/or other information acquisition devices 244. The sensors 241, 242, patient input devices 243, and/or other information acquisition devices 244 may be employed to detect conditions relevant to the breathing therapy delivered by the patient-external therapy device 220. The patient-external device 220 may also be coupled to one or more sensors 246 and/or other information devices. Information from the sensors 246, e.g., flow sensors, pressure sensors, and/or other input devices, e.g., patient input devices and/or network based information servers coupled to the patient-external device 220 may be used by the therapy device 220 to adjust the therapy delivered by the patient external device 220. In some implementations, sensed or detected information acquired by the patient external device 220 may be transmitted from the patient-external device 220 to the patient-internal device 210. The transmitted information may be used in connection with the monitoring functions of the patient internal device 210.

In one implementation, the patient-internal device 210 is coupled to one or more patient-internal sensors 241 that are fully or partially implantable within the patient. The patient-internal device 210 may also be coupled to patient-external sensors 242 positioned on, near, or in a remote location with respect to the patient. The patient-internal 241 and patient-external 242 sensors may be used to sense various parameters, such as physiological or environmental parameters related to the breathing therapy delivered by the patient-external therapy device.

The patient-internal sensors 241 may be coupled to the patient-internal medical device 210 through internal leads. For example, an internal endocardial lead system may be used to couple cardiac electrodes for sensing cardiac electrical activity to an implantable pacemaker or other cardiac device that includes a monitoring unit as described herein. Alternatively one or more patient-internal sensors 241 may be equipped with transceiver circuitry to support wireless communication between the one or more patient-internal sensors 241 and the patient-internal medical device 210. Patient-external sensors 242 are preferably wirelessly coupled to the patient-internal device 210.

The patient-internal device 210 may be coupled to one or more patient-input devices 243. The patient-input devices 243 allow the manual transfer of information to the patient-internal device 210. The patient-input devices 243 may be particularly useful for allowing the patient to input information concerning patient perceptions, such as how well the patient feels, and information such as patient smoking, drug use, or other activities that are not automatically sensed or detected by the medical devices 210.

The patient-internal device 210 may be connected to one or more information systems 244, for example, a database or information server that provides information useful in connection with the monitoring functions of the patient-internal device 210. For example, the patient-internal device 210 may be coupled through a network such as the internet to a information system server that provides information about environmental conditions affecting the patient, e.g., the pollution index for the patient's location. Internal sensors, external sensors, patient input devices and/or information systems similar to those described above may also be coupled to the patient-external therapy device.

In one embodiment, the patient-internal device 210 and the patient-external therapy device 220 may communicate through a wireless link between the devices 210, 220. For example, the patient-internal and patient-external devices 210, 220 may be coupled through a short-range radio link, such as Bluetooth or a proprietary wireless link. The communications link may facilitate unidirectional or bi-directional communication between the patient-internal 210 and patient-external 220 medical devices. Data and/or control signals may be transmitted between the patient-internal 210 and patient-external 220 medical devices to coordinate or control the functions of the medical devices 210, 220.

In another embodiment of the invention, the patient-internal and patient-external medical devices 210, 220 may be used within the structure of an advanced patient management system. Advanced patient management systems involve a system of medical devices that are accessible through various communications technologies. For example, patient data may be downloaded from one or more of the medical devices in the system periodically or on command, and stored at a patient information server. The physician and/or the patient may communicate with the medical devices and the patient information server, for example, to acquire patient data or to initiate, terminate or modify therapy.

In the implementation illustrated in FIG. 2, the patient-internal medical device 210 and the patient-external medical device 220 may be coupled through wireless or wired communication links to a patient information server that is part of an advanced patient management (APM) system 230. The APM patient information server 230 may be used to download and store data collected by the patient-internal and patient-external medical devices 210, 220. In one implementation, the patient internal device 210 and/or the patient-external device 220 may be communicatively coupled to device programmers 260, 270. The programmer 260 may provide indirect communication between the patient internal device 210 and the patient information server 230. The programmer 270 may provide indirect communication between the patient external device 220 and the patient information server 230.

The data stored on the APM patient information server 230 may be accessible by the patient and/or the patient's physician through terminals 250, e.g., remote computers located in the patient's home or the physician's office. The APM patient information server 230 may be communicate with one or more of the patient-internal and patient-external medical devices 210, 220 to effect remote control of the monitoring, diagnosis, and/or therapy functions of the medical devices 210, 220.

In one scenario, the patient's physician may access patient data transmitted from the monitoring device 210 to the APM patient information server 230. After evaluation of the collected information, the patient's physician may communicate with the patient-external therapy device 220 through the APM system 230 to initiate, terminate, or modify the therapy functions of the patient-external therapy device 220. Systems and methods involving advanced patient management techniques are further described in U.S. Pat. Nos. 6,336,903, 6,312,378, 6,270,457, and 6,398,728 which are incorporated herein by reference.

In one implementation, the patient-internal and patient-external medical devices 210, 220 may not communicate directly, but may communicate indirectly through the APM system 230. In this embodiment, the APM system 230 may operate as an intermediary between two or more of the medical devices 210, 220. For example, information collected by the patient-internal medical device 210 may be transferred from the patient-internal medical device 210 to the APM system 230. The APM system 230 may transfer the collected information to the patient-external therapy device 220.

Figure 3:
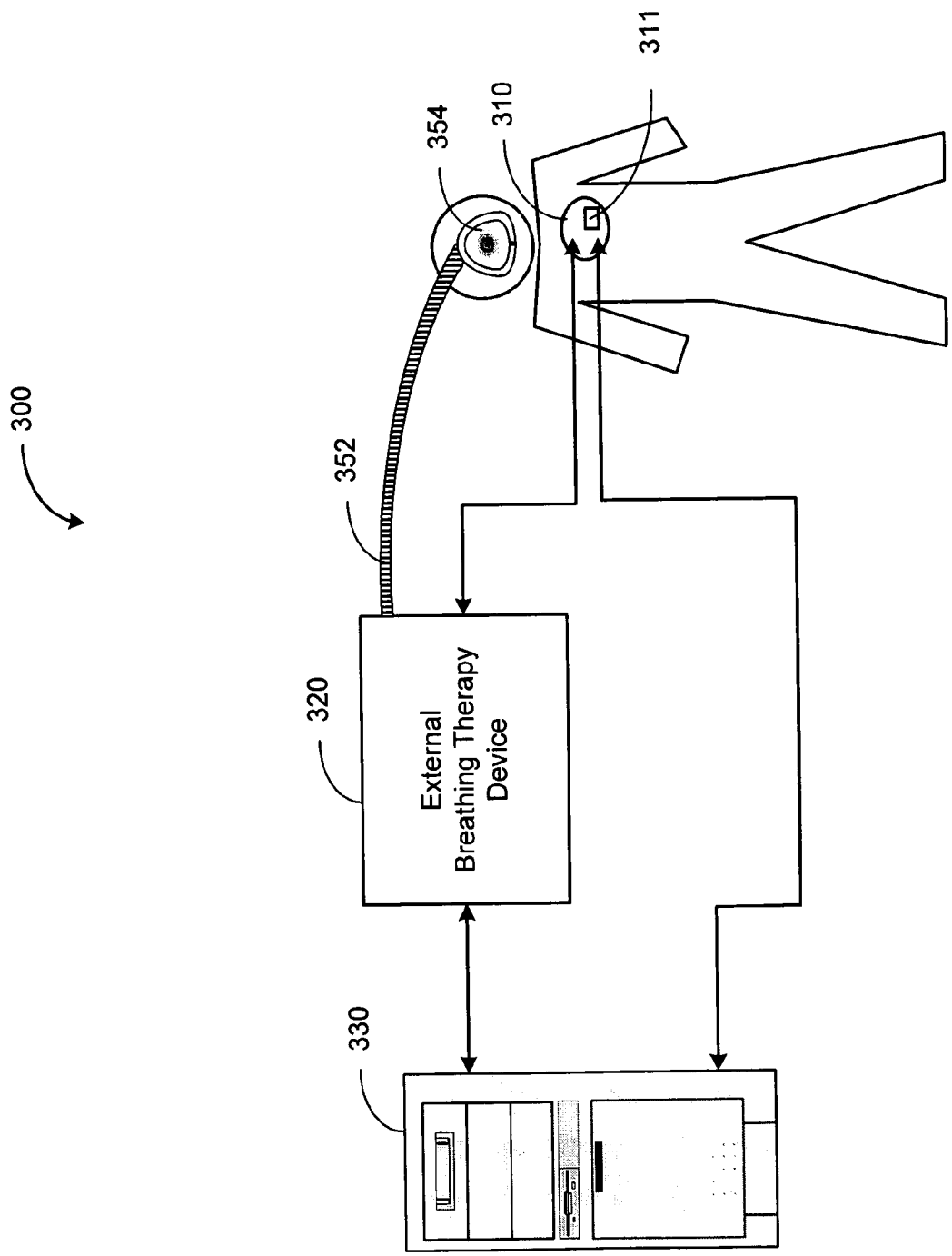
FIG. 3 illustrates a medical system including an implantable cardiac rhythm management device that may be used to monitor parameters of a breathing therapy delivered by a patient-external respiration therapy device in accordance with an embodiment of the invention.

FIG. 3 illustrates a block diagram of medical system 300 that may be used to implantably monitor breathing therapy delivered by a patient-external device in accordance with an embodiment of the invention. In this example, the medical system 300 includes an implantable cardiac rhythm management (CRM) device 310 incorporating a monitoring unit 311 that monitors one or more parameters of breathing therapy delivered by a breathing therapy device 320. In this configuration, the monitoring unit 311 within the implantable cardiac rhythm management device (CRM) 310 operates as the patient-internal medical device described in connection with FIG. 2. The CRM 310 incorporating the monitoring unit 311 may provide additional monitoring, diagnostic, and/or therapeutic functions to the patient.

The CRM 310 may be electrically coupled to the patient's heart through electrodes placed in, on, or about the heart. The cardiac electrodes may sense cardiac signals produced by the heart and/or provide therapy to one or more heart chambers. For example, the cardiac electrodes may deliver electrical stimulation to one or more heart chambers, and/or to one or multiple sites within the heart chambers. The CRM 310 may directly control delivery of one or more cardiac therapies, such as cardiac pacing, defibrillation, cardioversion, cardiac resynchronization, and/or other cardiac therapies, for example.

In the example illustrated in FIG. 3, the breathing therapy device 320 comprises a positive airway pressure device. Other types of external breathing therapy may be monitored by the monitoring unit 311, such as breathing treatment delivered by a nebulizer, respirator, ventilator or gas therapy device.

In the configuration illustrated in FIG. 3, the xPAP device 320 operates as a patient-external therapy device, as discussed in connection with FIG. 2. The xPAP device 320 develops a positive air pressure that is delivered to the patient's airway through tubing 352 and mask 354 connected to the xPAP device 320. Positive airway pressure devices are often used to treat disordered breathing, including central and/or obstructive disordered breathing types. In one configuration, for example, the positive airway pressure provided by the xPAP device 320 acts as a pneumatic splint keeping the patient's airway open and reducing the severity and/or number of occurrences of disordered breathing due to airway obstruction.

The monitoring unit 311 may monitor one or more parameters associated with the breathing therapy delivered by the xPAP device 320. The CRM 310 may communicate the information related to the breathing treatment to the xPAP device 320 through a wireless communications link, for example. Alternatively, or additionally, the CRM 310 and xPAP 320 devices may communicate with and/or through an APM system 330, as described above.

Figure 4A:
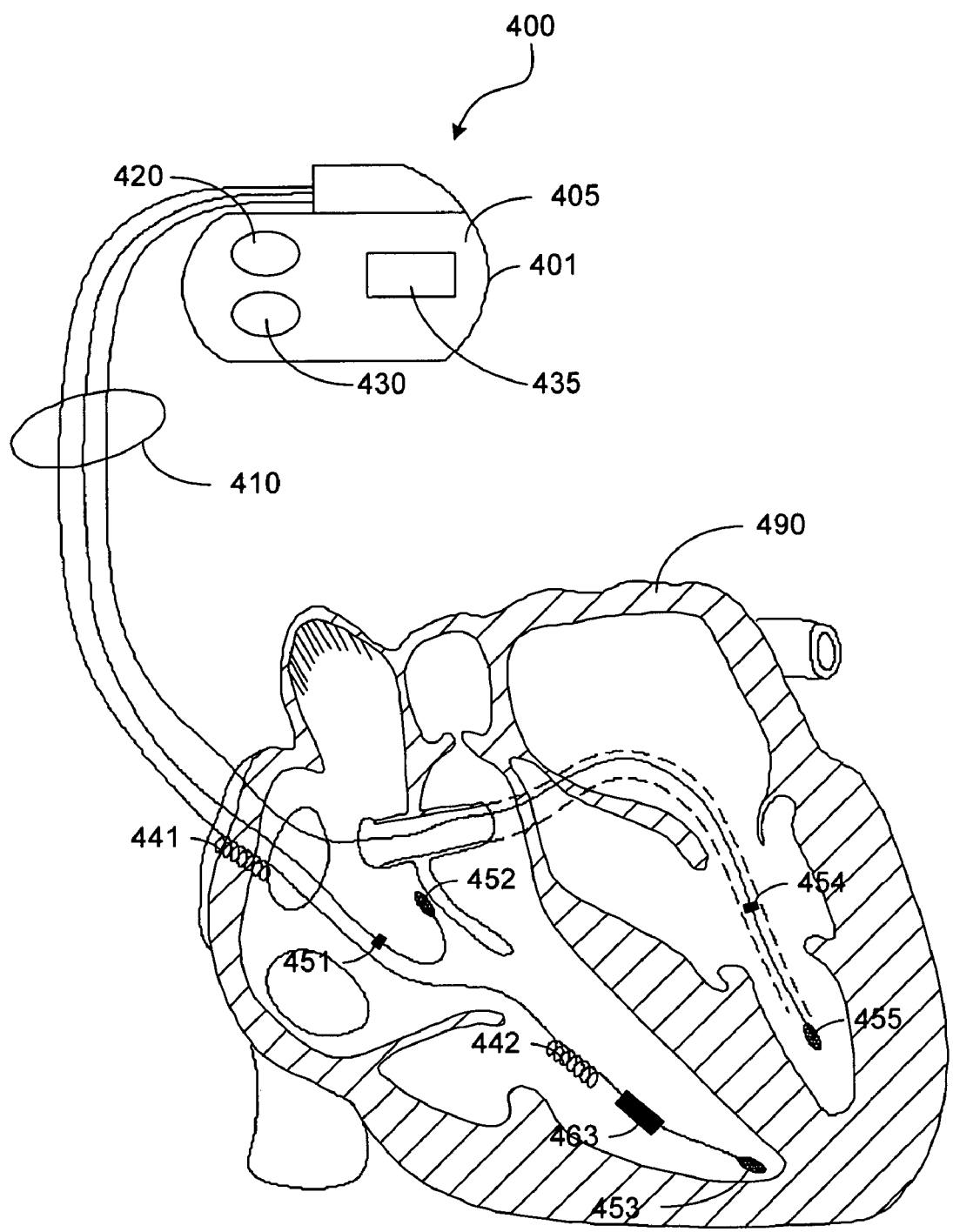
FIG. 4A is a partial view of an implantable medical device that may be used for coordinated patient monitoring, diagnosis, and/or therapy in accordance with an embodiment of the invention.

FIG. 4A is a partial view of an implantable device that may include circuitry for monitoring external breathing therapy 435 in accordance with embodiments of the invention. In this example, the implantable device comprises a cardiac rhythm management device (CRM) 400 including an implantable pulse generator 405 electrically and physically coupled to an intracardiac lead system 410. The external breathing therapy monitoring system may alternatively be implemented in a variety of implantable monitoring, diagnostic, and/or therapeutic devices, such as an implantable cardiac monitoring device, an implantable drug delivery device, or an implantable neurostimulation device, for example.

Portions of the intracardiac lead system 410 are inserted into the patient's heart 490. The intracardiac lead system 410 includes one or more electrodes configured to sense electrical cardiac activity of the heart, deliver electrical stimulation to the heart, sense the patient's transthoracic impedance, and/or sense other physiological parameters, e.g., cardiac chamber pressure or temperature. Portions of the housing 401 of the pulse generator 405 may optionally serve as a can electrode.

Communications circuitry is disposed within the housing 401 for facilitating communication between the pulse generator 405 and an external device, such as the external breathing therapy device or APM system. The communications circuitry can also facilitate unidirectional or bidirectional communication with one or more implanted, external, cutaneous, or subcutaneous physiologic or non-physiologic sensors, patient-input devices and/or information systems.

The pulse generator 405 may optionally incorporate a motion sensor 420. The motion sensor 420 may be configured to sense patient activity. Patient activity may be used in connection with sleep detection as described in more detail herein. The motion sensor 420 may be implemented as an accelerometer positioned in or on the housing 401 of the pulse generator 405. If the motion sensor is implemented as an accelerometer, the motion sensor may also provide acoustic information, e.g. rales, coughing, and cardiac, e.g. S1-S4 heart sounds, murmurs, and other acoustic information.

The lead system 410 of the CRM 400 may incorporate a transthoracic impedance sensor that may be used to acquire the patient's respiration waveform, or other respiration-related information. The transthoracic impedance sensor may include, for example, one or more intracardiac electrodes 441, 442, 451-455, 463 positioned in one or more chambers of the heart 490. The intracardiac electrodes 441, 442, 451-455, 463 may be coupled to impedance drive/sense circuitry 430 positioned within the housing of the pulse generator 405.

In one implementation, impedance drive/sense circuitry 430 generates a current that flows through the tissue between an impedance drive electrode 451 and a can electrode on the housing 401 of the pulse generator 405. The voltage at an impedance sense electrode 452 relative to the can electrode changes as the patient's transthoracic impedance changes. The voltage signal developed between the impedance sense electrode 452 and the can electrode is detected by the impedance sense circuitry 430. Other locations and/or combinations of impedance sense and drive electrodes are also possible.

Figure 7:
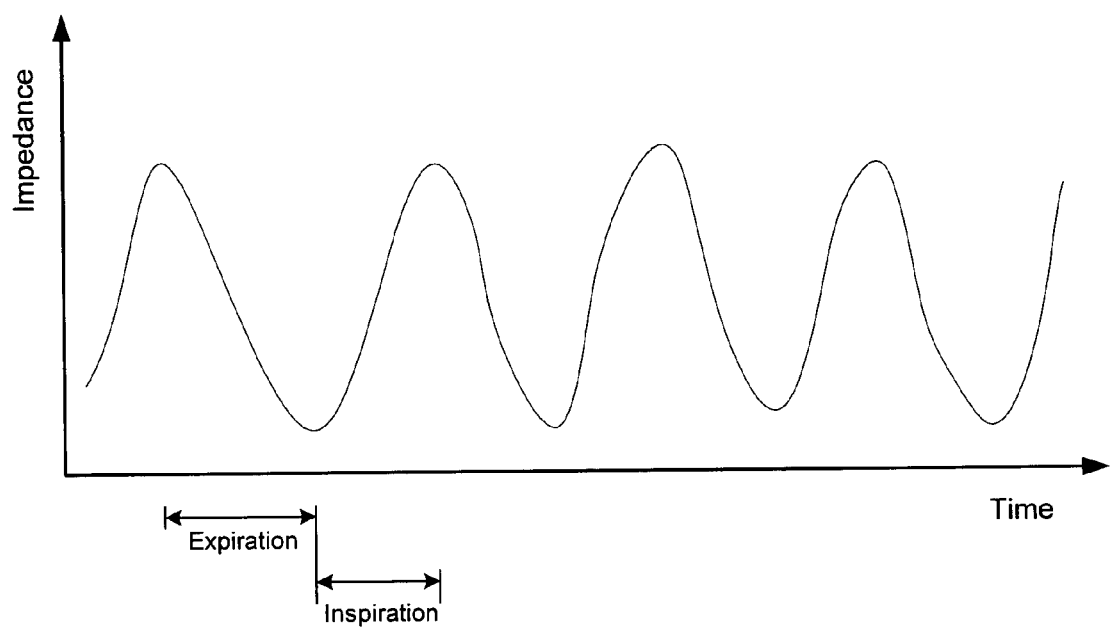
FIG. 7 is a graph of a respiration signal measured by a transthoracic impedance sensor that may be utilized for monitoring parameters of a breathing therapy in accordance with embodiments of the invention.

The voltage signal developed at the impedance sense electrode 452, illustrated in FIG. 7, is proportional to the patient's transthoracic impedance and represents the patient's respiration waveform. The transthoracic impedance increases during respiratory inspiration and decreases during respiratory expiration. The peak-to-peak transition of the transthoracic impedance is proportional to the amount of air moved in one breath, denoted the tidal volume. The amount of air moved per minute is denoted the minute ventilation. A normal "at rest" respiration pattern, e.g., during non-REM sleep, includes regular, rhythmic inspiration-expiration cycles without substantial interruptions, as indicated in FIG. 7.

Returning to FIG. 4A, the lead system 410 may include one or more cardiac pace/sense electrodes 451-455 positioned in, on, or about one or more heart chambers for sensing electrical signals from the patient's heart 490 and/or delivering pacing pulses to the heart 490. The intracardiac sense/pace electrodes 451-455, such as those illustrated in FIG. 4A, may be used to sense and/or pace one or more chambers of the heart, including the left ventricle, the right ventricle, the left atrium and/or the right atrium. The lead system 410 may include one or more defibrillation electrodes 441, 442 for delivering defibrillation/cardioversion shocks to the heart.

The pulse generator 405 may include circuitry for detecting cardiac arrhythmias and/or for controlling pacing or defibrillation therapy in the form of electrical stimulation pulses or shocks delivered to the heart through the lead system 410. Circuitry for monitoring external breathing therapy 435, including sensor interface circuitry, event detectors, monitoring processor, and/or memory circuitry, as described in connection with the FIG. 6, may be housed within the pulse generator 405. The monitoring circuitry may be coupled to various sensors, patient input devices, and/or information systems through leads or through wireless communication links.

Figure 4B:
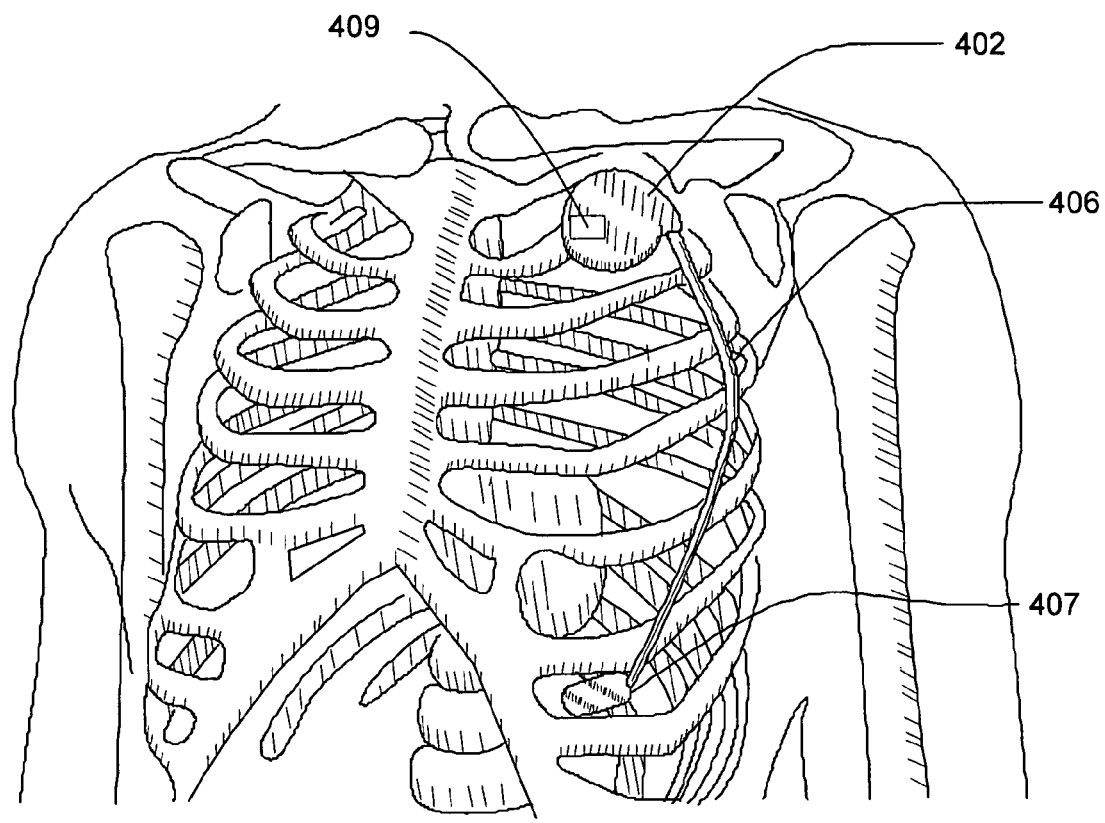
FIG. 4B is a partial view of an implantable subcutaneous medical device that may be used for coordinated patient monitoring, diagnosis, and/or therapy in accordance with an embodiment of the invention.

FIG. 4B is a diagram illustrating an implantable transthoracic cardiac device that may be used in connection with developing feedback information for sleep disordered breathing therapy in accordance with embodiments of the invention. The implantable device illustrated in FIG. 4B is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

Circuitry for implementing a monitoring device or monitoring device and a therapy feedback unit may be positioned within the primary housing of the ITCS device. The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature.

In another implementation, one or more electrodes may be located in direct contact with the heart, great vessel or coronary vasculature, such as via one or more leads implanted by use of conventional transvenous delivery approaches. In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

In the configuration shown in FIG. 4B, a subcutaneous electrode assembly 407 can be positioned under the skin in the chest region and situated distal from the housing 402. The subcutaneous and, if applicable, housing electrode(s) can be positioned about the heart at various locations and orientations, such as at various anterior and/or posterior locations relative to the heart. The subcutaneous electrode assembly 407 is coupled to circuitry within the housing 402 via a lead assembly 406. One or more conductors (e.g., coils or cables) are provided within the lead assembly 406 and electrically couple the subcutaneous electrode assembly 407 with circuitry in the housing 402. One or more sense, sense/pace or defibrillation electrodes can be situated on the elongated structure of the electrode support, the housing 402, and/or the distal electrode assembly (shown as subcutaneous electrode assembly 407 in FIG. 4B).

It is noted that the electrode and the lead assemblies 407, 406 can be configured to assume a variety of shapes. For example, the lead assembly 406 can have a wedge, chevron, flattened oval, or a ribbon shape, and the subcutaneous electrode assembly 407 can comprise a number of spaced electrodes, such as an array or band of electrodes. Moreover, two or more subcutaneous electrode assemblies 407 can be mounted to multiple electrode support assemblies 406 to achieve a desired spaced relationship amongst subcutaneous electrode assemblies 407.

In particular configurations, the ITCS device may perform functions traditionally performed by cardiac rhythm management devices, such as providing various cardiac monitoring, pacing and/or cardioversion/defibrillation functions. Exemplary pacemaker circuitry, structures and functionality, aspects of which can be incorporated in an ITCS device of a type that may benefit from multi-parameter sensing configurations, are disclosed in commonly owned U.S. Pat. Nos. 4,562,841; 5,284,136; 5,376,476; 5,036,849; 5,540,727; 5,836,987; 6,044,298; and 6,055,454, which are hereby incorporated herein by reference in their respective entireties. It is understood that ITCS device configurations can provide for non-physiologic pacing support in addition to, or to the exclusion of, bradycardia and/or anti-tachycardia pacing therapies. Exemplary cardiac monitoring circuitry, structures and functionality, aspects of which can be incorporated in an ITCS of the present invention, are disclosed in commonly owned U.S. Pat. Nos. 5,313,953; 5,388,578; and 5,411,031, which are hereby incorporated herein by reference in their respective entireties.

An ITCS device can incorporate circuitry, structures and functionality of the subcutaneous implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243 and commonly owned U.S. Patent Applications Ser. No. 60/462,272, filed Apr. 11, 2003, Ser. No. 10/462,001, filed Jun. 13, 2003, Ser. No. 10/465,520, filed Jun. 19, 2003, Ser. No. 10/820,642 filed Apr. 8, 2004 and Ser. No. 10/821,248, filed Apr. 8, 2004 which are incorporated herein by reference.

The housing of the ITCS device may incorporate components of a monitoring unit 409, including a memory, sensor interface, and/or event detector circuitry. The monitoring unit 409 may be coupled to one or more sensors, patient input devices, and/or information systems as described in connection with FIG. 2. In some embodiments, the housing of the ITCS device may also incorporate components of a therapy feedback unit. In other embodiments, circuitry to implement the therapy feedback unit may be configured within a separate device from the monitoring unit. In this embodiment, the therapy feedback unit and the monitoring unit may be communicatively coupled using leads or a wireless communication link, for example.

In one implementation, the ITCS device may include an impedance sensor configured to sense the patient's transthoracic impedance. The impedance sensor may include the impedance drive/sense circuitry incorporated with the housing 402 of the ITCS device and coupled to impedance electrodes positioned on the can or at other locations of the ITCS device, such as on the subcutaneous electrode assembly 407 and/or lead assembly 406. In one configuration, the impedance drive circuitry generates a current that flows between a subcutaneous impedance drive electrode and a can electrode on the primary housing of the ITCS device. The voltage at a subcutaneous impedance sense electrode relative to the can electrode changes as the patient's transthoracic impedance changes. The voltage signal developed between the impedance sense electrode and the can electrode is sensed by the impedance drive/sense circuitry.

Communications circuitry is disposed within the housing 402 for facilitating communication between the ITCS device, including the monitoring unit 409, and an external communication device, such as a portable or bed-side communication station, patient-carried/worn communication station, or external programmer, for example. The communications circuitry can also facilitate unidirectional or bidirectional communication with one or more external, cutaneous, or subcutaneous physiologic or non-physiologic sensors.

Figure 5:
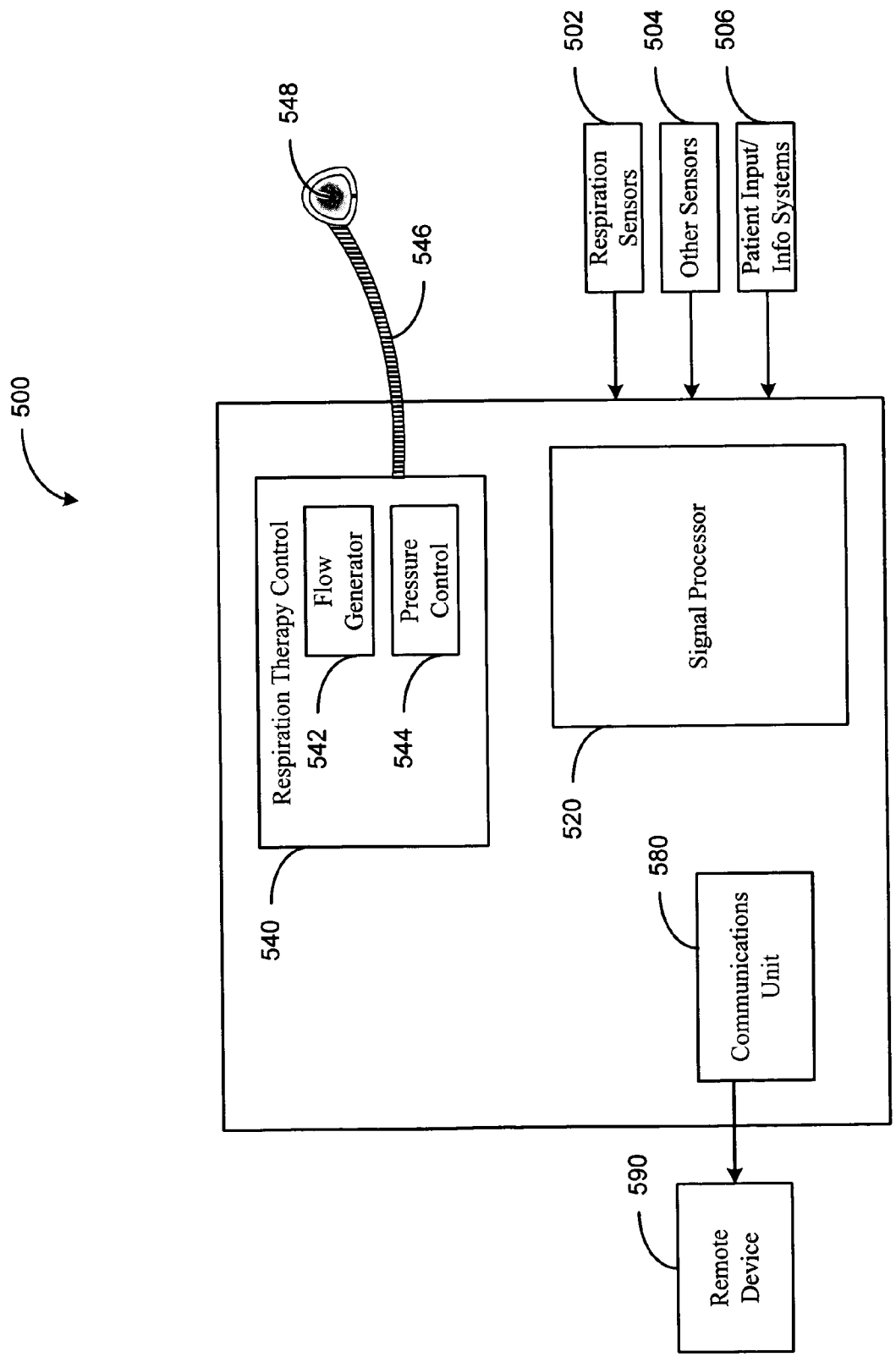
FIG. 5 is a block diagram of an implantable cardiac rhythm management system that may be used to monitor external breathing therapy in accordance with embodiments of the invention.

FIG. 5 illustrates a block diagram of an external breathing therapy device 500, e.g., xPAP device that may be used to provide therapy to the patient for various types of disordered breathing. An implantable monitoring device, implemented as a component of the CRM or ITCS systems described in connection with FIGS. 4A and 4B, respectively, may collect information related to the breathing therapy.

As previously discussed, the xPAP device 500 may include any of the positive airway pressure devices, including CPAP, bi-PAP, PPAP, and/or autotitration positive airway pressure devices, for example. Continuous positive airway pressure (CPAP) devices deliver a set air pressure to the patient. The pressure level for the individual patient may be determined during a titration study. Such a study may take place in a sleep lab, and involves determination of the optimum airway pressure by a sleep physician or other professional. The CPAP device pressure control is set to the determined level. When the patient uses the CPAP device, a substantially constant airway pressure level is maintained by the device.

Autotitration PAP devices are similar to CPAP devices, however, the pressure controller for autotitration devices automatically determines the air pressure for the patient. Instead of maintaining a constant pressure, the autotitration PAP device evaluates sensor signals and the changing needs of the patient to deliver a variable positive airway pressure. Autotitration PAP and CPAP are often used to treat sleep disordered breathing, for example.

Bi-level positive airway pressure (bi-PAP) devices provide two levels of positive airway pressure. A higher pressure is maintained while the patient inhales. The device switches to a lower pressure during expiration. Bi-PAP devices are used to treat a variety of respiratory dysfunctions, including chronic obstructive pulmonary disease (COPD), respiratory insufficiency, and ALS or Lou Gehrig's disease, among others.

The xPAP device 500 may be coupled to sensors, input devices, and information systems 502, 504, 506 used to sense respiration-related and/or other patient conditions. A signal processor 520 may be used to condition the signals received from the sensors and/or other input devices 502, 504, 506. The signal processor 520 may include, for example, drive circuitry for activating the sensors, as well as filters, amplifiers, and/or A/D conversion circuitry for conditioning the sensor signals.

The breathing therapy control unit 540 includes a flow generator 542 that pulls in air through a filter. The flow generator 542 is controlled by the pressure control circuitry 544 to deliver an appropriate air pressure to the patient. Air flows through tubing 546 coupled to the xPAP device 500 and is delivered to the patient's airway through a mask 548. In one example, the mask 548 may be a nasal mask covering only the patient's nose. In another example, the mask 548 covers the patient's nose and mouth.

The xPAP device 500 may include a communications unit 580 for communicating with one or more separate devices, including the implantable monitoring device, or other remote devices 590. In one example, the xPAP device 500 may receive information about the breathing therapy delivered by the xPAP device 500 from a patient-internal device. In another example, the xPAP device 500 may receive information from or transmit information to a patient management server or other computing device through the communications circuitry 580.

Figure 6:
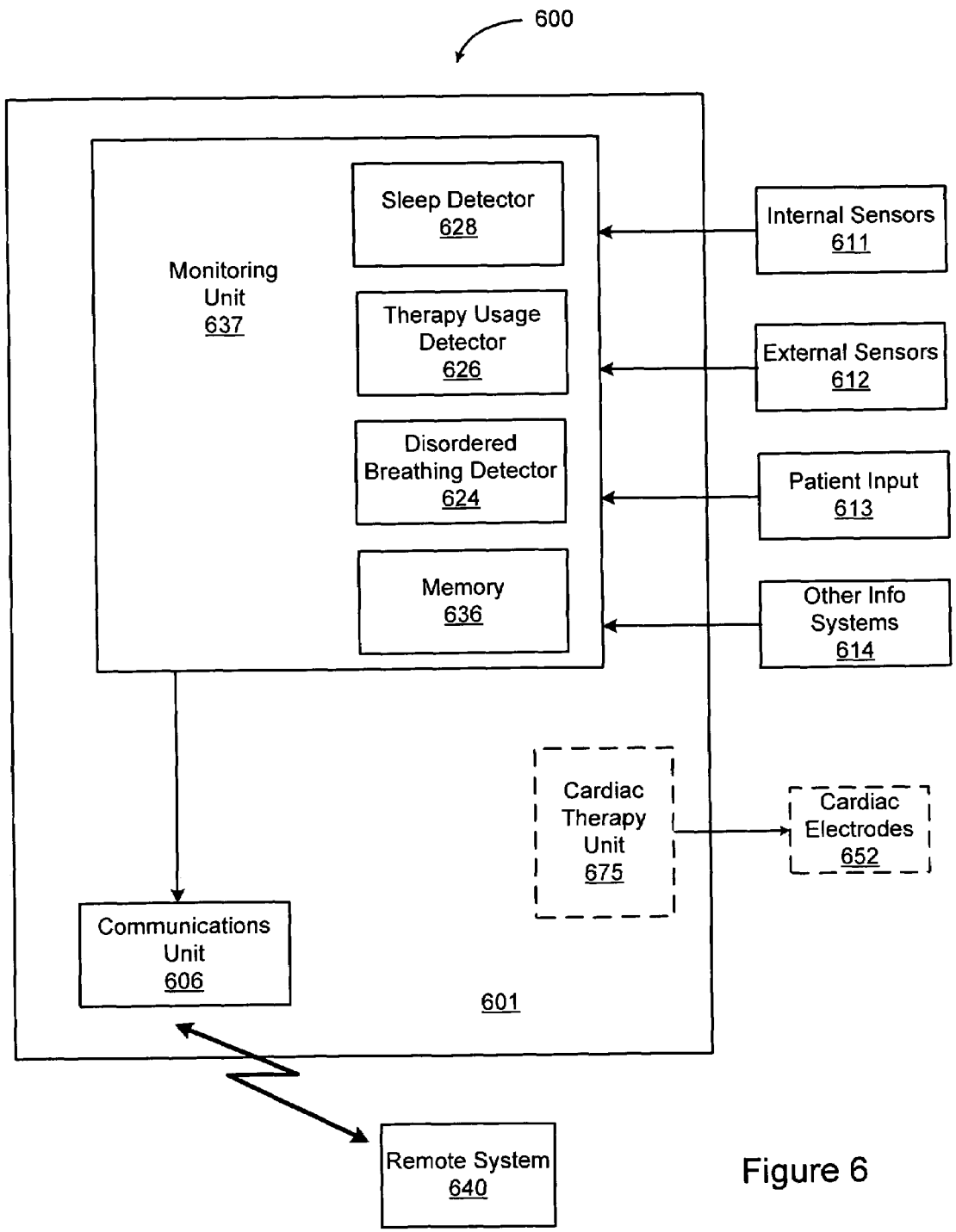
FIG. 6 is a block diagram of a patient-external respiratory therapy device that may be used to provide breathing therapy monitored by an implantable device in accordance with embodiments of the invention.

The block diagram of FIG. 6 illustrates an example of medical system 600 including a fully or partially implantable device 601 that may be used to monitor breathing therapy delivered by an external device in accordance with embodiments of the invention. The system 600 employs a medical device 601 that may be coupled to an array of data acquisition devices, including patient-internal sensors 611, patient-external sensors 612, patient input devices 613, and/or other information systems 614 as described herein.

Conditions used to monitor parameters of the breathing therapy may include both physiological and non-physiological contextual conditions affecting the patient. Physiological conditions may include a broad category of conditions associated with the internal functioning of the patient's physiological systems, including the cardiovascular, respiratory, nervous, muscle and other systems. Examples of physiological conditions include blood chemistry, patient posture, patient activity, respiration quality, sleep quality, among others.

Contextual conditions are non-physiological conditions representing patient-external or background conditions. Contextual conditions may be broadly defined to include, for example, present environmental conditions, such as patient location, ambient temperature, humidity, air pollution index. Contextual conditions may also include historical/background conditions relating to the patient, including the patient's normal sleep time and the patient's medical history, for example. Methods and systems for detecting some contextual conditions, including, for example, proximity to bed detection, are described in commonly owned U.S. patent application Ser. No. 10/269,611, filed Oct. 11, 2002, which is incorporated herein by reference.

Table 1 provides a representative set of patient conditions that may be used to monitor breathing therapy in accordance with embodiments of the invention. Table 1 also provides illustrative sensing methods that may be employed to sense the conditions. It will be appreciated that patient conditions and detection methods other than those listed in Table 1 may be used and are considered to be within the scope of the invention.

TABLE 1

| Condition Type | | Condition | Sensor type or Detection method |
|---|---|---|---|
| Physiological | Cardiovascular System | Heart rate | EGM, ECG |
| | | Heart rate variability | |
| | | QT interval | |
| | | Ventricular filling pressure | Intracardiac pressure sensor |
| | | Blood pressure | Blood pressure sensor |
| | Respiratory System | Snoring | Accelerometer Microphone |
| | | Respiration pattern (Tidal volume Minute ventilation Respiratory rate) | Transthoracic impedance sensor (AC) |
| | | Patency of upper airway | Intrathoracic impedance sensor |
| | | Pulmonary congestion | Transthoracic impedance sensor (DC) |
| | Nervous System | Sympathetic nerve activity | Muscle sympathetic nerve Activity sensor |
| | | Brain activity | EEG |
| | Blood Chemistry | $CO_2$ saturation | Blood analysis |
| | | $O_2$ saturation | |
| | | Blood alcohol content | |
| | | Adrenalin | |
| | | Brain Natriuretic Peptide (BNP) | |
| | | C-Reactive Protein | |
| | | Drug/Medication/Tobacco use | |
| | Muscle System | Muscle atonia | EMG |
| | | Eye movement | EOG |
| | | Patient activity | Accelerometer, MV, etc. |
| | | Limb movements | Accelerometer, EMG |
| | | Jaw movements | Accelerometer, EMG |
| | | Posture | Multi-axis accelerometer |
| Contextual/ Non-physiological | Environmental | Ambient temperature | Thermometer |
| | | Humidity | Hygrometer |
| | | Pollution | Air quality website |
| | | Time | Clock |
| | | Barometric pressure | Barometer |
| | | Ambient noise | Microphone |
| | | Ambient light | Photodetector |
| | | Altitude | Altimeter |
| | | Location | GPS, proximity sensor |
| | | Proximity to bed | Proximity to bed sensor |
| | Historical/ Background | Historical sleep time | Patient input, previously detected sleep onset times |
| | | Medical history | Patient input |
| | | Age | |
| | | Recent exercise | |
| | | Weight | |
| | | Gender | |
| | | Body mass index | |
| | | Neck size | |
| | | Emotional state | |
| | | Psychological history | |
| | | Daytime sleepiness | |
| | | Patient perception of sleep quality | |
| | | Drug, alcohol, nicotine use | |

The implantable device 601 of FIG. 6 includes a monitoring unit 637 that processes signals received from the sensors, 611, 612, patient input devices 613, and/or other information system 614. The monitoring unit 637 may include one or more a detection units 624, 626, 628 that detect the occurrence of various physiological events. For example, the monitoring unit 637 may include one or more of a disordered breathing detector 624, a sleep detector 628, and/or a therapy usage detector 626. Other event detection components may also be included in the monitoring unit 637. The monitoring unit 637 may include circuitry used to calculate various indices, such as AHI, % PB, arousals per unit time, and/or other indices that can be used to evaluate therapy efficacy, therapy impact and/or other parameters. The monitoring unit 637 may compare the patient's therapy usage to a prescribed therapy to determine therapy compliance.

The disordered breathing detector 624 may be coupled to a respiration sensor, for example, and used to detect disordered breathing events based on the inspiratory and expiratory phases of the patient's respiration cycles, for example. The sleep detector 628 may analyze various inputs from the patient-internal sensors 611, patient-external sensors 612, patient input devices 613, and/or other information systems 614 to detect sleep-related events, including, for example, sleep onset, sleep offset, sleep stages, and arousals from sleep.

The therapy usage detector may detect the proximity of the patient to the external breathing device, to determine therapy usage. In another example, the therapy usage detector may analyze the patient's respiration waveform to determine therapy usage.

The monitoring unit 637 may operate in cooperation with a memory 636. The memory 636 may store information derived from signals produced by the patient-internal sensors 611, patient-external sensors 612, patient input devices 613, and/or other information systems 614. The memory 636 may also store information about detected events, e.g., sleep and disordered breathing events, and/or information related to calculated indices characterizing various events such as sleep and/or disordered breathing events. The stored data, along with other information related to the breathing therapy may be transmitted to another component of the medical device 601 or to a separate device 640 for storage, further processing, trending, analysis, printing and/or display, for example. In one scenario, the stored data can be downloaded to a separate device periodically or on command. The stored data may be presented to the patient's health care professional on a real-time basis, or as a long-term, e.g., month long or year long, trend of daily measurements.

The medical device 601 may optionally include a therapy unit. In various examples provided herein, the medical device 601 is a cardiac device configured to deliver cardiac electrical stimulation therapy using a cardiac pulse generator 675 and electrical stimulation electrodes 652.

The medical device 601 may further include a communications unit 606 that controls communications between the medical device 601 and other devices or systems. For example, the communications unit 606 may be used to provide wireless or wired communications links between the medical device 601 and one or more of the patient-internal sensors 611, patient-external sensors 612, patient input devices 613, and information systems 614.

The communications unit 606 may also facilitate communications between the medical device 601 and a remote device 640 such as the patient-external breathing therapy device, a programmer, and/or an APM system. The wireless connections coupling the medical device 601 to various other devices and systems may utilize a variety of wireless protocols, including, for example, Bluetooth, IEEE 802.11, and/or a proprietary wireless protocol.

Detecting the onset, termination, duration, stages, and quality of sleep experienced by a patient may be employed in connection with monitoring breathing therapy. Patients suffering from sleep apnea, or other types of sleep disordered breathing, are generally treated with breathing therapy only during periods of sleep. Monitoring the sleep disordered breathing therapy may involve determining when the patient is asleep and/or monitoring arousals and/or various sleep stages.

In addition, monitoring patient sleep may be used to assess an impact of breathing therapy on the patient. Therapy impact information may be used to determine an appropriate breathing therapy for the patient. The implantable monitoring device may include a sleep detector 628 for detecting when the patient is asleep and the various stages of sleep. Various methods of sleep detection implementable in an implanted device involve sensing one or more conditions associated with sleep. The sleep-related conditions may be compared to a threshold to determine if the patient is asleep.

The sleep-related conditions may be derived from patient-external or implantable sensors and analyzed by a sleep detector located in the implantable monitoring device or by circuitry within the APM communication unit (i.e., a supervisor device that co-ordinates diagnostics between various sensors. In one implementation proximity to bed, sleep detection may be implemented in an implantable cardiac rhythm management system configured as a pacemaker/defibrillator as illustrated in FIG. 4A or the ITCS device illustrated in FIG. 4B.

Sleep detection may involve sensing one or more conditions indicative of sleep. A representative set of sleep-related conditions include body movement, heart rate, QT interval, eye movement, respiration rate, transthoracic impedance, tidal volume, minute ventilation, body posture, brain activity, cardiac activity, muscle tone, body temperature, time of day, historical sleep times, blood pressure, and blood gas concentration, proximity to bed, for example.

Sleep may be detected by comparing levels of the one or more sleep-related conditions to one or more sleep thresholds. For example, sleep may be detected by based on the patient's heart rate. When the patient's heart rate decreases below a sleep threshold, the patient may be determined to be asleep. Sleep may also be detected base on the patient's activity. If the patient's activity decreases below a sleep threshold, then the patient may be determined to be asleep. Another method of detecting sleep involves monitoring the patient's minute ventilation. If the patient's minute ventilation falls below a sleep threshold, then the patient may be determined to be asleep.

Sleep may be detected by comparing multiple sleep-related conditions to multiple thresholds. For example, the patient may be determined to be asleep if the patient's activity, sensed by an accelerometer, falls below an activity sleep threshold and the patient's heart rate, sensed by cardiac electrodes, falls below a heart rate sleep threshold.

Sleep may also be detected using one sleep-related condition to modify the sleep threshold of another sleep-related condition. A first sleep-related condition may be sensed. The level of the sleep-related condition may be compared to a sleep threshold to determine the onset and termination of sleep. A second sleep-related condition may be used to adjust the sleep threshold. Additional sleep-related conditions may optionally be sensed to confirm the onset or termination of the sleep condition.

A sleep detector 628 (FIG. 6) may be configured to compare the levels of one or more sleep-related conditions to one or more thresholds. In one implementation, the one sleep related condition may be compared to a sleep threshold or other index to detect sleep. In another implementation, multiple sleep-related conditions may be compared to multiple thresholds or indices. In a further implementation, one or more of the sleep-related conditions may be used to adjust the sleep thresholds or indices. Furthermore, the onset or termination of sleep may be confirmed using an additional number of sleep-related conditions.

One or more sleep-related conditions may be sensed using implantable sensors and/or patient-external sensors, for example. In one embodiment, patient activity may be compared to a sleep threshold to determine when the patient is asleep. A low level of activity is indicative that the patient is sleeping. Patient activity may be sensed, for example, using an accelerometer positioned on or in the housing of an implantable cardiac device, or in another convenient location. The accelerometer signal may be correlated with activity level or workload.

A second sleep-related condition may be used to adjust the sleep threshold. In one embodiment, the patient's minute ventilation is used to adjust the sleep threshold. The patient's respiration may be sensed using a transthoracic impedance sensor. Transthoracic impedance may be used to derive various parameters associated with respiration, including, for example, tidal volume and/or minute ventilation. A transthoracic impedance sensor may be integrated into an implantable cardiac device with intracardiac electrodes, for example. Impedance driver circuitry generates a current that flows through the blood between the impedance drive electrode and a can electrode on the housing of the cardiac device. The voltage at an impedance sense electrode relative to the can electrode changes as the transthoracic impedance changes.

The voltage signal developed at the impedance sense electrode, illustrated in FIG. 7, is proportional to the transthoracic impedance, with the impedance increasing during respiratory inspiration and decreasing during respiratory expiration. The peak-to-peak transition of the impedance, illustrated in FIG. 7, is proportional to the amount of air inhaled in one breath, denoted the tidal volume. The variations in impedance during respiration may be used to determine the respiration tidal volume, corresponding to the volume of air moved in a breath, or minute ventilation corresponding to the amount of air moved per minute.

Figure 8:
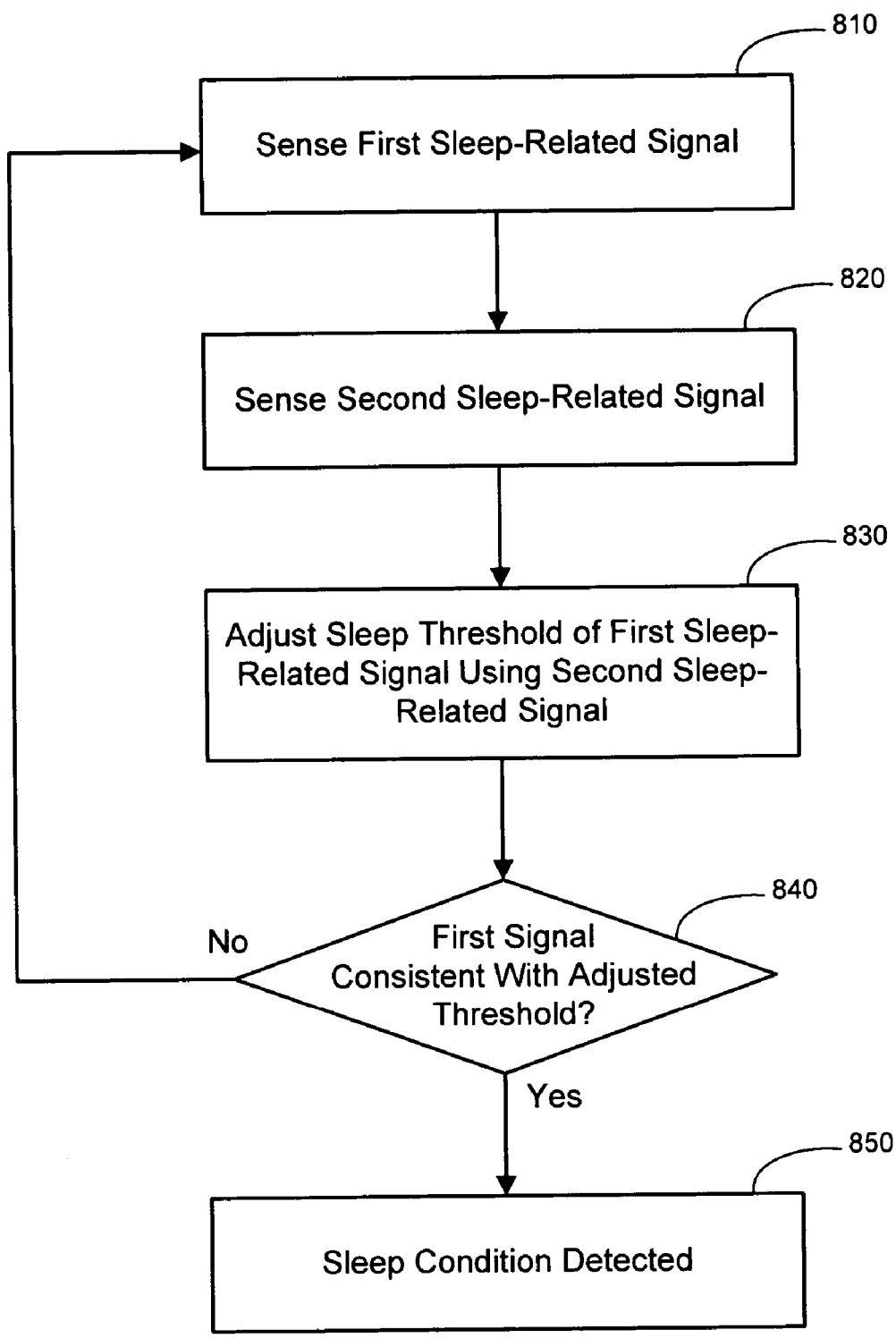
FIG. 8 is a block diagram of a sleep detector in accordance with embodiments of the invention.

FIG. 8 is a flow chart illustrating a method of detecting sleep according to an embodiment of the invention. A sleep threshold associated with a first sleep-related condition is established. The sleep threshold may be determined from clinical data of a sleep threshold associated with sleep acquired using a group of subjects, for example. The sleep threshold may also be determined using historical data taken from the particular patient for whom onset and offset of sleep is to be determined. For example, a history of a particular patient's sleep times can be stored, and a sleep threshold can be developed using data associated with the patient's sleep time history.

First and second signals associated with sleep-related conditions are sensed 810, 820. The first and the second signals may be any signal associated with the condition of sleep, such as the representative sleep-related conditions associated with sleep listed above.

The sleep threshold established for the first signal is adjusted 830 using the second signal. For example, if the second signal indicates condition, e.g., high level of patient activity that is incompatible with a sleep state, the sleep threshold of the first signal may be adjusted downward to require sensing a decreased level of the first signal before a sleep condition is detected.

If the first signal is consistent with sleep according to the adjusted sleep threshold 840, a sleep condition is detected 850. If the first signal is not consistent with sleep using the adjusted sleep threshold, the first and the second signals continue to be sensed 810, 820 and the threshold adjusted 830 until a condition of sleep is detected 850.

Figure 9:
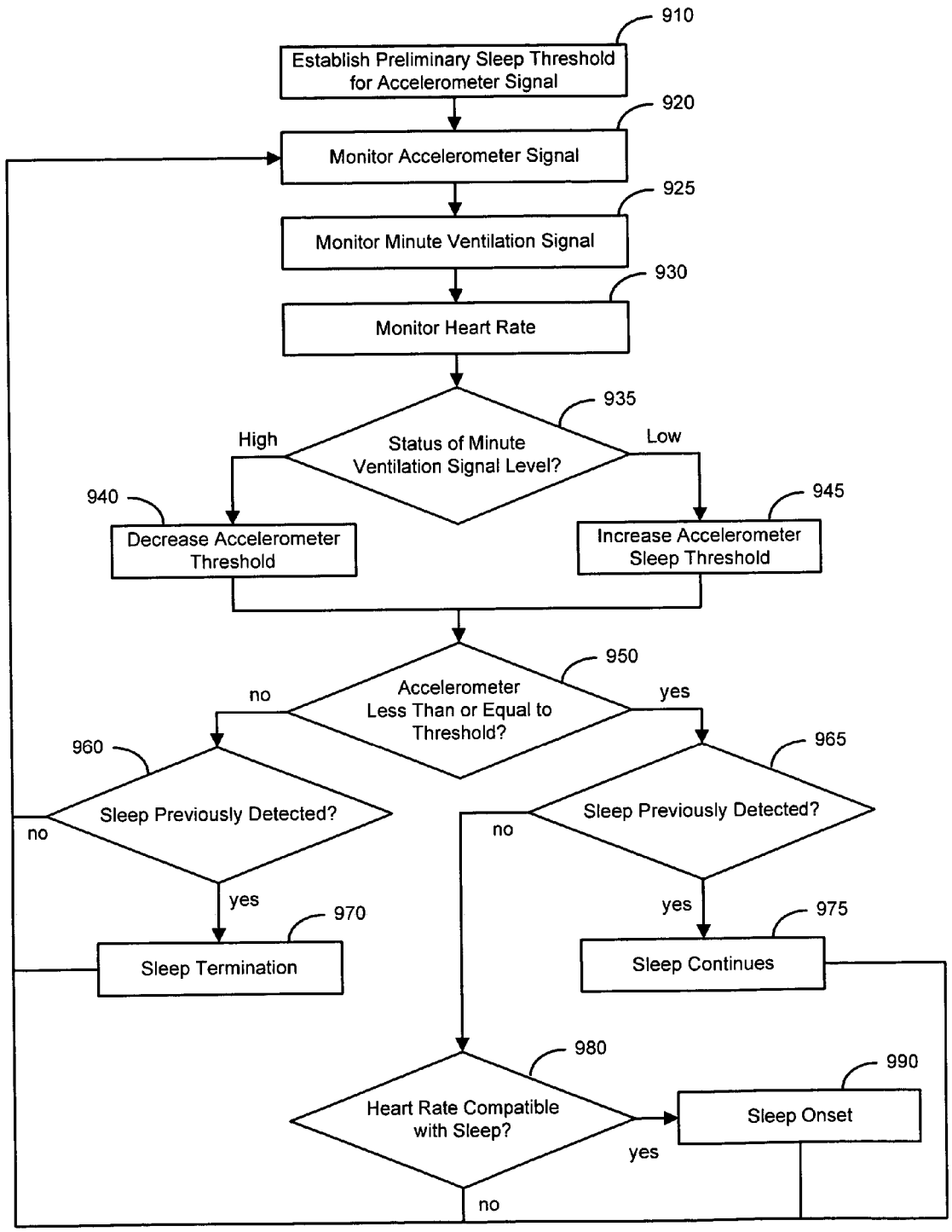
FIG. 9 is a flow chart illustrating a sleep detection method based on signals from an accelerometer and a minute ventilation sensor in accordance with embodiments of the invention.

In another embodiment of the invention, illustrated in the flow chart of FIG. 9, an accelerometer and a minute ventilation sensor are used to develop the first and second signals associated with sleep. A preliminary accelerometer signal sleep threshold is determined 910. For example, the preliminary sleep threshold may be determined from clinical data taken from a group of subjects or historical data taken from the patient over a period of time.

The activity level of the patient is sensed using an accelerometer 920 that may be incorporated into an implantable cardiac pacemaker as described above. Alternatively, the accelerometer may be attached externally to the patient. The patient's minute ventilation (MV) signal is determined 925. The MV signal may be acquired, for example, based on the transthoracic impedance signal as described above using an implantable cardiac device. Other methods of determining the MV signal are also possible and are considered to be within the scope of this invention.

In this example, the accelerometer signal represents the sleep detection signal that is compared to the sleep threshold. The MV signal is the threshold adjustment signal used to adjust the sleep threshold. Heart rate is determined 930 in this example to provide a sleep confirmation signal.

Threshold adjustment may be accomplished by using the patient's MV signal to moderate the accelerometer sleep threshold. If the patient's MV signal is low relative to an expected MV level associated with sleep, the accelerometer sleep threshold is increased. Similarly, if the patient's MV signal level is high relative to an expected MV level associated with sleep, the accelerometer sleep threshold is decreased. Thus, when the patient's MV level is high, less activity is required to make the determination that the patient is sleeping. Conversely when the patient's MV level is relatively low, a higher activity level may result in detection of sleep. The use of two sleep-related signals to determine a sleep condition enhances the accuracy of sleep detection over previous methods using only one sleep-related signal to determine that a patient is sleeping.

Various signal processing techniques may be employed to process the raw sensor signals. For example, a moving average of a plurality of samples of each sleep-related signal may be calculated and used as the sleep-related signal. Furthermore, the sleep-related signals may be filtered and/or digitized. If the MV signal is high 935 relative to an expected MV level associated with sleep, the accelerometer sleep threshold is decreased 940. If the MV signal is low 935 relative to an expected MV level associated with sleep, the accelerometer sleep threshold is increased 945.

If the sensed accelerometer signal is less than or equal to the adjusted sleep threshold 950, and if the patient is not currently in a sleep state 965, then the patient's heart rate is checked 980 to confirm the sleep condition. If the patient's heart rate is compatible with sleep 980, then sleep onset is determined 990. If the patient's heart rate is incompatible with sleep, then the patient's sleep-related signals continue to be sensed.

If the accelerometer signal is less than or equal to the adjusted sleep threshold 950 and if the patient is currently in a sleep state 965, then a continuing sleep state is determined and the patient's sleep-related signals continue to be sensed for sleep termination to occur.

If the accelerometer signal is greater than the adjusted sleep threshold 950 and the patient is not currently in a sleep state 960, then the patient's sleep-related signals continue to be sensed until sleep onset is detected 990. If the accelerometer signal is greater than the adjusted sleep threshold 950 and the patient is currently in a sleep state 960, then sleep termination is detected 970.

Figure 10A:
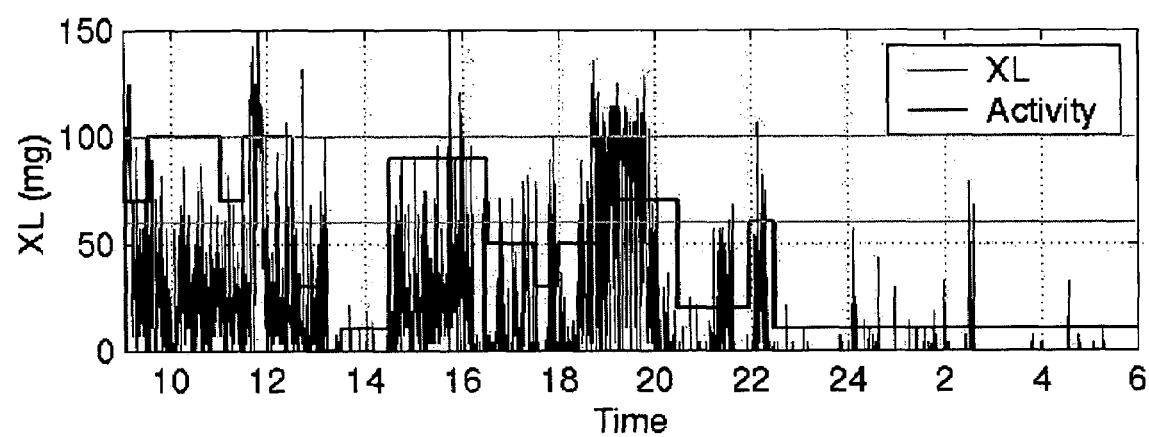
FIG. 10A is a graph of an accelerometer signal indicating patient activity level that may be used for sleep detection in accordance with embodiments of the invention.
Figure 10B:
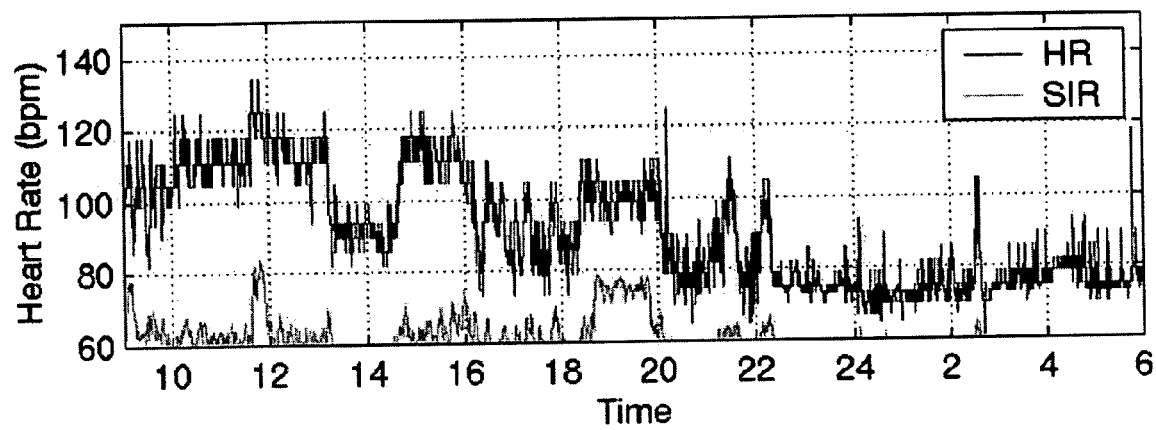
FIG. 10B is a graph of a patient's heart rate and sensor indicated rate that may be used for sleep detection in accordance with an embodiment of the invention.
Figure 11:
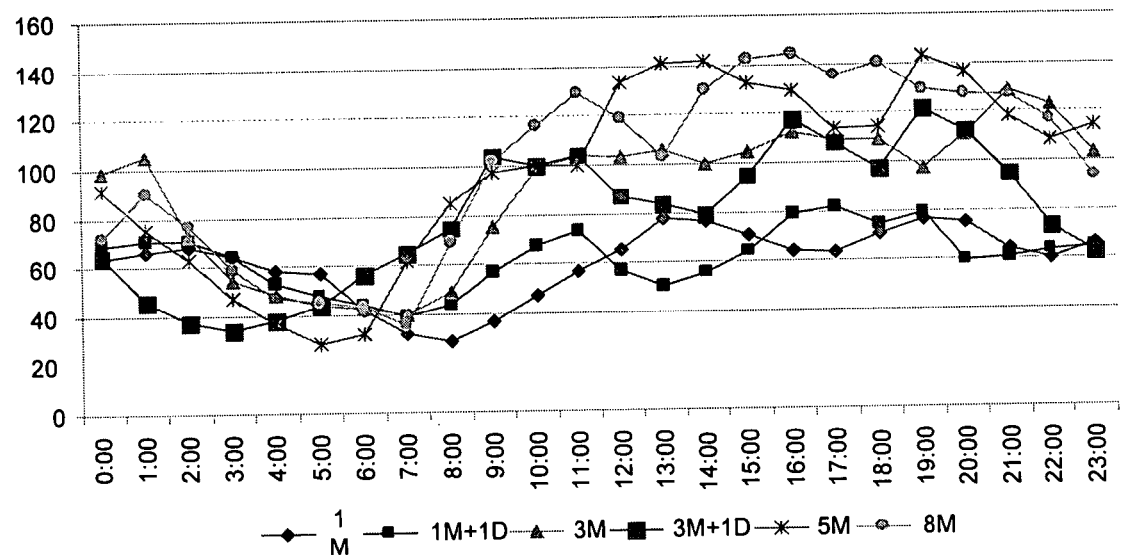
FIG. 11 is a graph of baseline trending for an MV signal used for sleep detection in accordance with embodiments of the invention.
Figure 12:
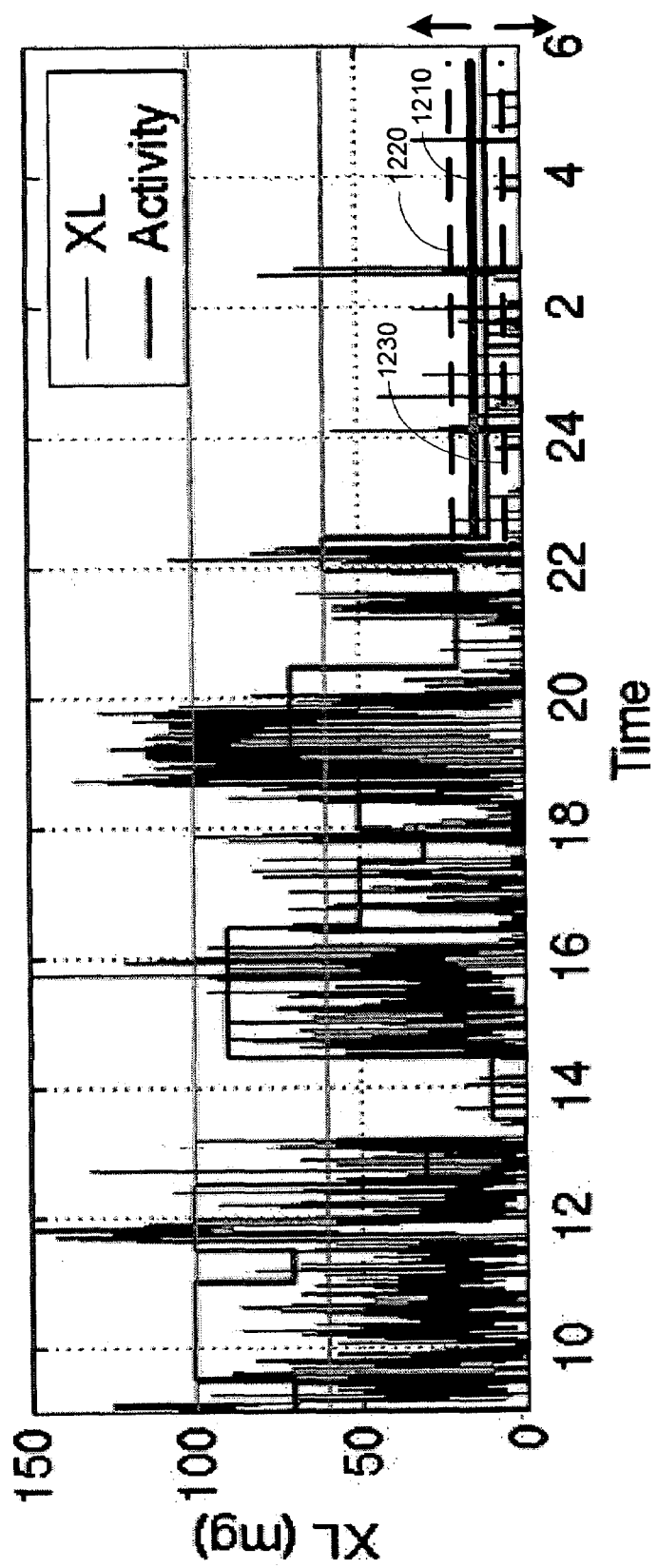
FIG. 12 illustrates adjustment of an accelerometer sleep threshold using an MV signal in accordance with embodiments of the invention

The graphs of FIGS. 10-12 illustrate the adjustment of the accelerometer sleep threshold using the MV signal. The relationship between patient activity and the accelerometer and MV signals is trended over a period of time to determine relative signal levels associated with a sleep condition. FIG. 10A illustrates activity as indicated by the accelerometer signal. The patient's heart rate for the same period is graphed in FIG. 10B. The accelerometer signal indicates a period of sleep associated with a relatively low level of activity beginning at slightly before 23:00 and continuing through 6:00. Heart rate appropriately tracks the activity level indicated by the accelerometer indicating a similar period of low heart rate corresponding to sleep. The accelerometer trends are used to establish a threshold for sleep detection.

FIG. 11 is a graph of baseline trending for an MV signal. Historical data of minute ventilation of a patient is graphed over an 8 month period. The MV signal trending data is used to determine the MV signal level associated with sleep. In this example, a composite MV signal using the historical data indicates a roughly sinusoidal shape with the relatively low MV levels occurring approximately during the period from hours 21:00 through 8:00. The low MV levels are associated with periods of sleep. The MV signal level associated with sleep is used to implement sleep threshold adjustment.

FIG. 12 illustrates adjustment of the accelerometer sleep threshold using the MV signal. The initial sleep threshold 1210 is established using the baseline accelerometer signal data acquired as discussed above. If the patient's MV signal is low relative to an expected MV level associated with sleep, the accelerometer sleep threshold is increased 1220. If the patient's MV signal level is high relative to an expected MV level associated with sleep, the accelerometer sleep threshold is decreased 1230. When the patient's MV level is high, less activity detected by the accelerometer is required to make the determination that the patient is sleeping. However, if the patient's MV level is relatively low a higher activity level may result in detection of sleep. The use of two sleep-related signals to adjust a sleep threshold for determining a sleep condition enhances the accuracy of sleep detection over previous methods.

Additional sleep-related signals may be sensed and used to improve the sleep detection mechanism described above. For example, a posture sensor may be used to detect the posture of the patient and used to confirm sleep. If the posture sensor indicates a vertical posture, then the posture sensor signal may be used to override a determination of sleep using the sleep detection and threshold adjustment signals. Other signals may also be used in connection with sleep determination or confirmation, including the representative set of sleep-related signals associated with sleep indicated above. Methods and systems related to sleep detection, aspects of which may be utilized in connection with the methodologies of the present invention, are described in commonly owned U.S. patent application Ser. No. 10/309,771, filed Dec. 4, 2002, which is incorporated herein by reference.

The above described sleep-detection methods may be used for discriminating between periods of sleep and periods of wakefulness. Knowledge of sleep onset, offset, arousal episodes, and/or length of uninterrupted sleep may be used to adjust patient therapy.

Sleep stage discrimination, including REM and non-REM sleep stages may additionally be used in connection with external breathing therapy. For example, some patients may experience sleep disordered breathing primarily during particular sleep stages. The implantable device may monitor sleep stages and disordered breathing episodes. The breathing information may be analyzed in view of the sleep stage information. The analysis may be helpful in adapting a breathing therapy for a patient, e.g. delivering breathing therapy during sleep stages that predispose the patient to disordered breathing episodes. In one implementation, sleep stage may be determined using information from an EEG sensor. In one implementation, sleep information associated with sleep stages and/or arousals from sleep may be determined using information from an EEG sensor. Systems and methods for detecting arousals from sleep, aspects of which may be utilized in connection with the present invention, are described in commonly owned U.S. patent application entitled "Autonomic Arousal Detection System and Method," identified by Attorney Docket Number GUID.106PA, filed on Aug. 17, 2004, which is incorporated herein by reference.

In another implementation, sleep stage information may be obtained using one or more muscle atonia sensors. Methods and systems for implementing of sleep stage detection using muscle atonia sensors are described in commonly owned U.S. patent application Ser. No. 10/643,006, filed on Aug. 18, 2003, which is incorporated herein by reference.

Various aspects of sleep quality, including number and severity of arousals, sleep disordered breathing episodes, limb movements during sleep, and cardiac, respiratory, muscle, and nervous system functioning during sleep may provide important information relevant to the delivery of breathing therapy. Methods and systems for collecting and assessing sleep quality data are described in commonly owned U.S. patent application Ser. No. 10/642,998, filed Aug. 18, 2003, which is incorporated herein by reference.

As previously described, monitoring the effectiveness and/or impact and/or other parameters of breathing therapy may involve detecting disordered breathing episodes. The respiratory disruptions caused by disordered breathing can be particularly serious for patients concurrently suffering from cardiovascular deficiencies, such as congestive heart failure. Unfortunately, disordered breathing is often undiagnosed. If left untreated, the effects of disordered breathing may result in serious health consequences for the patient.

Episodes of disordered breathing are associated with acute and chronic physiological effects. Acute responses to disordered breathing may include, for example, negative intrathoracic pressure, hypoxia, arousal from sleep, and increases in blood pressure and heart rate. During obstructive apnea episodes, negative intrathoracic pressure may arise from an increased effort to generate airflow. Attempted inspiration in the presence of an occluded airway results in an abrupt reduction in intrathoracic pressure. The repeated futile inspiratory efforts associated with obstructive sleep apnea may trigger a series of secondary responses, including mechanical, hemodynamic, chemical, neural, and inflammatory responses.

Obstructive sleep apneas may be terminated by arousal from sleep several seconds after the apneic peak, allowing the resumption of airflow. Coincident with arousal from sleep, surges in sympathetic nerve activity, blood pressure, and heart rate may occur. The adverse effects of obstructive apnea are not confined to sleep. Daytime sympathetic nerve activity and systemic blood pressure are increased. There may also be a sustained reduction in vagal tone, causing reduction in total heart rate variability during periods of wakefulness.

Central sleep apnea is generally caused by a failure of respiratory control signals from the brain. Central sleep apnea is a component of Cheyne-Stokes respiration (CSR), a respiration pattern primarily observed in patients suffering from chronic heart failure (CHF). Cheyne-Stokes respiration is a form of periodic breathing in which central apneas and hypopneas alternate with periods of hyperventilation causing a waxing-waning pattern of tidal volume. In some CHF patients, obstructive sleep apnea and central sleep apnea may coexist. In these patients, there may be a gradual shift from predominantly obstructive apneas at the beginning of the night to predominantly central apneas at the end of the night.

Several mechanisms may be involved in central apneas observed in patients suffering from chronic heart failure. According to one mechanism, increased carbon dioxide sensitivity in CHF patients triggers hyperventilation initiating a sleep apnea episode. Breathing is regulated by a negative feedback system that maintains the arterial partial pressure of carbon dioxide ($PaCO_2$) within limits. Changes in $PaCO_2$ lead to changes in ventilation wherein the greater the sensitivity to carbon dioxide, the greater the ventilatory response.

In patients with cardiopulmonary disorders, an increase in carbon dioxide sensitivity may minimize disturbances in $PaCO_2$, thus protecting them against the long-term consequences of hypercapnia, an excess of carbon dioxide in the blood. Although this protective mechanism may be beneficial while the patient is awake, the increased sensitivity to carbon dioxide may disrupt breathing during sleep.

During sleep, ventilation decreases and $PaCO_2$ levels increase. If the $PaCO_2$ level decreases below level referred to as the apneic threshold, ventilation stops, central sleep apnea begins, and $PaCO_2$ rises to previous levels.

In patients with increased sensitivity to carbon dioxide, the negative-feedback system that controls breathing initiates a large respiratory drive when $PaCO_2$ rises. The large respiratory drive produces hyperventilation. Hyperventilation, by driving the $PaCO_2$ level below the apneic threshold, results in central sleep apnea. As a result of the apnea, the $PaCO_2$ level rises again, leading to an increase in ventilation. In this way, cycles of hyperventilation and central apnea may recur throughout sleep.

The posture of congestive heart failure (CHF) patients during sleep may also be implicated in triggering apnea. When CHF patients lie down, the prone posture may create fluid accumulation and pulmonary congestion causing the patient to reflexively hyperventilate. The hyperventilation may lead to the cyclical pattern of hyperventilation-apnea described above.

Arousals are not necessarily required in central sleep apneas for breathing to resume at the termination of the apnea event. In central apnea, the arousals follow the resumption of breathing after an apnea event. The arousals may facilitate development of oscillations in ventilation by stimulating hyperventilation and reducing $PaCO_2$ below the apneic threshold. Cycles of alternating hyperventilation and apnea are sustained by the combination of increased respiratory drive, pulmonary congestion, sleep interruptions, and apnea-induced hypoxia causing $PaCO_2$ oscillations above and below the apneic threshold. Shifts in the patient's state of consciousness, particularly with repeated arousals, may further destabilize breathing.

With the transition from wakefulness to non-rapid eye movement (NREM) sleep, the neural drive to breathe decreases from the waking state, and the threshold for a respiratory response to carbon dioxide increases. Therefore, if the patient's $PaCO_2$ level during wakefulness is below this higher sleeping threshold, the transition to NREM sleep may be accompanied by a brief loss of respiratory drive triggering a central apnea. During the apnea, the $PaCO_2$ rises until it reaches the new higher threshold level and initiates breathing. If the patient transitions into sleep, regular breathing resumes. However, if an arousal occurs, the increased $PaCO_2$ level associated with sleep is too high for a state of wakefulness and will stimulate hyperventilation. Thus, although arousals terminate obstructive sleep apneas, arousals may initiate respiratory oscillations associated with central apneas, in particular, Cheyne-Stokes respiration.

In addition to the acute responses to sleep disordered breathing, such as those discussed above, sleep disordered breathing is also associated with a number of secondary or chronic responses, including, for example, chronic decrease in heart rate variability (HRV) and blood pressure changes. Patients with central sleep apnea may have higher urinary and circulating norepinephrine concentrations and lower $PaCO_2$ during both sleep and wakefulness.

Disordered breathing may be detected by sensing and analyzing various conditions associated with disordered breathing. Table 2 provides examples of how a representative subset of the physiological and contextual conditions listed in Table 1 may be used in connection with disordered breathing detection.

Detection of disordered breathing may involve comparing one condition or multiple conditions to one or more thresholds or other indices indicative of disordered breathing. A threshold or other index indicative of disordered breathing may comprise a predetermined level of a particular condition, e.g., blood oxygen level less than a predetermined amount. A threshold or other index indicative of disordered breathing may comprises a change in a level of a particular condition, e.g., heart rate decreasing from a sleep rate to lower rate within a predetermined time interval.

In one approach, the relationships between the conditions may be indicative of disordered breathing. In this embodiment, disordered breathing detection may be based on the existence and relative values associated with two or more conditions. For example, if condition A is present at a level of x, then condition B must also be present at a level of f(x) before a disordered breathing detection is made.

The thresholds and/or relationships indicative of disordered breathing may be highly patient specific. The thresholds and/or relationships indicative of disordered breathing may be determined on a case-by-case basis by monitoring conditions affecting the patient and monitoring disordered breathing episodes. The analysis may involve determining levels of the conditions and/or relationships between the conditions associated, e.g., statistically correlated, with disordered breathing episodes. The thresholds and/or relationships used in disordered breathing detection may be updated periodically to track changes in the patient's response to disordered breathing.

TABLE 2

| Condition Type | Condition | Examples of how condition may be used in disordered breathing detection |
| --- | --- | --- |
| Physiological | Heart rate | Decrease in heart rate may indicate disordered breathing episode. Increase in heart rate may indicate autonomic arousal from a disordered breathing episode. Decrease in heart rate may indicate the patient is asleep. |
| | Heart rate variability | Disordered breathing causes heart rate variability to decrease. Changes in HRV associated with sleep disordered breathing may be observed while the patient is awake or asleep |
| | QT Interval | May be used to detect sleep apnea. |
| | Ventricular filling pressure | May be used to identify/predict pulmonary congestion associated with respiratory disturbance. |

TABLE 2-continued

| Condition Type | Condition | Examples of how condition may be used in disordered breathing detection |
|---|---|---|
| | Blood pressure | Swings in on-line blood pressure measures are associated with apnea. Disordered breathing generally increases blood pressure variability - these changes may be observed while the patient is awake or asleep. |
| | Snoring | Snoring is associated with a higher incidence of obstructive sleep apnea and may be used to detect disordered breathing. Snoring indicates that the patient is asleep. |
| | Respiration pattern/rate | Respiration patterns including, e.g., respiration rate, may be used to detect disordered breathing episodes. Respiration patterns may be used to determine the type of disordered breathing. Respiration patterns may be used to detect that the patient is asleep. |
| | Patency of upper airway | Patency of upper airway is related to obstructive sleep apnea and may be used to detect episodes of obstructive sleep apnea. |
| | Pulmonary congestion | Pulmonary congestion is associated with respiratory disturbances. |
| | Sympathetic nerve activity | End of apnea associated with a spike in SNA. Changes in SNA observed while the patient is awake or asleep may be associated with sleep disordered breathing. |
| | Electro-encephalogram (EEG) | May be used to detect sleep. May be used to determine sleep stages, including REM and non-REM sleep stages. |
| | CO2 | Low CO2 levels initiate central apnea. May be used to predict central apnea risk. |
| | O2 | O2 desaturation occurs during severe apnea/hypopnea episodes. May be used to evaluate a presence and severity of sleep disordered breathing events. |
| | Blood alcohol content | Alcohol tends to increase incidence of snoring & obstructive apnea. |
| | Adrenalin | End of apnea associated with a spike in blood adrenaline. |
| | Brain Natruiretic Peptide (BNP) | A marker of heart failure status, which is associated with Cheyne-Stokes Respiration |
| | C-Reactive Protein | A measure of inflammation that may be related to apnea. |
| | Drug/ Medication/ Tobacco use | These substances may affect the incidence of both central & obstructive apnea. |
| | Muscle atonia | Muscle atonia may be used to discriminate REM from non-REM sleep. |
| | Eye movement | Eye movement may be used to discriminate REM from non-REM sleep. |
| Contextual/ Non-Physiological | Temperature | Ambient temperature may be a condition predisposing the patient to episodes of disordered breathing and may be useful in disordered breathing detection. |
| | Humidity | Humidity may be a condition predisposing the patient to episodes of disordered breathing and may be useful in disordered breathing detection. |
| | Pollution | Pollution may be a condition predisposing the patient to episodes of disordered breathing and may be useful in disordered breathing detection. |
| | Posture | Posture may be used to confirm or determine the patient is asleep. |
| | Activity | Patient activity may be used in relation to sleep detection. |
| | Location | Patient location may used to determine if the patient is in bed as a part of sleep detection. |
| | Altitude | Lower oxygen concentrations at higher altitudes tends to cause more central apnea |

In various implementations, episodes of disordered breathing may be detected and classified by analyzing the patient's respiration patterns. Methods and systems of disordered breathing detection based on respiration patterns are further described in commonly owned U.S. patent application Ser. No. 10/309,770, filed Dec. 4, 2002, which is incorporated herein be reference.

FIG. 7 illustrates normal respiration as represented by a signal produced by a transthoracic impedance sensor. The transthoracic impedance increases during respiratory inspiration and decreases during respiratory expiration. During non-REM sleep, a normal respiration pattern includes regular, rhythmic inspiration-expiration cycles without substantial interruptions.

In one embodiment, episodes of disordered breathing may be detected by evaluating the respiratory waveform output of the transthoracic impedance sensor. When the tidal volume (TV) of the patient's respiration, as indicated by the transthoracic impedance signal, falls below a hypopnea threshold, then a hypopnea event is declared. For example, a hypopnea event may be declared if the patient's tidal volume falls below about 50% of a recent average tidal volume or other baseline tidal volume value. If the patient's tidal volume falls further to an apnea threshold, e.g., about 10% of the recent average tidal volume or other baseline value, an apnea event is declared.

Figure 13:
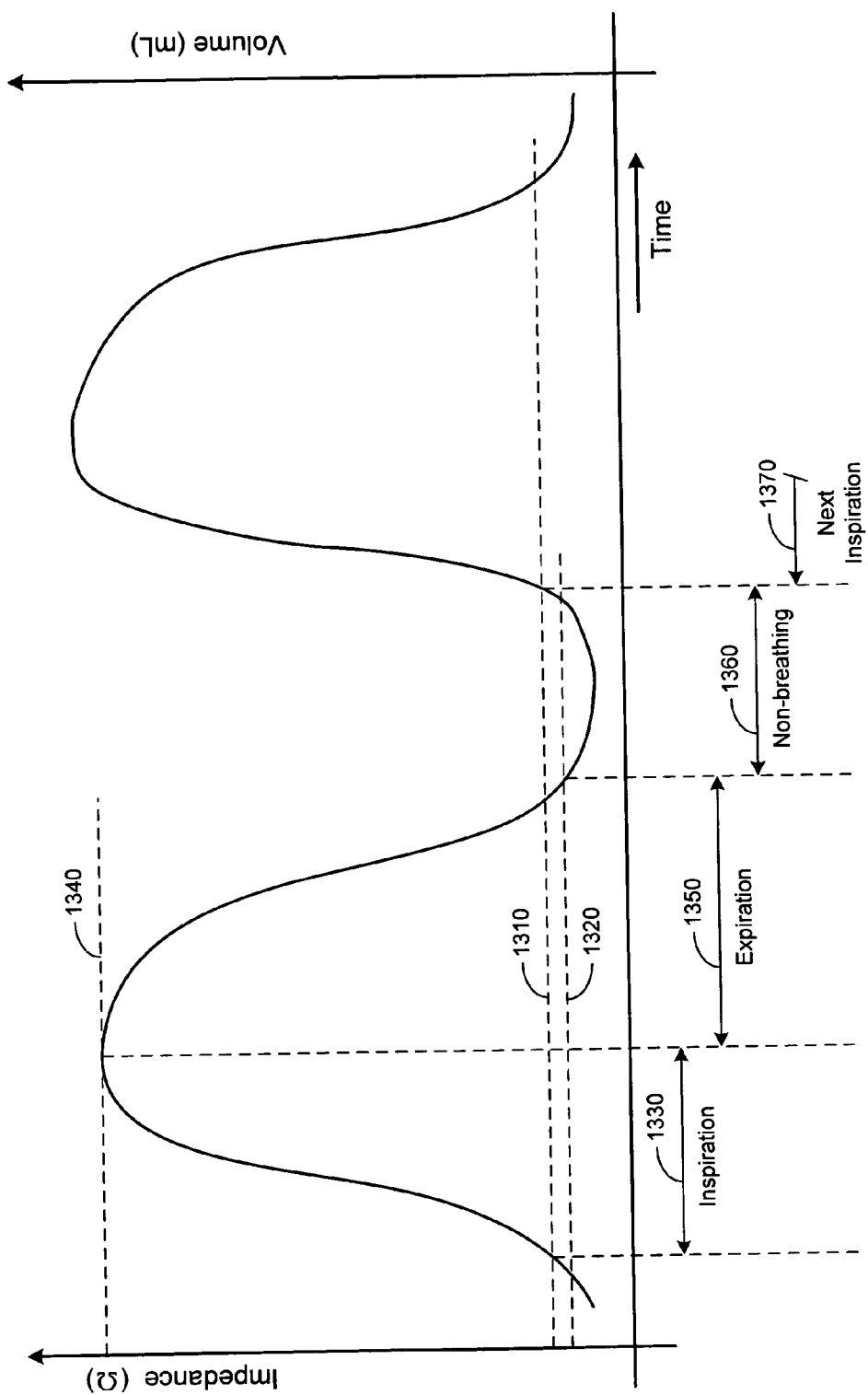
FIG. 13 is a respiration signal graph illustrating respiration intervals used for disordered breathing detection according to embodiments of the invention.

In another embodiment, detection of disordered breathing involves defining and examining a number of respiratory cycle intervals. FIG. 13 illustrates respiration intervals used for disordered breathing detection according to embodiments of the invention. A respiration cycle is divided into an inspiration period corresponding to the patient inhaling, an expiration period, corresponding to the patient exhaling, and a non-breathing period occurring between inhaling and exhaling. Respiration intervals are established using inspiration 1310 and expiration 1320 thresholds. The inspiration threshold 1310 marks the beginning of an inspiration period 1330 and is determined by the transthoracic impedance signal rising above the inspiration threshold 1310. The inspiration period 1330 ends when the transthoracic impedance signal is maximum 1340. A maximum transthoracic impedance signal 1340 corresponds to both the end of the inspiration interval 1330 and the beginning of the expiration interval 1350. The expiration interval 1350 continues until the transthoracic impedance falls below an expiration threshold 1320. A non-breathing interval 1360 starts from the end of the expiration period 1350 and continues until the beginning of the next inspiration period 1370.

Figure 14:
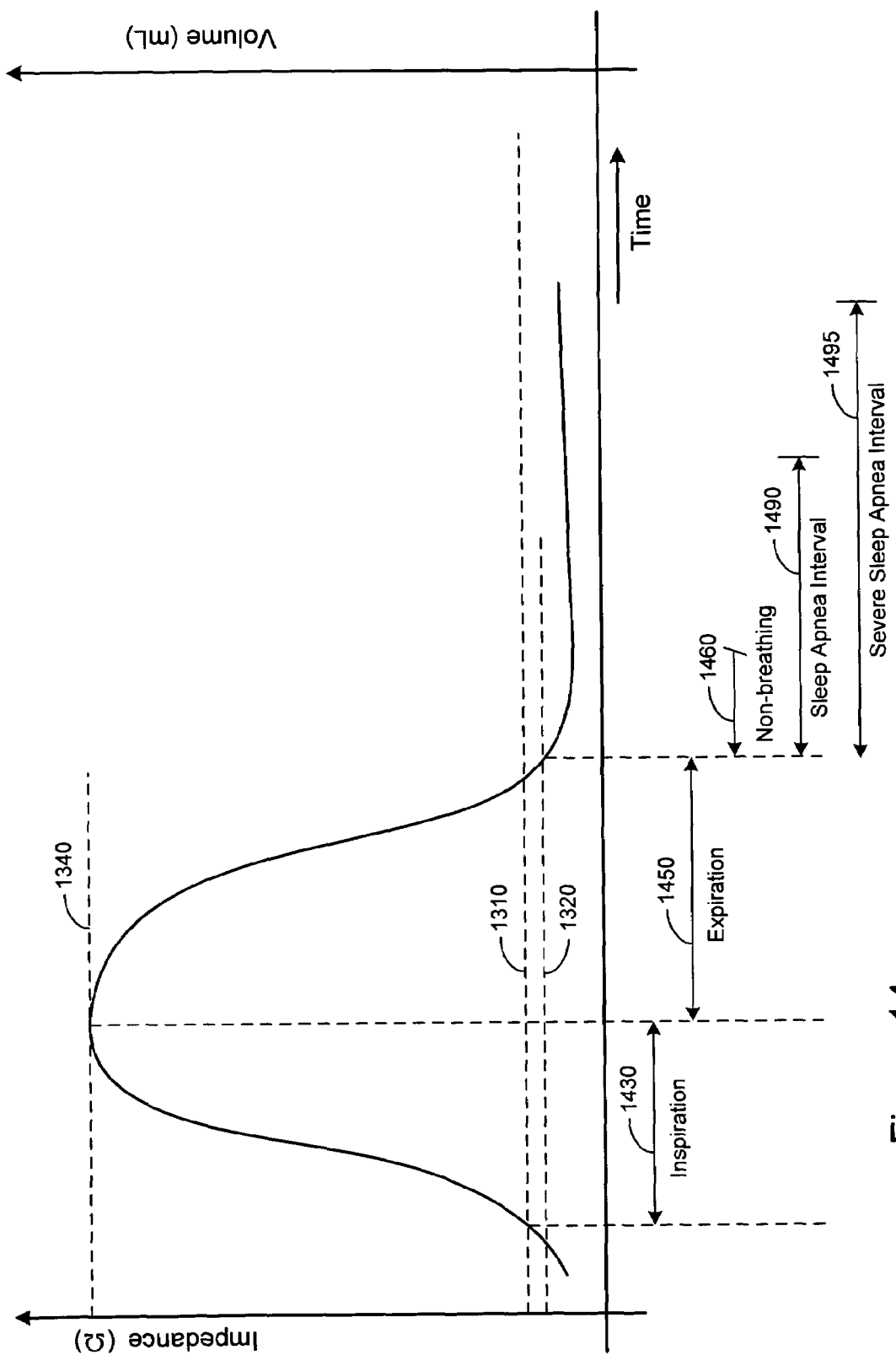
FIG. 14 is a graph of a respiration signal illustrating various intervals that may be used for detection of apnea in accordance with embodiments of the invention.

Detection of sleep apnea and severe sleep apnea according to embodiments of the invention is illustrated in FIG. 14. The patient's respiration is sensed and the respiration cycles are defined according to inspiration 1430, expiration 1450, and non-breathing 1460 intervals as described in connection with FIG. 13. A condition of sleep apnea is detected when a non-breathing period 1460 exceeds a first predetermined interval 1490, denoted the sleep apnea interval. A condition of severe sleep apnea is detected when the non-breathing period 1460 exceeds a second predetermined interval 1495, denoted the severe sleep apnea interval. For example, sleep apnea may be detected when the non-breathing interval exceeds about 10 seconds, and severe sleep apnea may be detected when the non-breathing interval exceeds about 20 seconds.

Figure 15A:
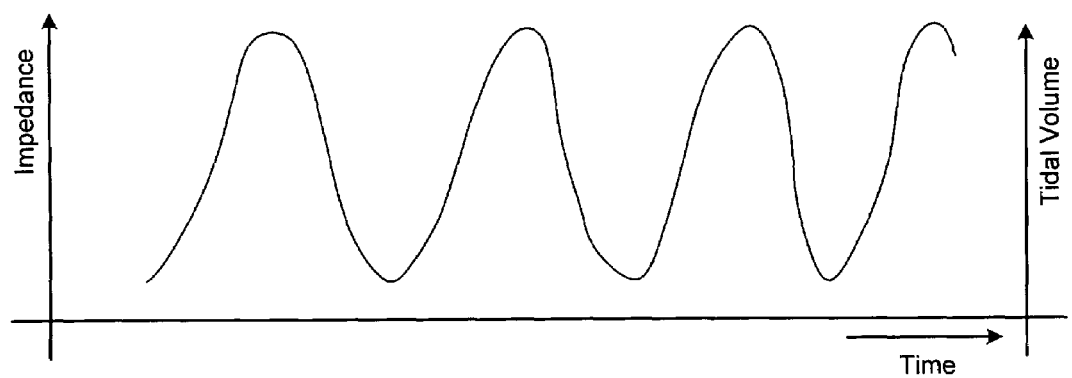
FIGS. 15A and 15B are respiration graphs illustrating normal respiration and abnormally shallow respiration utilized in detection of disordered breathing in accordance with embodiments of the invention.
Figure 15B:
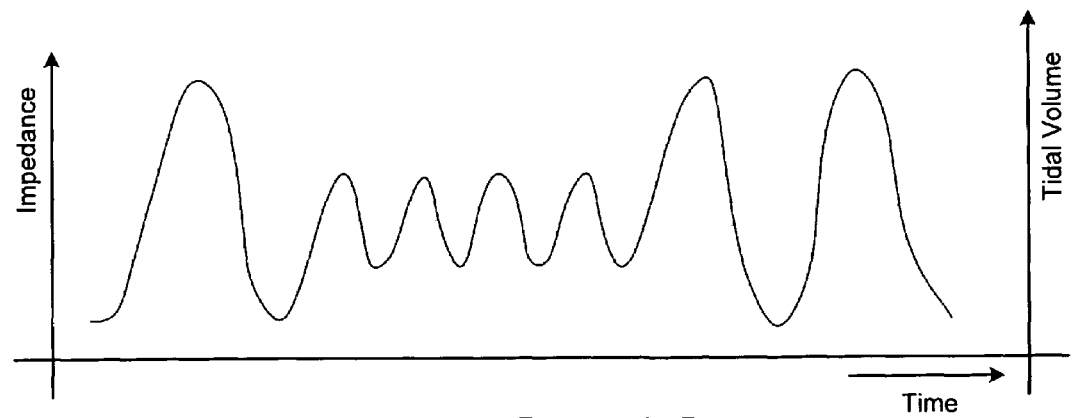

Hypopnea is a condition of disordered breathing characterized by abnormally shallow breathing. FIGS. 15A-15B are graphs of tidal volume derived from transthoracic impedance measurements. The graphs compare the tidal volume of a normal breathing cycle to the tidal volume of a hypopnea episode. FIG. 15A illustrates normal respiration tidal volume and rate. As shown in FIG. 15B, hypopnea involves a period of abnormally shallow respiration.

According to an embodiment of the invention, hypopnea is detected by comparing a patient's respiratory tidal volume to a hypopnea tidal volume threshold. The tidal volume for each respiration cycle is derived from transthoracic impedance measurements acquired in the manner described above. The hypopnea tidal volume threshold may be established using clinical results providing a representative tidal volume and duration of hypopnea events. In one configuration, hypopnea is detected when an average of the patient's respiratory tidal volume taken over a selected time interval falls below the hypopnea tidal volume threshold. Furthermore, various combinations of hypopnea cycles, breath intervals, and non-breathing intervals may be used to detect hypopnea, where the non-breathing intervals are determined as described above.

Figure 16:
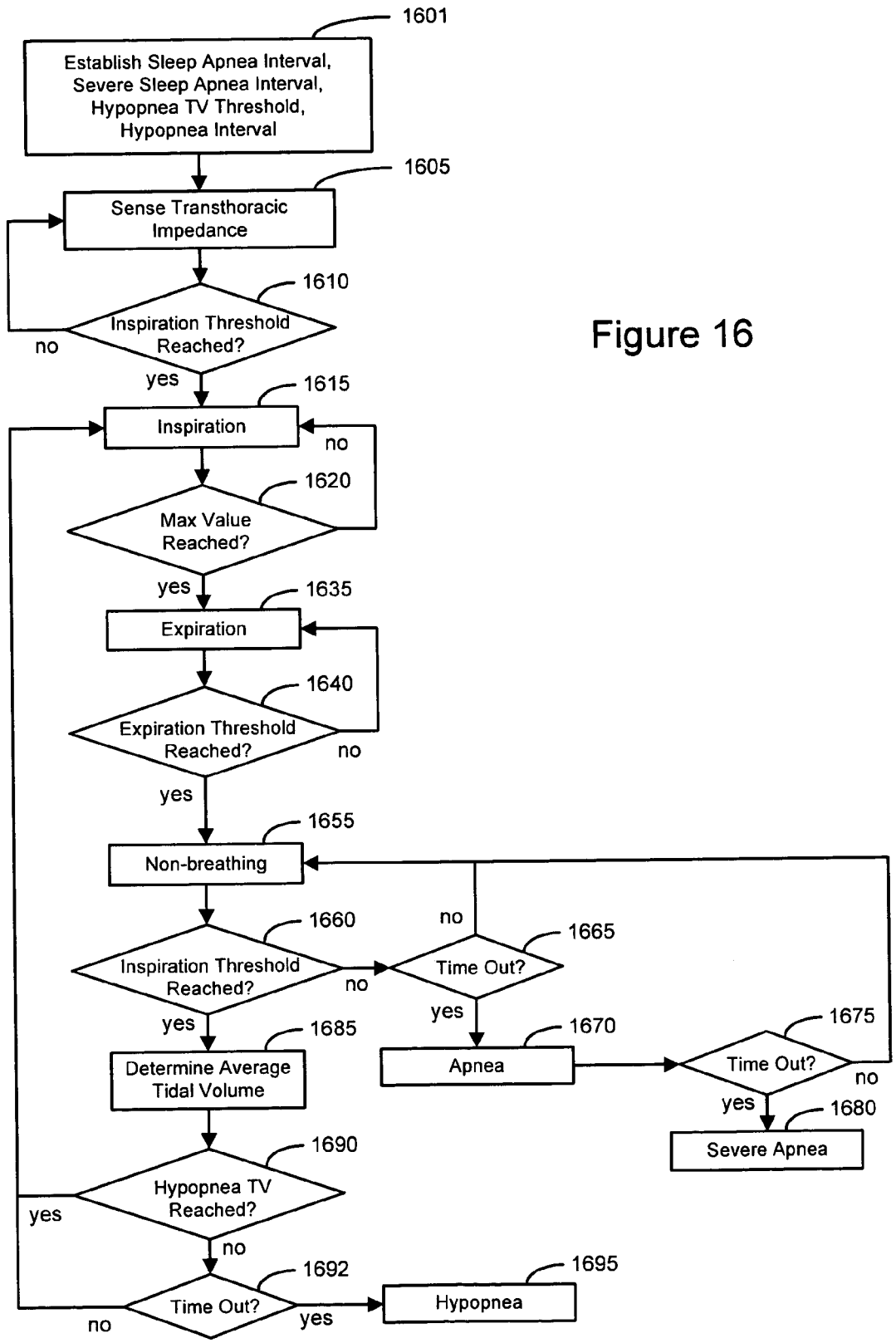
FIG. 16 is a flow chart illustrating a method of apnea and/or hypopnea detection according to embodiments of the invention.

FIG. 16 is a flow chart illustrating a method of apnea and/or hypopnea detection according to embodiments of the invention. Various parameters are established 1601 before analyzing the patient's respiration for disordered breathing episodes, including, for example, inspiration and expiration thresholds, sleep apnea interval, severe sleep apnea interval, and hypopnea tidal volume threshold.

The patient's transthoracic impedance is measured 1605 as described in more detail above. If the transthoracic impedance exceeds 1610 the inspiration threshold, the beginning of an inspiration interval is detected 1615. If the transthoracic impedance remains below 1610 the inspiration threshold, then the impedance signal is checked 1605 periodically until inspiration 1615 occurs.

During the inspiration interval, the patient's transthoracic impedance is monitored until a maximum value of the transthoracic impedance is detected 1620. Detection of the maximum value signals an end of the inspiration period and a beginning of an expiration period 1635.

The expiration interval is characterized by decreasing transthoracic impedance. When the transthoracic impedance falls 1640 below the expiration threshold, a non-breathing interval is detected 1655.

If the transthoracic impedance does not exceed 1660 the inspiration threshold within a first predetermined interval 1665, denoted the sleep apnea interval, then a condition of sleep apnea is detected 1670. Severe sleep apnea is detected 1680 if the non-breathing period extends beyond a second predetermined interval 1675, denoted the severe sleep apnea interval.

When the transthoracic impedance exceeds 1660 the inspiration threshold, the tidal volume from the peak-to-peak transthoracic impedance is calculated, along with a moving average of past tidal volumes 1685. The peak-to-peak transthoracic impedance provides a value proportional to the tidal volume of the respiration cycle. This value is compared to a hypopnea tidal volume threshold 1690. If the peak-to-peak transthoracic impedance is consistent with the hypopnea tidal volume threshold 1690 for a predetermined time 1692, then a hypopnea cycle is detected 1695.

Additional sensors, such as motion sensors, oximetry sensors, and/or posture sensors, may be used to confirm or verify the detection of a sleep apnea or hypopnea episode. The additional sensors may be employed to prevent false or missed detections of sleep apnea/hypopnea due to posture and/or motion related artifacts.

Another embodiment of the invention involves classifying respiration patterns as disordered breathing episodes based on the breath intervals and/or tidal volumes of one or more respiration cycles within the respiration patterns. According to this embodiment, the duration and tidal volumes associated with a respiration pattern are compared to duration and tidal volume thresholds. The respiration pattern is detected as a disordered breathing episode based on the comparison.

Figure 17:
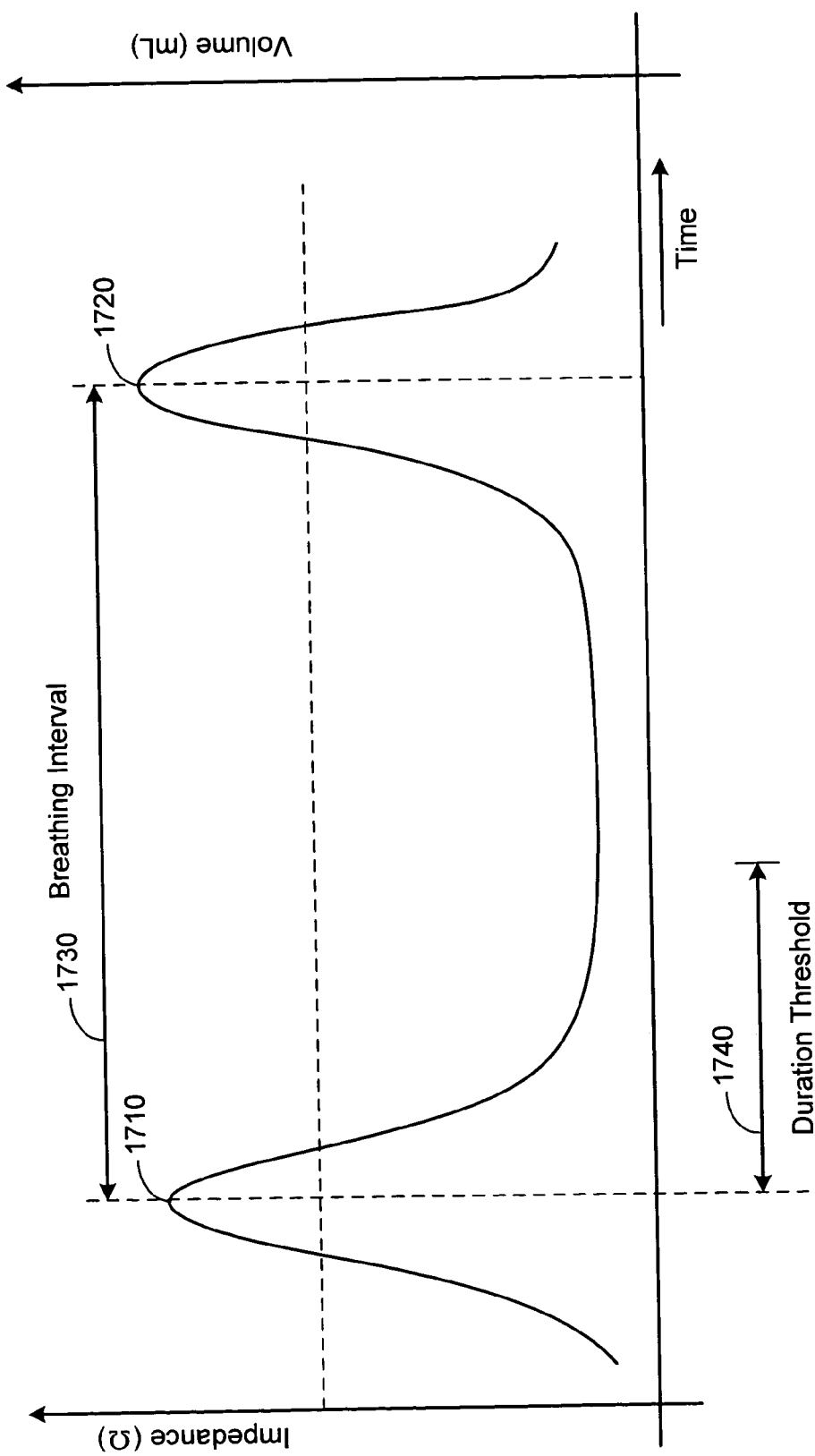
FIG. 17 is a respiration graph illustrating a breath interval utilized in connection with disordered breathing detection in accordance with embodiments of the invention.

According to principles of the invention, a breath interval is established for each respiration cycle. A breath interval represents the interval of time between successive breaths, as illustrated in FIG. 17. A breath interval 1730 may be defined in a variety of ways, for example, as the interval of time between successive maxima 1710, 1720 of the impedance signal waveform.

Detection of disordered breathing, in accordance with embodiments of the invention, involves the establishment of a duration threshold and a tidal volume threshold. If a breath interval exceeds the duration threshold, an apnea event is detected. Detection of sleep apnea, in accordance with this embodiment, is illustrated in the graph of FIG. 17. Apnea represents a period of non-breathing. A breath interval 1730 exceeding a duration threshold 1740 comprises an apnea episode.

Hypopnea may be detected using the duration threshold and tidal volume threshold. A hypopnea event represents a period of shallow breathing. Each respiration cycle in a hypopnea event is characterized by a tidal volume less than the tidal volume threshold. Further, the hypopnea event involves a period of shallow breathing greater than the duration threshold.

Figure 18:
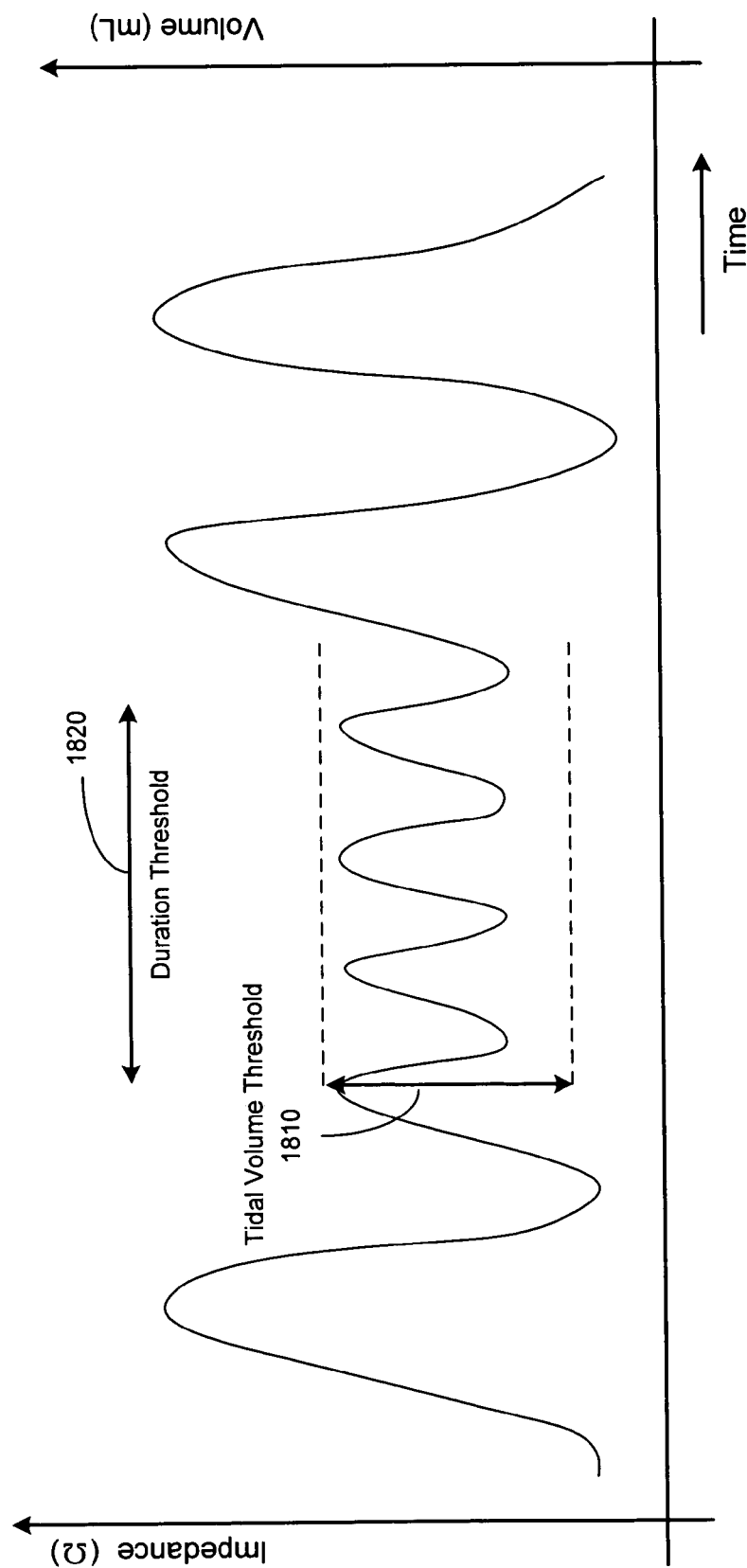
FIG. 18 is a respiration graph illustrating a hypopnea detection approach in accordance with embodiments of the invention.

A hypopnea detection approach, in accordance with embodiments of the invention, is illustrated in FIG. 18. Shallow breathing is detected when the tidal volume of one or more breaths is below a tidal volume threshold 1810. If the shallow breathing continues for an interval greater than a duration threshold 1820, then the breathing pattern represented by the sequence of shallow respiration cycles, is classified as a hypopnea event.

Figure 19:
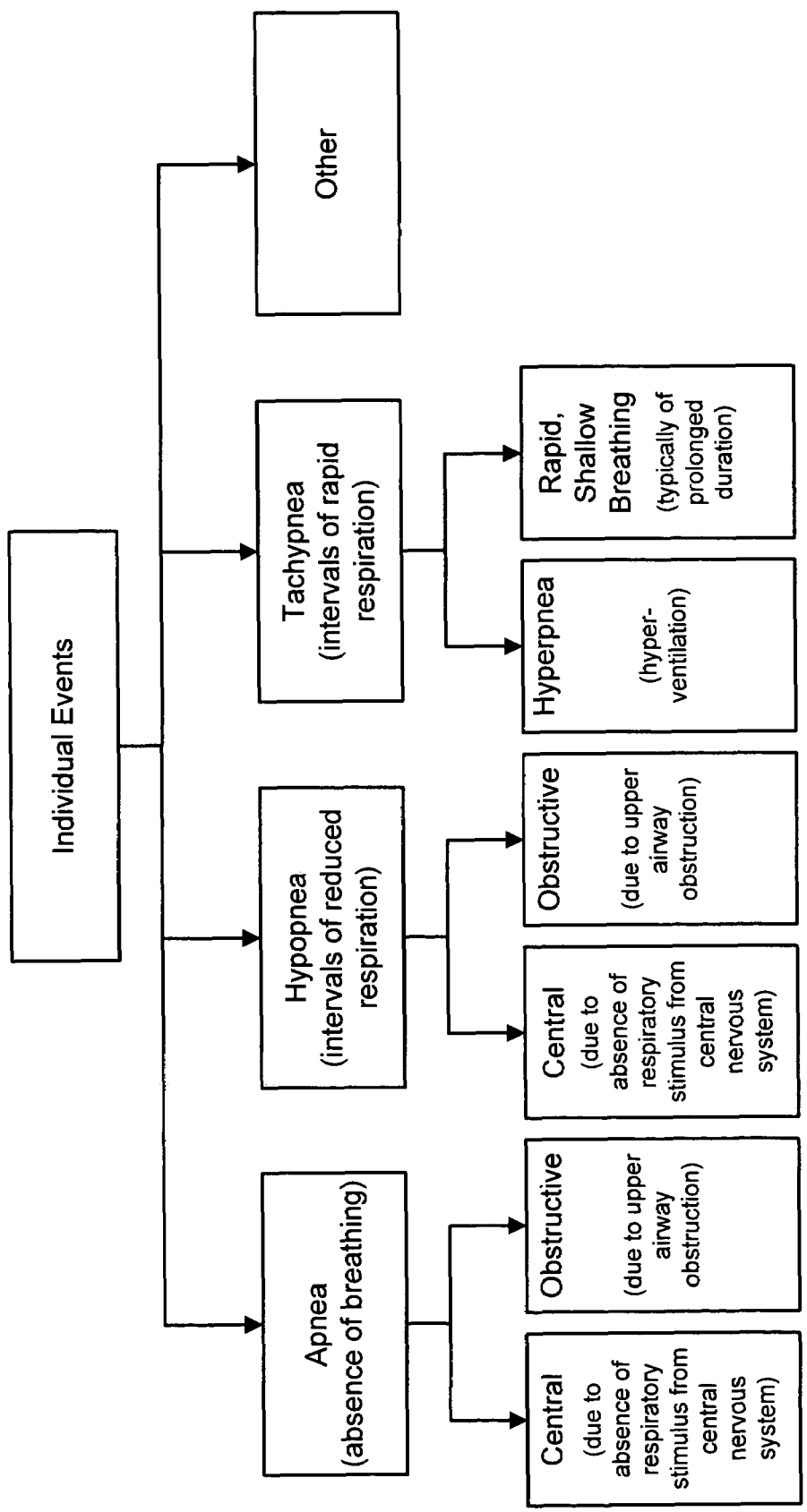
FIGS. 19 and 20 provide charts illustrating classification of individual disordered breathing events and series of periodically recurring disordered breathing events, respectively, in accordance with embodiments of the invention.
Figure 20:
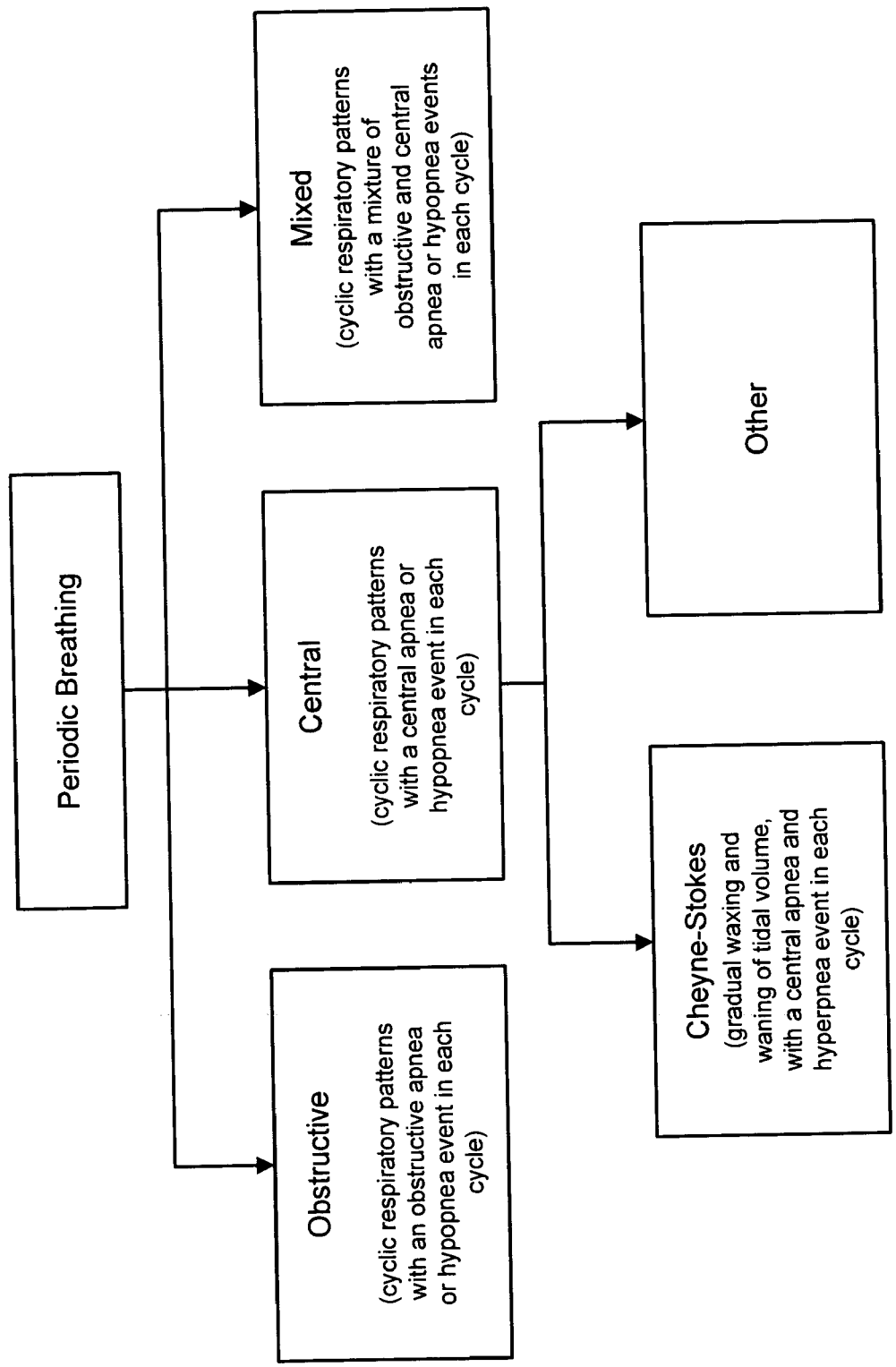

FIGS. 19 and 20 provide charts illustrating classification of individual disordered breathing events and series of periodically recurring disordered breathing events, respectively. As illustrated in FIG. 19, individual disordered breathing events may be grouped into apnea, hypopnea, tachypnea and other disordered breathing events. Apnea events are characterized by an absence of breathing. Intervals of reduced respiration are classified as hypopnea events. Tachypnea events include intervals of rapid respiration characterized by an elevated respiration rate.

As illustrated in FIG. 19, apnea and hypopnea events may be further subdivided as either central events, related to central nervous system dysfunction, or obstructive events, caused by upper airway obstruction. A tachypnea event may be further classified as a hyperpnea event, represented by hyperventilation, i.e., rapid deep breathing. A tachypnea event may alternatively be classified as rapid breathing, typically of prolonged duration.

FIG. 20 illustrates classification of combinations of periodically recurring disordered breathing events. Periodic breathing may be classified as obstructive, central or mixed. Obstructive periodic breathing is characterized by cyclic respiratory patterns with an obstructive apnea or hypopnea event in each cycle. Central periodic breathing involves cyclic respiratory patterns including a central apnea or hypopnea event in each cycle. Periodic breathing may also be of mixed origin. Mixed origin periodic breathing is characterized by cyclic respiratory patterns having a mixture of obstructive and central apnea events in each cycle. Cheyne-Stokes is a particular type of periodic breathing involving a gradual waxing and waning of tidal volume and having a central apnea and hyperpnea event in each cycle. Other manifestations of periodic breathing are also possible. Disordered breathing episodes may be classified based on the characteristic respiration patterns associated with particular types of disordered breathing.

Figure 21A:
FIGS. 21A-E are graphs illustrating respiration patterns that may be detected as disordered breathing episodes in accordance with embodiments of the invention.
Figure 21B:
Figure 21C:
Figure 21D:
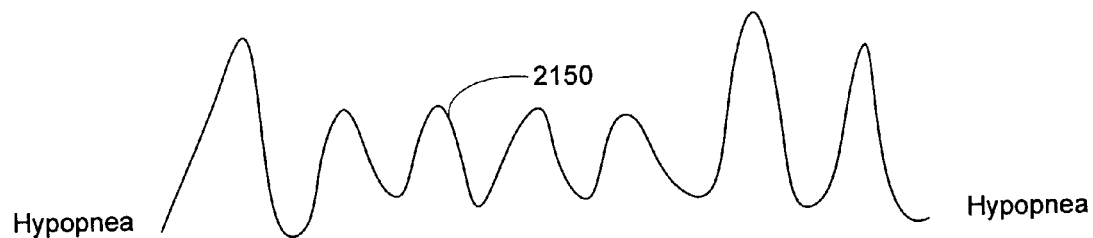
Figure 21E:
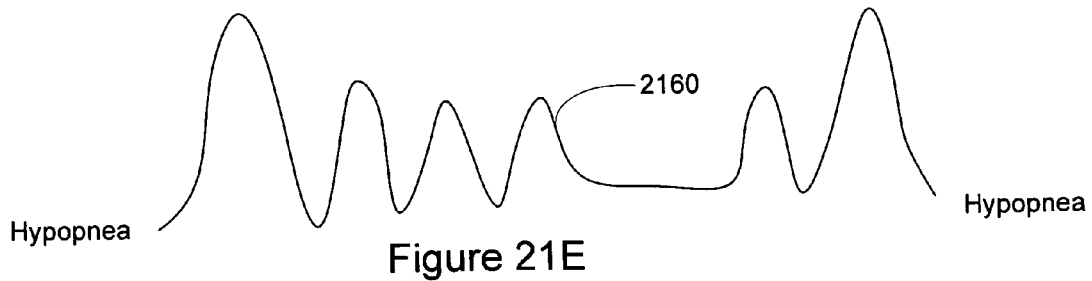

As illustrated in FIGS. 21A-E, a respiration pattern detected as a disordered breathing episode may include only an apnea respiration cycle 2110 (FIG. 21A), only hypopnea respiration cycles 2150 (FIG. 21D), or a mixture of hypopnea and apnea respiration cycles 2120 (FIG. 21B), 2130 (FIG. 21C), 2160 (FIG. 21E). A disordered breathing event 2120 may begin with an apnea respiration cycle and end with one or more hypopnea cycles. In another pattern, the disordered breathing event 2130 may begin with hypopnea cycles and end with an apnea cycle. In yet another pattern, a disordered breathing event 2160 may begin and end with hypopnea cycles with an apnea cycle in between the hypopnea cycles.

Figure 22:
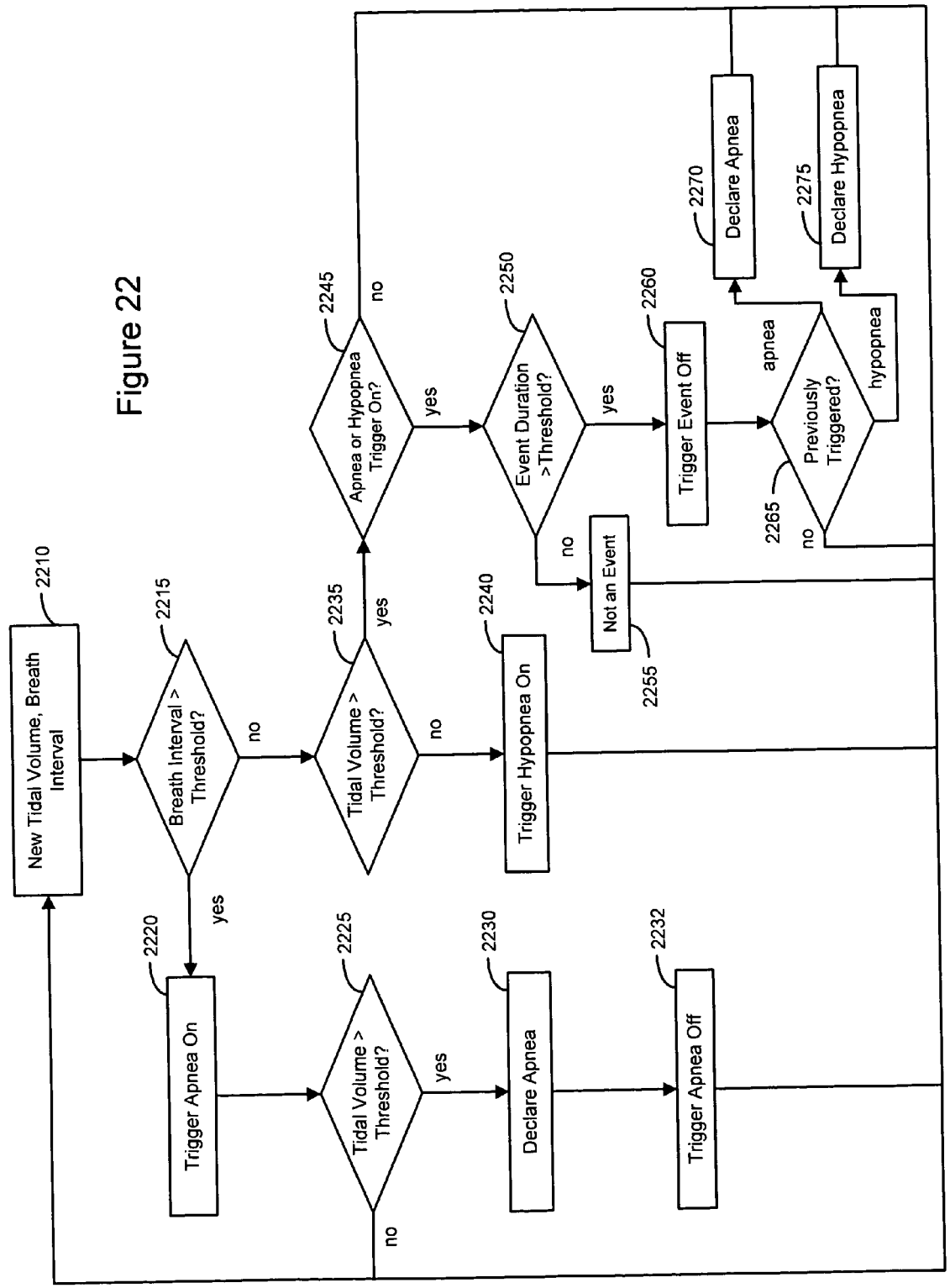
FIG. 22 is a flow graph of a method for detecting disordered breathing in accordance with embodiments of the invention.

FIG. 22 is a flow graph of a method for detecting disordered breathing in accordance with embodiments of the invention. The method illustrated in FIG. 22 operates by classifying breathing patterns using breath intervals in conjunction with tidal volume and duration thresholds as previously described above. In this example, a duration threshold and a tidal volume threshold are established for determining both apnea and hypopnea breath intervals. An apnea episode is detected if the breath interval exceeds the duration threshold. A hypopnea episode is detected if the tidal volume of successive breaths remains less than the tidal volume threshold for a period in excess of the duration threshold. Mixed apnea/hypopnea episodes may also occur. In these cases, the period of disordered breathing is characterized by shallow breaths or non-breathing intervals. During the mixed apnea/hypopnea episodes, the tidal volume of each breath remains less than the tidal volume threshold for a period exceeding the duration threshold.

Transthoracic impedance is sensed and used to determine the patient's respiration cycles. Each breath 2210 may be characterized by a breath interval, the interval of time between two impedance signal maxima, and a tidal volume (TV).

If a breath interval exceeds 2215 the duration threshold, then the respiration pattern is consistent with an apnea event, and an apnea event trigger is turned on 2220. If the tidal volume of the breath interval exceeds 2225 the tidal volume threshold, then the breathing pattern is characterized by two respiration cycles of normal volume separated by a non-breathing interval. This pattern represents a purely apneic disordered breathing event, and apnea is detected 2230. Because the final breath of the breath interval was normal, the apnea event trigger is turned off 2232, signaling the end of the disordered breathing episode. However, if the tidal volume of the breath interval does not exceed 2225 the tidal volume threshold, the disordered breathing period is continuing and the next breath is checked 2210.

If the breath interval does not exceed 2215 the duration threshold, then the tidal volume of the breath is checked 2235. If the tidal volume does not exceed 2235 the tidal volume threshold, the breathing pattern is consistent with a hypopnea cycle and a hypopnea event trigger is set on 2240. If the tidal volume exceeds the tidal volume threshold, then the breath is normal.

If a period of disordered breathing is in progress, detection of a normal breath signals the end of the disordered breathing. If disordered breathing was previously detected 2245, and if the disordered breathing event duration has not exceeded 2250 the duration threshold, and the current breath is normal, then no disordered breathing event is detected 2255. If disordered breathing was previously detected 2245, and if the disordered breathing event duration has extended for a period of time exceeding 2250 the duration threshold, and the current breath is normal, then the disordered breathing trigger is turned off 2260. In this situation, the duration of the disordered breathing episode was of sufficient duration to be classified as a disordered breathing episode. If an apnea event was previously triggered 2265, then an apnea event is declared 2270. If a hypopnea was previously triggered 2265, then a hypopnea event is declared 2275.

As previously discussed in connection with the flowchart of FIG. 1B above, the breathing therapy may be modified based on the sensed conditions. Adjustment of the external breathing therapy may involve initiating, terminating or modifying, the external breathing therapy. The external breathing therapy may be modified based on the effectiveness of the breathing therapy, the patient's compliance with the therapy, the impact of the external breathing therapy on the patient, and/or other factors. Once initiated, the system may continue to monitor parameters associated with the breathing therapy and the breathing therapy may be modified based on periodically updated assessments of therapy efficacy, patient comfort during therapy, sleep quality during therapy, interactions between therapies, or other factors, for example.

A subset of patient conditions, for example, one or more of the representative conditions listed in Table 1, may be used in connection with determining patient compliance with the breathing therapy. Another subset of patient conditions, which may overlap the conditions used for therapy compliance, may be used in connection with the detection of disordered breathing. Another subset may be used to assess therapy effectiveness. Yet another subset may be used to determine an impact of the therapy on the patient.

Acute responses to disordered breathing may be used to detect disordered breathing and both acute and chronic responses may be used to assess the efficacy and impact of disordered breathing therapy. Conditions used to assess therapy effectiveness may be different from, or the same as, conditions used to assess an impact of the therapy on the patient. Table 3 provides a representative set of conditions that may be used for therapy assessment with respect to both therapy efficacy and therapy impact.

TABLE 3

| Condition | Therapy Impact | Therapy Efficacy |
| --- | --- | --- |
| Arousal-Based Sleep Fragmentation Measures | May be used to assess therapy impact during sleep. | |
| Restful sleep (Patient reported) | May be used to assess therapy impact during sleep. | |
| Discomfort (Patient reported) | May be used to assess therapy impact. | |
| Pacing algorithm interaction | May be used to assess therapy impact. | |
| Remaining useful life of therapy device | May be used to assess therapy impact. | |
| Disturbed Breathing-Based Measures | | May be used to analyze/assess efficacy of therapy to mitigate disordered breathing episodes. |

TABLE 3-continued

| Condition | Therapy Impact | Therapy Efficacy |
|---|---|---|
| Respiration quality (Patient reported) | | May be used to analyze/assess efficacy of therapy to mitigate disordered breathing episodes. |
| Heart rate variability (HRV) | | Disordered breathing causes heart rate variability to decrease. Therapy may be modified based on changes in HRV |
| Blood pressure | | Disordered breathing causes blood pressure increase |
| Sympathetic nerve activity (SNA) | | Changes in sympathetic nerve activity are caused by disordered breathing. Therapy may be adjusted based on the level of SNA |
| Blood chemistry | | A number of disordered breathing related changes may occur in a patient's blood chemistry, including, e.g., higher norepinephrine levels, and lower $PaCO_2$ |

It is understood that the patient conditions that may be used in connection the medical systems described herein are not limited to the representative sets listed in Tables 1-3 or those described herein. Further, although illustrative sensing methods for detecting the patient conditions listed above are provided, it is understood that the patient conditions may be detected using a wide variety of technologies. The embodiments and features described in herein are not limited to the particular patient conditions or the particular sensing technologies provided.

In accordance with various embodiments of the invention, conditions related to sleep quality, e.g., sleep fragmentation and/or other arousal-based measures, patient-reported restful sleep, and patient-reported discomfort during therapy, may be used to assess the impact of the therapy on the patient. For example, if a patient is receiving effective disordered breathing therapy and has low sleep fragmentation, reports restful sleep, and reports no discomfort, the adverse effects of the therapy on the patient may be relatively low. If sleep fragmentation is relatively high, or if the patient reports discomfort or feeling tired after sleeping, these conditions may indicate that therapy is causing sleep disturbances and/or other undesirable effects.

Because disordered breathing generally occurs during sleep, it may be particularly important to assess sleep quality during disordered breathing therapy delivery. It is undesirable to provide therapy that eliminates the disordered breathing but increases sleep fragmentation. In such a situation, the disordered breathing therapy may exacerbate the adverse effects produced by the respiratory disturbances. Thus, it may be preferable to assess the impact of the therapy on the patient and adjust the therapy to improve sleep quality.

Sleep fragmentation and sleep disruptions may also occur if disordered breathing therapy is ineffective and disordered breathing occurs during sleep. Therefore, a therapy impact assessment based on detected sleep quality and/or patient-reported restful sleep may preferably take into account an assessment of therapy effectiveness.

Evaluation of the impact of disordered breathing therapy on the patient preferably takes into consideration the impact of disordered breathing therapy on the overall therapeutic goals for the patient, including cardiac pacing goals and disordered breathing goals. The disordered breathing therapy may involve a variety of therapy regimens implemented to achieve predetermined therapeutic goals. The effectiveness of the therapy, or the degree to which the therapy meets one or more therapeutic goals may be assessed by detecting and analyzing episodes of disordered breathing that occur during therapy delivery.

For example, a therapeutic goal may involve terminating a disordered breathing episode and the disordered breathing therapy may be adapted to achieve this goal. Additionally, or alternatively, a therapeutic goal may involve terminating a disordered breathing episode and preventing further disordered breathing. In this example situation, the therapy regimen may be adapted to provide a first therapy to terminate the disordered breathing episode and provide a second preventative therapy to reduce or eliminate further disordered breathing episodes. The second preventative therapy may be adapted to reduce episodes of disordered breathing below a predetermined disordered breathing episode threshold. A disordered breathing episode threshold may be expressed, for example, in terms of an apnea/hypopnea index (AHI) or percent time in periodic breathing (% PB).

Figure 23:
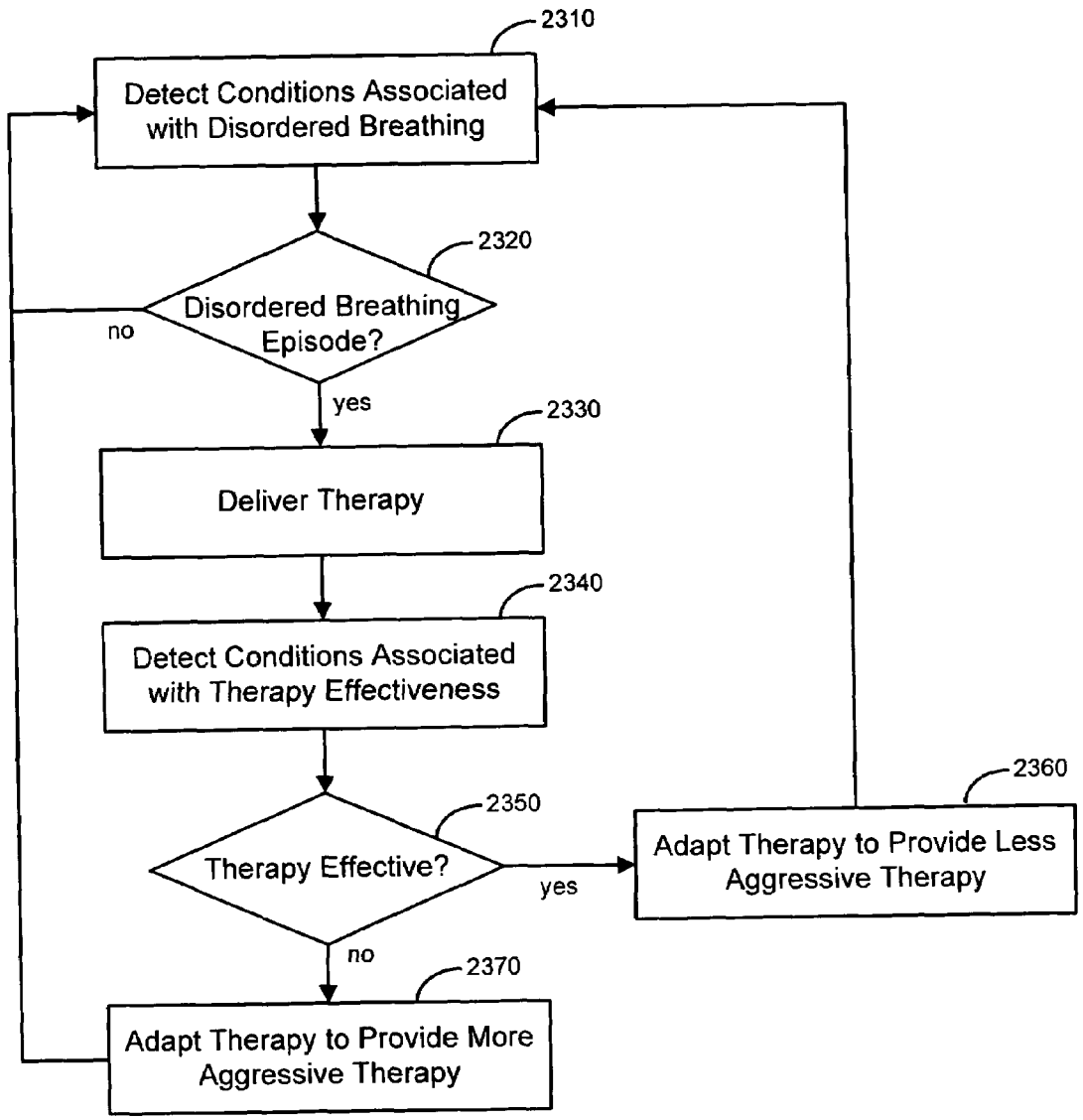
FIGS. 23 and 24 are flow charts illustrating methods of adapting a disordered breathing therapy according to embodiments of the invention.
Figure 24:
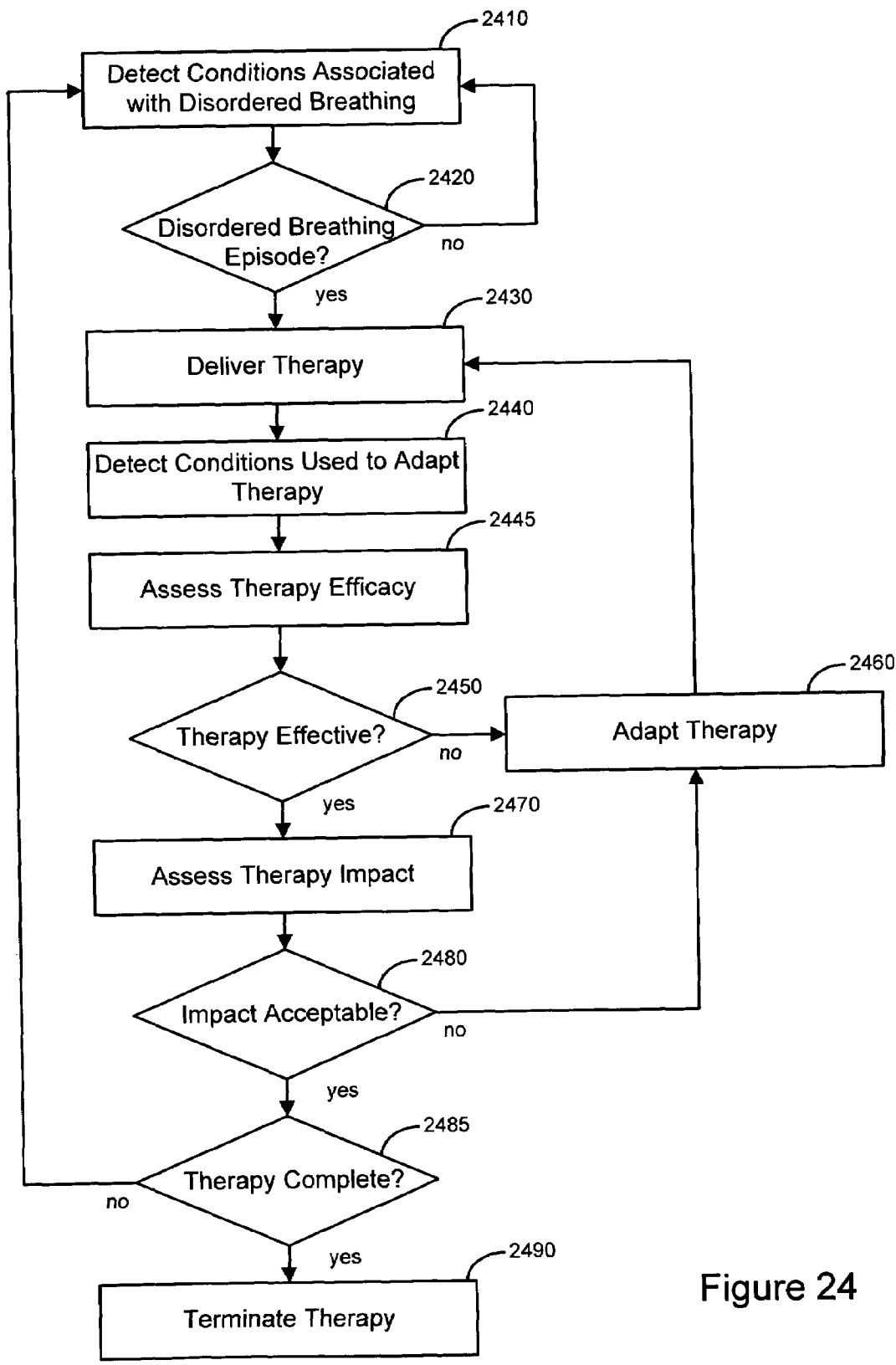

FIGS. 23 and 24 are flow graphs illustrating methods of adapting a disordered breathing therapy according to embodiments of the invention. The flow chart of FIG. 23 illustrates a method of adapting disordered breathing therapy to achieve a desired level of therapy efficacy. In this embodiment, a first set of conditions associated with disordered breathing is detected 2310 and used to determine if a disordered breathing episode is occurring. If disordered breathing is detected 2320, disordered breathing therapy is delivered 2330 to the patient to mitigate the disordered breathing. In one embodiment, the therapy delivered to the patient may initially involve air delivered at a first predetermined pressure.

A second set of conditions associated with therapy effectiveness is sensed 2340 and used to assess the effectiveness of the therapy. The detected conditions used to assess the efficacy of the therapy and adapt the therapy to mitigate disordered breathing may represent one or more of the acute conditions associated with disordered breathing, e.g., detected episodes of interrupted breathing, hypoxia, arousals, negative intrathoracic pressure, blood pressure, and heart rate or blood pressure surges.

Additionally, or alternatively, the conditions used to assess therapy efficacy and adapt the breathing therapy may include one or more chronic conditions associated with disordered breathing, including, for example, decreased heart rate variability, increased blood pressure, chronic changes in sympathetic nerve activity, and changes in blood chemistry, such as increased levels of $PaCO_2$ and norepinephrine levels, among others.

In general, a therapeutic goal in the treatment of disordered breathing is to provide the least aggressive therapy that effectively mitigates, terminates or prevents the patient's disordered breathing or achieves a particular therapeutic goal associated with disordered breathing therapy. The disordered breathing therapy regimen may be enhanced by increasing the intensity or level of therapy to more effectively mitigate the disordered breathing. Alternatively, the disordered breathing therapy regimen may be enhanced by reducing the intensity or level of therapy while maintaining a desired decrease in the severity or frequency of disordered breathing episodes, thus reducing undesirable side effects from the therapy and extending the device lifetime.

If the therapy effectiveness is acceptable 2350, e.g., terminates or reduces the patient's disordered breathing or meets some other desired goal, then the therapy may be adapted 2360 to provide a less aggressive therapy, e.g., air delivered at a decreased pressure. If the therapy is not effective 2350, then the therapy may be adapted 2370 to enhance therapy efficacy by providing a more aggressive therapy, e.g., delivering air at an increased pressure.

In one embodiment, therapy may be determined to be ineffective if disordered breathing continues unmitigated following therapy delivery. In this situation, the therapy may be adapted to provide a more aggressive therapy. In another embodiment, if the disordered breathing decreases sufficiently in severity, or is otherwise sufficiently mitigated, the therapy may be enhanced by adapting the therapy to provide a less aggressive therapy, e.g., decreased air pressure. As previously discussed, a less aggressive therapy is preferable to reduce the risk of arousal and to provide a more comfortable therapy to the patient, for example.

The flowchart of FIG. 24 illustrates a method of adapting a disordered breathing therapy in accordance with embodiments of the invention. In this example, a first set of conditions associated with disordered breathing is detected 2410 and used to determine if a disordered breathing episode is occurring. If disordered breathing is detected 2420, therapy is delivered 2430 to the patient to mitigate the disordered breathing.

A second set of conditions is detected 2440 and used to adapt the therapy. Based on the second set of sensed conditions, the therapy efficacy is assessed 2445. If the therapy efficacy is not acceptable 2450, then the therapy may be adapted 2460 to enhance therapy efficacy. If the therapy efficacy is acceptable 2450, then the impact of the therapy on the patient may be assessed 2470.

If the therapy impact on the patient is acceptable 2480, the system continues to deliver the therapy. When the therapy regimen is complete 2485, then therapy is terminated 2490. If the therapy impact on the patient exceeds acceptable limits, the therapy impact is not acceptable 2480, and the therapy may be adapted 2460 to reduce the therapy impact.

The methods illustrated in the flow graphs of FIGS. 23 and 24 contemplate real-time monitoring breathing therapy parameters allowing the therapy system to dynamically adjust the therapy regimen to accommodate the changing needs of the patient. In one configuration, the therapy may be adjusted during the period that therapy is delivered to the patient. In another configuration, the therapy may be adapted between disordered breathing episodes or from night-to-night based on assessment of the efficacy of therapy delivered in connection with one or more previously detected disordered breathing episodes.

Methods, devices, and systems implementing a coordinated approach to monitoring breathing treatment and/or providing therapy for disordered breathing may incorporate one or more of the features, structures, methods, or combinations thereof described herein below. For example, a medical system may be implemented to include one or more of the features and/or processes described herein. It is intended that such a method, device, or system need not include all of the features and functions described herein, but may be implemented to include one or more selected features and functions that provide unique structures and/or functionality.

A number of the examples presented herein involve block diagrams illustrating functional blocks used for coordinated monitoring, diagnosis and/or therapy functions in accordance with embodiments of the present invention. It will be understood by those skilled in the art that there exist many possible configurations in which these functional blocks can be arranged and implemented. The examples depicted herein provide examples of possible functional arrangements used to implement the approaches of the invention.

It is understood that the components and functionality depicted in the figures and described herein can be implemented in hardware, software, or a combination of hardware and software. It is further understood that the components and functionality depicted as separate or discrete blocks/elements in the figures in general can be implemented in combination with other components and functionality, and that the depiction of such components and functionality in individual or integral form is for purposes of clarity of explanation, and not of limitation.

What is claimed is:

1. A method of monitoring respiration therapy delivered to a patient, comprising:
    sensing one or more conditions associated with patient-external breathing therapy; and
    implantably monitoring the patient-external breathing therapy based on the one or more sensed conditions;
    wherein implantably monitoring the patient-external breathing therapy comprises implantably monitoring patient use of the patient-external breathing therapy; and
    wherein implantably monitoring the patient use of the patient-external breathing therapy comprises comparing the patient use of patient-external breathing therapy with a prescribed use of the patient-external breathing therapy.

2. The method of claim 1, wherein sensing the one or more conditions comprises sensing one or more conditions associated with positive airway pressure breathing therapy.

3. The method of claim 1, wherein sensing the one or more conditions comprises sensing one or more cardiovascular system conditions.

4. The method of claim 1, wherein sensing the one or more conditions comprises sensing one or more respiratory system conditions.

5. The method of claim 1, wherein sensing the one or more conditions comprises sensing a proximity of the patient to a location of a therapy device delivering the patient-external breathing therapy.

6. The method of claim 1, wherein implantably monitoring the patient-external breathing therapy comprises implantably monitoring an effectiveness of the patient-external breathing therapy.

7. The method of claim 6, wherein implantably monitoring the effectiveness of the patient-external breathing therapy comprises:
    detecting disordered breathing episodes; and
    monitoring the effectiveness of the patient-external breathing therapy based on the detected disordered breathing episodes.

8. The method of claim 6, wherein implantably monitoring the effectiveness of the patient-external breathing therapy comprises determining night-to-night changes in the effectiveness of the patient-external breathing therapy.

9. The method of claim 1, wherein implantably monitoring the patient use of the patient-external breathing therapy comprises:
    analying respiratory waveform morphology; and
    monitoring the patient use of the patient-external breathing therapy based on the respiratory waveform morphology analysis.

10. The method of claim 1, further comprising providing one or more alert signals associated with the patient use of the patient-external breathing therapy.

11. The method of claim 1, wherein implantably monitoring the patient-external breathing therapy comprises implantably monitoring an impact of the patient-external breathing therapy on the patient.

12. The method of claim 1, wherein implantably monitoring the patient-external breathing therapy comprises implantably monitoring one or more interactions between the patient-external breathing therapy and another therapy delivered to the patient.

13. The method of claim 1, further comprising adapting the patient-external breathing therapy based on the one or more sensed conditions.

14. A medical system, comprising:
a sensing system configured to sense conditions associated with a patient-external breathing therapy; and
an implantable monitoring device, coupled to the sensing system, the implantable monitoring device configured to monitor the patient-external breathing therapy based on the one or more sensed conditions;
wherein the implantable monitoring device is also configured to monitor patient use of the patient-external breathing therapy and to compare the patient use with a prescribed use of the patient-external breathing therapy.

15. The system of claim 14, wherein the patient-external breathing therapy comprises positive airway pressure therapy.

16. The system of claim 14, wherein the implantable monitoring device is disposed within a housing of a cardiac therapy device.

17. The system of claim 14, wherein the sensing system comprises a transthoracic impedance sensor configured to sense respiration signals.

18. The system of claim 14, wherein the sensing system comprises cardiac electrodes configured to sense cardiac electrical signals.

19. The system of claim 14, wherein the implantable monitoring device is configured to monitor an effectiveness of the patient-external breathing therapy based on the sensed conditions.

20. The system of claim 14, wherein the implantable monitoring device comprises a disordered breathing detector configured to detect disordered breathing using the sensed conditions and to monitor the patient-external breathing therapy based on the detection of disordered breathing.

21. The system of claim 14, wherein:
the sensing system is configured to sense patient proximity to a device delivering the patient-external breathing therapy; and
the implantable monitoring device is configured to monitor patient use of the patient-external breathing therapy based on the patient proximity.

22. The system of claim 14, wherein the implantable monitoring device comprises a communication interface for communicatively coupling with a remote device and the implantable monitoring device is configured to transmit information associated with the one or more sensed conditions to the remote device.

23. The system of claim 14, wherein the implantable monitoring device comprises a memory configured to store information associated with the one or more sensed conditions.

24. A medical system, comprising:
means for sensing one or more conditions associated with patient-external breathing therapy;
means for implantably monitoring the patient-external breathing therapy based on the one or more sensed conditions; and
means for compairing patient usage of the patient-external breathing therapy to a prescribed usage.

25. The system of claim 24, further comprising:
means for detecting disordered breathing; and
means for implantably monitoring the patient-external breathing therapy based on the detection of disordered breathing.

26. The system of claim 24, further comprising means for monitoring an effectiveness of the patient-external breathing therapy based on the one or more sensed conditions.

27. The system of claim 24, further comprising means for monitoring patient usage of the patient-external breathing therapy.

* * * * *

UNITED STATES PATENT AND TRADEMARK OFFICE
CERTIFICATE OF CORRECTION

| | | |
|---|---|---|
| PATENT NO. | : 7,468,040 B2 | Page 1 of 1 |
| APPLICATION NO. | : 10/929826 | |
| DATED | : December 23, 2008 | |
| INVENTOR(S) | : Jesse W. Harley et al. | |

It is certified that error appears in the above-identified patent and that said Letters Patent is hereby corrected as shown below:

Column 38, Claim 24, line 25: "compairing" should be --comparing--.

Signed and Sealed this

Twenty-eighth Day of April, 2009

JOHN DOLL
*Acting Director of the United States Patent and Trademark Office*